(12) United States Patent
Fischer et al.

(10) Patent No.: US 6,642,180 B1
(45) Date of Patent: Nov. 4, 2003

(54) BIPHENYL-SUBSTITUTED CYCLIC KETOENOLS AS PESTICIDES

(75) Inventors: Reiner Fischer, Monheim (DE); Alan Graff, Leverkusen (DE); Thomas Bretschneider, Lohmar (DE); Christoph Erdelen, Leichlingen (DE); Mark Wilhelm Drewes, Langenfeld (DE); Dieter Feucht, Monheim (DE)

(73) Assignee: Bayer Aktiengesellschaft, Leverkusen (DE)

( * ) Notice: Subject to any disclaimer, the term of this patent is extended or adjusted under 35 U.S.C. 154(b) by 87 days.

(21) Appl. No.: 10/048,764

(22) PCT Filed: Jul. 18, 2000

(86) PCT No.: PCT/EP00/06852
§ 371 (c)(1),
(2), (4) Date: Jan. 25, 2002

(87) PCT Pub. No.: WO01/09092
PCT Pub. Date: Feb. 8, 2001

(30) Foreign Application Priority Data

Jul. 30, 1999 (DE) ......................... 199 35 963

(51) Int. Cl.⁷ .................. C07D 207/40; C07D 307/94; C07D 487/04; A01N 43/34; A01N 31/00

(52) U.S. Cl. .................. 504/246; 568/329; 568/530; 504/262; 504/263; 504/239; 504/252; 504/265; 504/266; 504/282; 504/283; 504/289; 504/292; 504/299; 504/303; 504/348; 544/235; 544/54; 546/183; 546/228.7; 548/131; 548/134; 548/136; 548/143; 548/194; 548/367.1; 548/544; 549/66; 549/78; 549/292; 549/319; 549/330; 560/27

(58) Field of Search .................. 504/239, 246, 504/252, 262, 263, 265, 266, 282, 283, 285, 292, 299, 303, 348; 544/54, 335; 546/183; 548/278.7, 131, 134, 136, 143, 194, 367.1, 544, 408; 549/66, 78, 292, 319, 330; 560/27; 568/329, 530

(56) References Cited

U.S. PATENT DOCUMENTS

| | | | |
|---|---|---|---|
| 3,781,302 A * | 12/1973 | Fuchs et al. .................. 549/24 |
| 4,104,043 A | 8/1978 | Durden, Jr. et al. .......... 71/107 |
| 4,175,135 A | 11/1979 | Haines ....................... 424/311 |
| 4,209,432 A | 6/1980 | Roth ....................... 260/29.2 M |
| 4,256,657 A | 3/1981 | Wheeler ................. 260/465 D |
| 4,256,658 A | 3/1981 | Wheeler ................. 260/465 D |
| 4,256,659 A | 3/1981 | Wheeler ................. 260/465 D |
| 4,257,858 A | 3/1981 | Wheeler ................. 204/158 R |
| 4,283,348 A | 8/1981 | Wheeler ................. 260/465 D |
| 4,303,669 A | 12/1981 | D'Silva ....................... 424/282 |
| 4,338,122 A | 7/1982 | Wheeler ....................... 71/122 |
| 4,351,666 A | 9/1982 | Koerwer ....................... 71/106 |
| 4,409,153 A | 10/1983 | Hodakowski ............... 260/946 |
| 4,436,666 A | 3/1984 | Wheeler ................. 260/455 B |
| 4,526,723 A | 7/1985 | Wheeler et al. .......... 260/410.5 |
| 4,551,547 A | 11/1985 | Wheeler ....................... 560/255 |
| 4,613,617 A | 9/1986 | Sousa ........................... 514/521 |
| 4,632,698 A | 12/1986 | Wheeler ....................... 71/106 |
| 4,659,372 A | 4/1987 | Wheeler ....................... 71/106 |
| 4,925,868 A | 5/1990 | Terao et al. .................... 514/425 |
| 4,985,063 A | 1/1991 | Fischer et al. .................. 71/88 |
| 5,045,560 A | 9/1991 | Fischer et al. ............... 514/425 |
| 5,091,537 A | 2/1992 | Fischer et al. ............... 546/226 |
| 5,094,681 A | 3/1992 | Krämer et al. .................. 71/88 |
| 5,116,836 A | 5/1992 | Fischer et al. ............. 514/224.2 |
| 5,142,065 A | 8/1992 | Fischer et al. ............... 548/533 |
| 5,186,737 A | 2/1993 | Fischer et al. ............... 504/283 |
| 5,207,817 A | 5/1993 | Krämer et al. ............... 504/299 |
| 5,225,434 A | 7/1993 | Bertram et al. ............... 514/411 |
| 5,258,527 A | 11/1993 | Krauskopf et al. .......... 548/543 |
| 5,393,729 A | 2/1995 | Fischer et al. ............... 504/128 |
| 5,420,155 A | 5/1995 | Kulagowski et al. ........ 514/425 |
| 5,462,913 A | 10/1995 | Fischer et al. ............... 504/138 |
| 5,504,057 A | 4/1996 | Fischer et al. ............... 504/283 |
| 5,565,450 A | 10/1996 | Fischer et al. ............. 514/227.2 |
| 5,567,671 A | 10/1996 | Fischer et al. ............... 504/283 |
| 5,589,469 A | 12/1996 | Fischer et al. ................. 514/91 |
| 5,602,078 A | 2/1997 | Fischer et al. ............... 504/283 |
| 5,616,536 A | 4/1997 | Fischer et al. ............... 504/225 |
| 5,622,917 A | 4/1997 | Fischer et al. ............... 504/283 |
| 5,677,449 A | 10/1997 | Fischer et al. ............... 544/165 |
| 5,683,965 A | 11/1997 | Bachmann et al. .......... 504/238 |
| 5,808,135 A | 9/1998 | Fischer et al. ............... 560/129 |
| 5,830,826 A | 11/1998 | Fischer et al. ............... 504/195 |
| 5,840,661 A | 11/1998 | Fischer et al. ............... 504/348 |
| 5,977,029 A | 11/1999 | Fischer et al. ............... 504/292 |
| 5,994,274 A | 11/1999 | Fischer et al. ............... 504/282 |
| 6,071,937 A | 6/2000 | Bretschneider et al. ...... 514/336 |
| 6,110,872 A | 8/2000 | Lieb et al. ................... 504/284 |
| 6,114,374 A | 9/2000 | Lieb et al. ................... 514/424 |
| 6,140,358 A | 10/2000 | Lieb et al. ................... 514/425 |
| 6,150,304 A | 11/2000 | Fischer et al. ............... 504/309 |
| 6,200,932 B1 | 3/2001 | Fischer et al. ............... 504/225 |
| 6,251,833 B1 | 6/2001 | Erdelen et al. ............... 504/348 |
| 6,255,342 B1 | 7/2001 | Lieb et al. ................... 514/533 |
| 6,271,180 B2 | 8/2001 | Lieb et al. ................... 504/292 |
| 6,288,102 B1 | 9/2001 | Hagemann et al. .......... 514/409 |
| 6,316,486 B1 | 11/2001 | Lieb et al. ................... 514/411 |
| 6,358,887 B1 | 3/2002 | Fischer et al. ............... 504/284 |
| 6,359,151 B2 | 3/2002 | Lieb et al. ................... 549/265 |
| 6,380,246 B1 | 4/2002 | Lieb et al. ................... 514/462 |
| 6,388,123 B1 | 5/2002 | Lieb et al. ..................... 560/76 |
| 6,391,912 B1 | 5/2002 | Hagemann et al. .......... 514/444 |
| 6,417,370 B1 | 7/2002 | Lieb et al. ................... 548/408 |
| 6,451,843 B1 | 9/2002 | Lieb et al. ................... 514/422 |
| 6,458,965 B1 | 10/2002 | Lieb et al. ................... 548/408 |
| 6,472,419 B1 | 10/2002 | Fischer et al. ............... 514/425 |
| 6,486,343 B1 | 11/2002 | Lieb et al. ..................... 560/39 |
| 2001/0004629 A1 | 6/2001 | Lieb et al. ................... 504/292 |
| 2002/0010204 A1 | 1/2002 | Lieb et al. ................... 514/424 |
| 2002/0072617 A1 | 6/2002 | Hagemann et al. .......... 548/541 |
| 2002/0161034 A1 | 10/2002 | Hagemann et al. .......... 514/432 |

FOREIGN PATENT DOCUMENTS

| | | |
|---|---|---|
| EP | 442077 | 8/1991 |
| WO | 96/02539 | 2/1996 |
| WO | 97/14667 | 4/1997 |
| WO | 98/05638 | 2/1998 |
| WO | 99/16748 | 4/1999 |
| WO | 99/24437 | 5/1999 |
| WO | 99/43649 | 9/1999 |
| WO | 99/48869 | 9/1999 |
| WO | 99/55673 | 11/1999 |

OTHER PUBLICATIONS

Chem. Pharm. Bull, S. Suzuki et al, 15 (8), pp. 1120–1122, (month unavailable) 1967, "Studies on Antiviral Agents. N.*[1] Biological Activity of Tenuazonic Acid Derivatives".

Liebigs Ann. Chem., (month unavailable) 1985, pp. 1095–1098, R. Schmierer et al, "Cyclisierung von N–Acylalanin– und N–Acylglycinestern".

Arch. Pharm., (month unavailable) 1976, 309, pp. 558–564, A. M. Chirazi et al, "Zur Synthese von Kawalactonderivaten".

Chem. Ber., 91, (month unavailable) 1958, p. 2849, K–H. Boltze et al, Zur Synthese 3–substituierter 4–Hydroxy–pyrone–(2), I Ringschlüsse mit Malonsäure–dichloriden.

Monatsh, 95, 147, (month unavailable, 1964, E. Ziegler et al, "Synthesen von Heterocyclen, 52. Mitt.: Über Derivate des 2–Phenyl–4–hydroxy–[1,3–thiazinons–(6)]$^1$".

J. Heterocycl. Chem., 10, 223, (month unavailable) 1973, R. Ketcham et al, "Synthesis of Heterocycles. 174 (1,2) Substituted Thiazines and Bisthiazinyls from Dithiooxamide and Trichlorophenyl Malonates".

Tetrahedron, vol. 48, No. 36, pp. 7519–7526, (month unavailable) 1992, J. Micklefield et al, "Alkylation and Acylation of 5–Phenylsulphonyl– and 5–Cyanobutyrolactones".

J. Chem. Soc., (month unavailable) 1967, pp. 405–409, R. L. Edwards et al, "Constituents of the Higher Fungi. Part IV.* Involutin, A Diphenyl–cyclopenteneone from *Paxillus involutus* (Oeder ex Fries)".

J. Economic Entomology, vol. 66, No. 2, (month unavailable) 1973, pp. 584–586, A. A. Sousa et al, "Esters of 3–Hydroxy–2–Arylindones, a New Class of Acaricide$^1$".

J. Org. Chem., vol. 44, No. 26, (month unavailable) 1979, pp. 4906–4912, T. N. Wheeler, "Novel Photochemical Synthesis of 2–Aryl–1,3–cyclohexanediones".

* cited by examiner

*Primary Examiner*—Bruck Kifle
*Assistant Examiner*—Thomas McKenzie
(74) *Attorney, Agent, or Firm*—Richard E. L. Henderson; John E. Mrozinski, Jr.

(57) ABSTRACT

The present invention relates to novel biphenyl-substituted cyclic ketoenols of the formula (I)

(I)

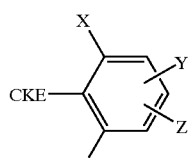

in which
  W represents hydrogen, halogen, alkyl, alkoxy, alkenyloxy, halogenoalkyl, halogenoalkoxy, halogenoalkenyloxy, nitro or cyano,
  X represents halogen, alkyl, alkoxy, alkenyloxy, alkylthio, alkylsulphinyl, alkylsulphonyl, halogenoalkyl, halogenoalkoxy, halogenoalkenyloxy, nitro, cyano or in each case optionally substituted phenyl, phenoxy, phenylthio, phenylalkoxy or phenylalkylthio,
  Y represents in each case optionally substituted cycloalkyl, aryl or hetaryl,
  Z represents hydrogen, halogen, alkyl, alkoxy, halogenoalkyl or halogenoalkoxy,
  CKE represents one of the groups

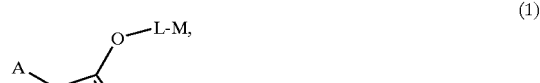 (1)

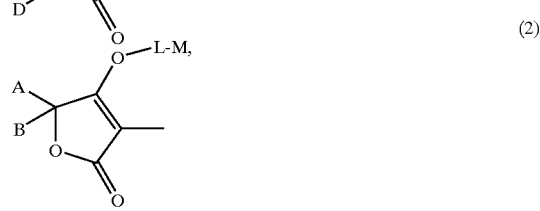

(2)

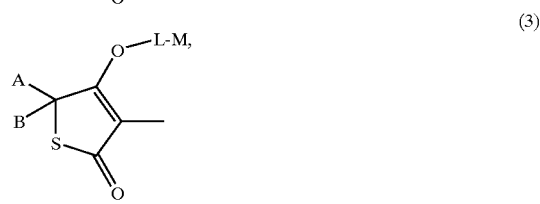

(3)

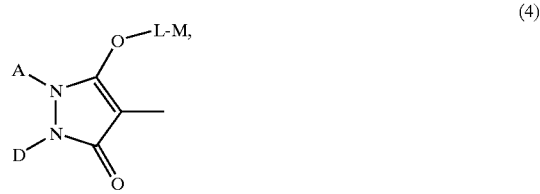

(4)

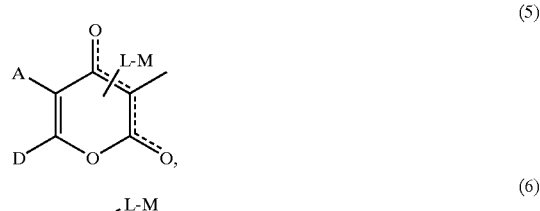

(5)

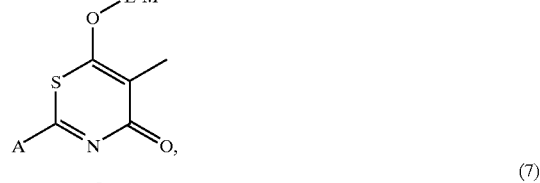

(6)

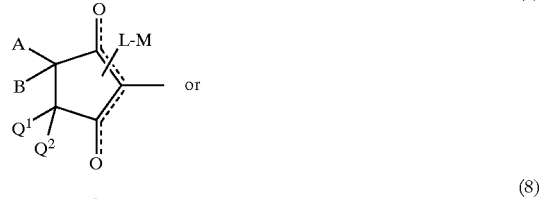

(7)

or

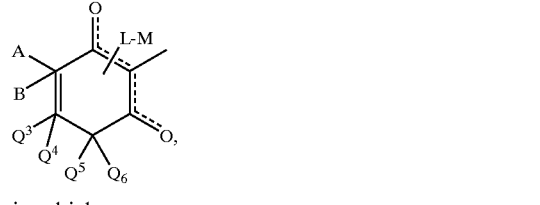 (8)

in which
A, B, D, L, M, $Q^1$, $Q^2$, $Q^3$, $Q^4$, $Q^5$ and $Q^6$ are as defined in the description, to preparation and to their use as pesticides and herbicides.

9 Claims, No Drawings

US 6,642,180 B1

BIPHENYL-SUBSTITUTED CYCLIC KETOENOLS AS PESTICIDES

FIELD OF THE INVENTION

The present invention relates to novel biphenyl-substituted cyclic ketoenols, to a plurality of processes for their preparation and to their use in agriculture, animal health and in the domestic and hygiene area, as pesticides and herbicides.

BACKGROUND OF THE INVENTION

Pharmaceutical properties of 3-acyl-pyrrolidine-2,4-diones have already been described (S. Suzuki et al. Chem. Pharm. Bull. 15 1120 (1967)). Furthermore, N-phenylpyrrolidine-2,4-diones have been synthesized by R. Schmierer and H. Mildenberger (Liebigs Ann. Chem. 1985, 1095). A biological activity of these compounds has not been described.

SUMMARY OF THE INVENTION

The present invention provides biphenyl-substituted cyclic ketoenols of the formula (I)

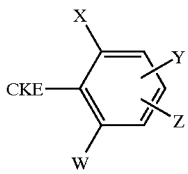

(I)

wherein

W represents hydrogen, halogen, alkyl, alkoxy, alkenyloxy, halogenoalkyl, halogenoalkoxy, halogenoalkenyloxy, nitro or cyano, X represents halogen, alkyl, alkoxy, alkenyloxy, alkylthio, alkylsulphinyl, alkylsulphonyl, halogenoalkyl, halogenoalkoxy, halogenoalkenyloxy, nitro, cyano or optionally substituted phenyl, phenoxy, phenylthio, phenylalkoxy or phenylalkylthio, Y represents optionally substituted cycloalkyl, aryl or hetaryl, Z represents hydrogen, halogen, alkyl, alkoxy, halogenoalkyl or halogenoalkoxy, and CKE represents one of the groups

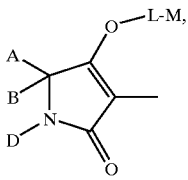

(1)

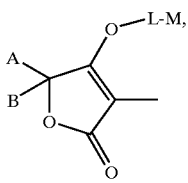

(2)

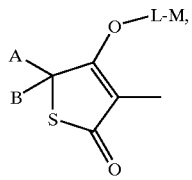

(3)

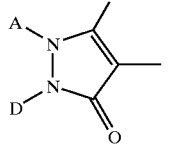

(4)

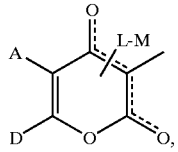

(5)

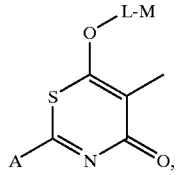

(6)

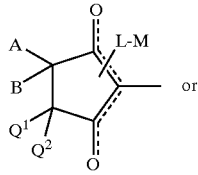

(7) or

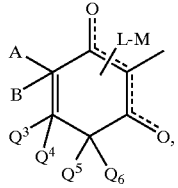

(8)

wherein
A, B, D, L, M, $Q^1$, $Q^2$, $Q^3$, $Q^4$, $Q^5$ and $Q^6$ are as described herein.

The present invention further provides processes for the preparation of the disclosed compounds. The compounds of the present invention are useful as pesticides and herbicides.

DETAILED DESCRIPTION OF THE INVENTION

EP-A-0 262 399 and GB-A-2 266 888 disclose compounds of a similar structure (3-aryl-pyrrolidine-2,4-diones) of which, however, no herbicidal, insecticidal or acaricidal activity has become known. Unsubstituted bicyclic 3-aryl-pyrrolidine-2,4-dione derivatives (EP-A-355 599 and EP-415 211) and substituted monocyclic 3-aryl-pyrrolidine-2,4-dione derivatives (EP-A-377 893 and EP-442 077) having herbicidal, insecticidal or acaricidal activity are known.

Also known are polycyclic 3-arylpyrrolidine-2,4-dione derivatives (EP-442 073) and 1H-arylpyrrolidine-dione derivatives (EP-456 063, EP-521 334, EP-596 298, EP-613

884, EP-613 885, WO 95/01997, WO 95/26954, WO 95/20572, EP-A-0 668 267, WO 96/25 395, WO 96/35 664, WO 97/01 535, WO 97/02 243 and WO 97/36 868, WO 98/05 638, WO 98/06721, WO 98/25928, WO 99/16748, WO 99/24437).

It is known that certain substituted $\Delta^3$-dihydrofuran-2-one derivatives have herbicidal properties (cf. DE-A-4 014 420). The synthesis of the tetronic acid derivatives used as starting materials, (such as, for example, 3-(2-methyl-phenyl)-4-hydroxy-5-(4-fluorophenyl)-$\Delta^3$-dihydrofuran-2-one) is likewise described in DE-A-4 014 420.

Compounds of a simular structure are known from the publication Campbell et al., J. Chem. Soc., Perkin Trans. 1, 1985, (8) 1567–76 without any insecticidal and/or acaricidal activity being mentioned. Furthermore, 3-aryl-$\Delta^3$-dihydrofuranone derivatives having herbicidal, acaricidal and insecticidal properties are known from EP-A-528 156, EP-A-0 647 637, WO 95/26 345, WO 96/20 196, WO 96/25 395, WO 96/35 664, WO 97/01 535, WO 97/02 243 and WO 97/36 868, WO 98/05 638, WO 99/16748, WO 98/25928. 3-Aryl-$\Delta^3$-dihydrothiophenone-derivatives are likewise known (WO 95/26 345, 96/25 395, WO 97/01 535, WO 97/02 243, WO 97/36 868, WO 98/05 638, WO 98/25928).

Also known from the literature are certain 3H-pyrazol-3-one derivatives, such as, for example, 1,2-diethyl-1,2-dihydro-5-hydroxy-4-phenyl-3H-pyrazol-3-one or {[5-oxo-1,2-diphenyl-4-(p-sulphophenyl)-3-pyrazolin-3-yl]-oxy}, disodium salt, or p-(3-hydroxy-5-oxo-1,2-diphenyl-3-pyrazolin-4-yl)-benzenesulphonic acid (cf. J. Heterocycl. Chem., 25(5), 1301–1305, 1988 or J. Heterocycl. Chem., 25(5), 1307–1310, 1988 or Zh. Obshch. Khim., 34(7), 2397–2402, 1964). However, a biological activity of these compounds is not described.

Furthermore, it is known that the trisodium salt of 4,4',4''-(5-hydroxy-3-oxo-1H-pyrazol-1,2,4(3H)-triyl)-tris-benzenesulphonic acid has pharmacological properties (cf. Farmakol. Toksikol. (Moscow), 38(2), 180–186, 1976). However, it is not known to be used in crop protection.

Moreover, EP-508 126 and WO 92/16 510, WO 96/21 652 describe 4-aryl-pyrazolidine-3,5-dione derivatives having herbicidal, acaricidal and insecticidal properties. Additionally, 4-arylpyrazolidines have become known, of which fungicidal properties have been described (WO 96/36 229, WO 96/36 615, WO 96/36 616, WO 96/36 633).

Certain phenyl-pyrone derivatives which are unsubstituted in the phenyl ring have already become known (cf A. M. Chirazi, T. Kappe and E. Ziegler, Arch. Pharm. 309, 558 (1976) and K. -H. Boltze and K. Heidenbluth, Chem. Ber. 91, 2849), a possible use of these compounds as pesticides not being mentioned. Phenyl-pyrone derivatives which are substituted in the phenyl ring and have herbicidal, acaricidal and insecticidal properties are described in EP-A-588 137, WO 96/25 395, WO 96/35 664, WO 97/01 535, WO 97/02 243, WO 97/16 436, WO 97/19 941 and WO 97/36 868, WO 98/05 638.

Certain 5-phenyl-1,3-thiazine derivatives which are unsubstituted in the phenyl ring have already become known (cf. E. Ziegler and E. Steiner, Monatsh. 95, 147 (1964), R. Ketcham, T. Kappe and E. Ziegler, J. Heterocycl. Chem. 10, 223 (1973)), a possible use of these compounds as pesticides not being mentioned. 5-Phenyl-1,3-thiazine derivatives which are substituted in the phenyl ring and have herbicidal, acaricidal and insecticidal activity are described in WO 94/14 785, WO 96/02 539, WO 96/35 664, WO 97/01 535, WO 97/02 243, WO 97/02 243, WO 97/36 868.

It is known that certain substituted 2-arylcyclopentanediones have herbicidal and acaricidal properties (cf., for example, U.S. Pat. Nos. 4,283,348; 4,338,122; 4,436,666; 4,526,723; 4,551,547; 4,632,698; WO 96/01 798; WO 96/03 366 and also WO 97/14 667, WO 98/39281). Moreover, compounds of a similar structure are known; 3-hydroxy-5,5-dimethyl-2-phenylcyclopent-2-ene-1-one from the publication Micklefield et al., Tetrahedron, (1992), 7519–26 and the natural product involutine (–)-cis-5-(3,4-dihydroxyphenyl)-3,4-dihydroxy-2-(4-hydroxyphenyl)-cyclopent-2-enone from the publication Edwards et al., J. Chem. Soc. S, (1967), 405–9. An insecticidal or acaricidal activuty has not been described. Moreover, 2-(2,4,6-trimethylphenyl)-1,3-indanedione is known from the publication J. Economic Entomology, 66, (1973), 584 and the Offenlegungsschrift DE-2 361 084, with herbicidal and acaricidal activities being mentioned.

It is known that certain substituted 2-arylcyclohexanediones have herbicidal and acaricidal properties (U.S. Pat. Nos. 4,175,135, 4,209,432, 4,256,657, 4,256,658, 4,256,659, 4,257,858, 4,283,348, 4,303,669, 4,351,666, 4,409,153, 4,436,666, 4,526,723, 4,613,617, 4,659,372, DE-2 813 341, and also Wheeler, T. N., J. Org. Chem. 44, 4906 (1979)).

However, the activity and the activity spectrum of these compounds are, in particular at low application rates and concentrations, not always entirely satisfactory. Furthermore, the compatibility of these compounds with plants is not always satisfactory.

This invention, accordingly, provides novel compounds of the formula (I)

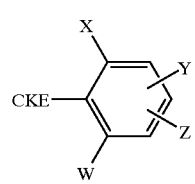

(I)

in which

W represents hydrogen, halogen, alkyl, alkoxy, alkenyloxy, halogenoalkyl, halogenoalkoxy, halogenoalkenyloxy, nitro or cyano, X represents halogen, alkyl, alkoxy, alkenyloxy, alkylthio, alkylsulphinyl, alkylsulphonyl, halogenoalkyl, halogenoalkoxy, halogenoalkenyloxy, nitro, cyano or in each case optionally substituted phenyl, phenoxy, phenylthio, phenylalkoxy or phenylalkylthio, Y represents in each case optionally substituted cycloalkyl, aryl or hetaryl, Z represents hydrogen, halogen, alkyl, alkoxy, halogenoalkyl or halogenoalkoxy, CKE represents one of the groups

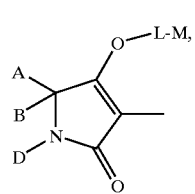

(1)

-continued

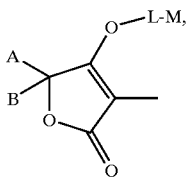
(2)

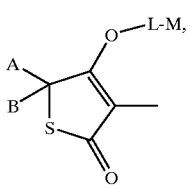
(3)

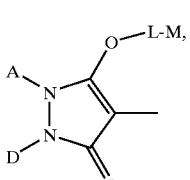
(4)

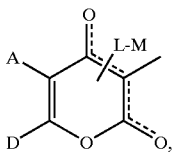
(5)

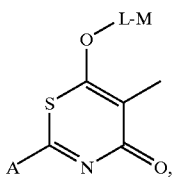
(6)

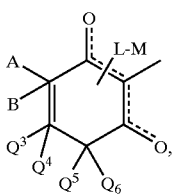
(7)

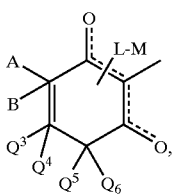
(8)

in which
A represents hydrogen, in each case optionally halogen-substituted alkyl, alkenyl, alkoxyalkyl, polyalkoxyalkyl, alkylthioalkyl, saturated or unsaturated, optionally substituted cycloalkyl, optionally at least one ring atom is replaced by a heteroatom, or in each case optionally halogen-, alkyl-, halogenoalkyl, alkoxy-, halogenoalkoxy-, cyano- or nitro-substituted aryl, arylalkyl or hetaryl,
B represents hydrogen, alkyl or alkoxyalkyl, or
A and B together with the carbon atom to which they are attached represent a saturated or unsaturated, unsubstituted or substituted cycle which optionally contains at least one heteroatom,
D represents hydrogen or an optionally substituted radical from the group consisting of alkyl, alkenyl, alkinyl, alkoxyalkyl, polyalkoxyalkyl, alkylthioalkyl, saturated or unsaturated cycloalkyl, in which optionally one or more ring members are replaced by heteroatoms, arylalkyl, aryl, hetarylalkyl or hetaryl or
A and D together with the atoms to which they are attached represent a saturated or unsaturated cycle which is unsubstituted or substituted in the A,D moiety and optionally contains at least one (in the case of CKE=(4) further) heteroatom, or
A and $Q^1$ together represent alkanediyl or alkenediyl, each of which is optionally substituted by in each case optionally substituted alkyl, hydroxyl, alkoxy, alkylthio, cycloalkyl, benzyloxy or aryl, or
$Q^1$ represents hydrogen or alkyl,
$Q^4$, $Q^5$ and $Q^6$ independently of one another represent hydrogen or alkyl,
$Q^3$ represents hydrogen, alkyl, alkoxyalkyl, alkylthioalkyl, optionally substituted cycloalkyl (in which optionally one methylene group is replaced by oxygen or sulphur) or optionally substituted phenyl, or
$Q^3$ and $Q^4$ together with the carbon atom to which they are attached represent a saturated or unsaturated, unsubstituted or substituted cycle which optionally contains a heteroatom,
L represents an alkanediyl group,
M represents one of the groups below:
CN;

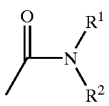

—$CO_2R^2$, —$OR^2$, —$SR^2$, —$COR^3$,

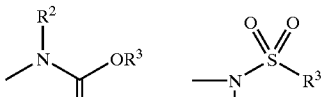

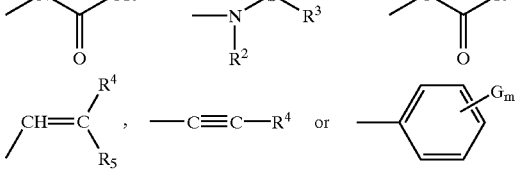

in which
$R^1$ represents hydrogen or alkyl,
$R^2$ represents in each case optionally substituted alkyl, alkenyl, alkinyl, cycloalkyl, alkoxyalkyl, alkylthioalkyl, aryl or aralkyl,
$R^3$ represents optionally substituted alkyl, aryl or aralkyl,
$R^4$ represents hydrogen, halogen, in each case optionally substituted alkyl or phenyl,
$R^5$ represents hydrogen, halogen or optionally substituted alkyl,
G represents halogen, alkyl, alkoxy, halogenoalkyl, halogenoalkoxy, cyano or nitro and
m represents a number 0, 1, 2 or 3.

Depending inter alia on the nature of the substituents, the compounds of the formula (I) can be present as geometrical and/or optical isomers or isomer mixtures of varying composition which if desired, can be separated in a customary manner. The present invention provides both the pure isomers and the isomer mixtures, their preparation and use and compositions comprising them. However, for the sake of simplicity, herein below only compounds of the formula (I) are mentioned, even though this may refer both to the pure compounds and, if appropriate, also to mixtures having varying proportions of isomeric compounds.

Taking into account the meanings (1) to (8) of the group CKE, the following principle structures (I-1) to (I-8) are obtained:

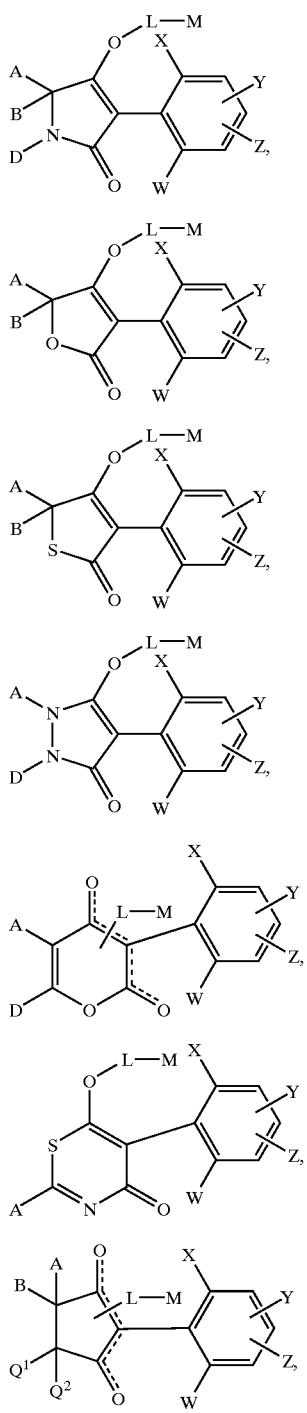

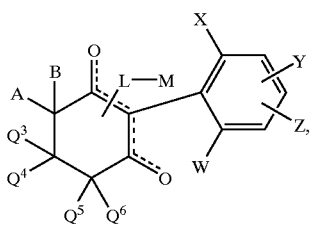

in which

A, B, D, L, M, $Q^1$, $Q^2$, $Q^3$, $Q^4$, $Q^5$, $Q^6$, W, X, Y and Z are as defined above.

Furthermore, it has been found that the novel compounds of the formula (I) have very good pesticidal activity, preferably as arthropodicides, fungicides and herbicides.

Moreover, it has been found that the novel compounds of the formulae (I-1) to (I-8)

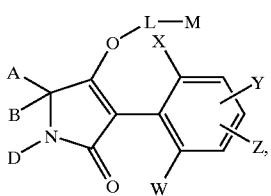

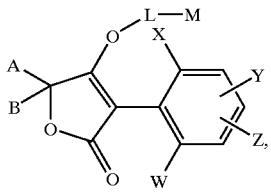

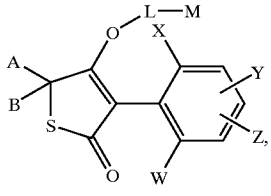

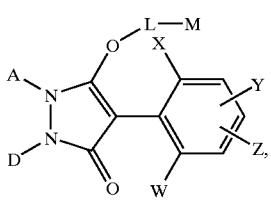

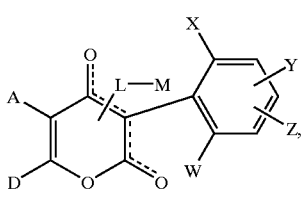

-continued

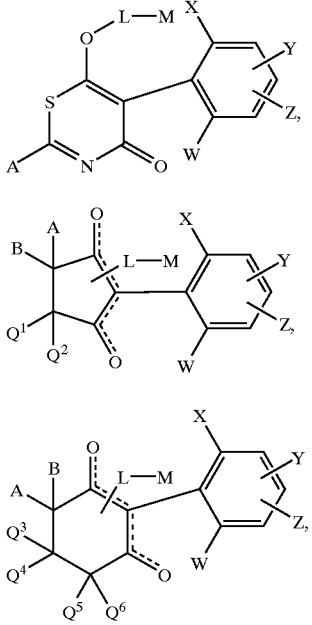

(I-6)

(I-7)

(I-8)

in which

A, B, D, L, M Q$^1$, Q$^2$, Q$^3$, Q$^4$, Q$^5$, Q$^6$, W, X, Y and Z are as defined above, are obtained when (A) compounds of the formulae (II-1) to (II-8)

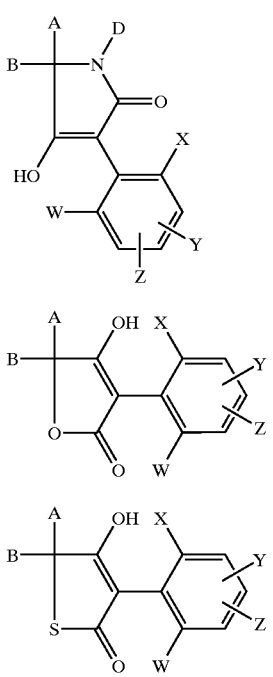

(II-1)

(II-2)

(II-3)

-continued

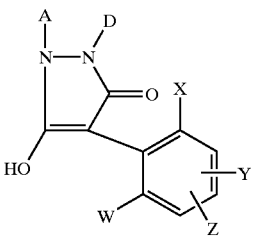

(II-4)

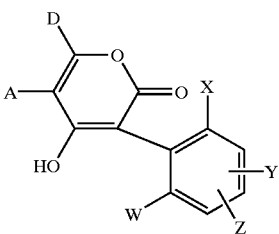

(II-5)

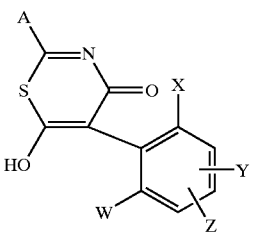

(II-6)

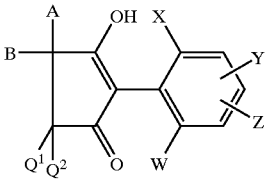

(II-7)

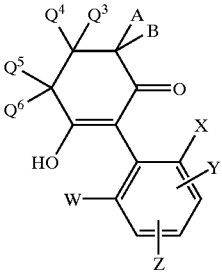

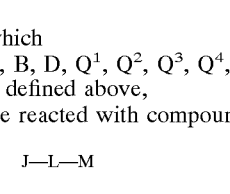

(II-8)

in which
A, B, D, Q$^1$, Q$^2$, Q$^3$, Q$^4$, Q$^5$, Q$^6$, W, X, Y and Z are as defined above,
are reacted with compounds of the formula (III)

$$J—L—M \quad (III)$$

in which
L and M are as defined above and
J represents a leaving group, such as halogen, —O—SO$_2$-halogenoalkyl (for example triflate), —O—SO$_2$-alkyl (for example mesylate) or —O—SO$_2$-aryl (for example tosylate),
in the presence of a diluent and in the presence of a base.

Furthermore, it has been found that the novel compounds of the formula (I) have very good pesticidal activity, preferably as insecticides, acaricides and also as herbicides.

The formula (I) provides a general definition of the compounds according to the invention. Preferred substituents or ranges of the radicals given under the formulae shown above and below are illustrated below:

W preferably represents hydrogen, halogen, $C_1$–$C_6$-alkyl, $C_1$–$C_6$-alkoxy, $C_1$–$C_6$-halogenoalkyl, $C_1$–$C_6$-halogenoalkoxy, nitro or cyano, X preferably represents halogen, $C_1$–$C_6$-alkyl, $C_1$–$C_6$-halogenoalkyl, $C_1$–$C_6$-alkoxy, $C_3$–$C_6$-alkenyloxy, $C_1$–$C_6$-alkylthio, $C_1$–$C_6$-alkylsulphinyl, $C_1$–$C_6$-alkylsulphonyl, $C_1$–$C_6$-halogenoalkoxy, $C_3$–$C_6$-halogenoalkenyloxy, nitro, cyano or in each case optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenoxy phenylthio, benzyloxy or benzylthio, Y preferably represents one of the radicals

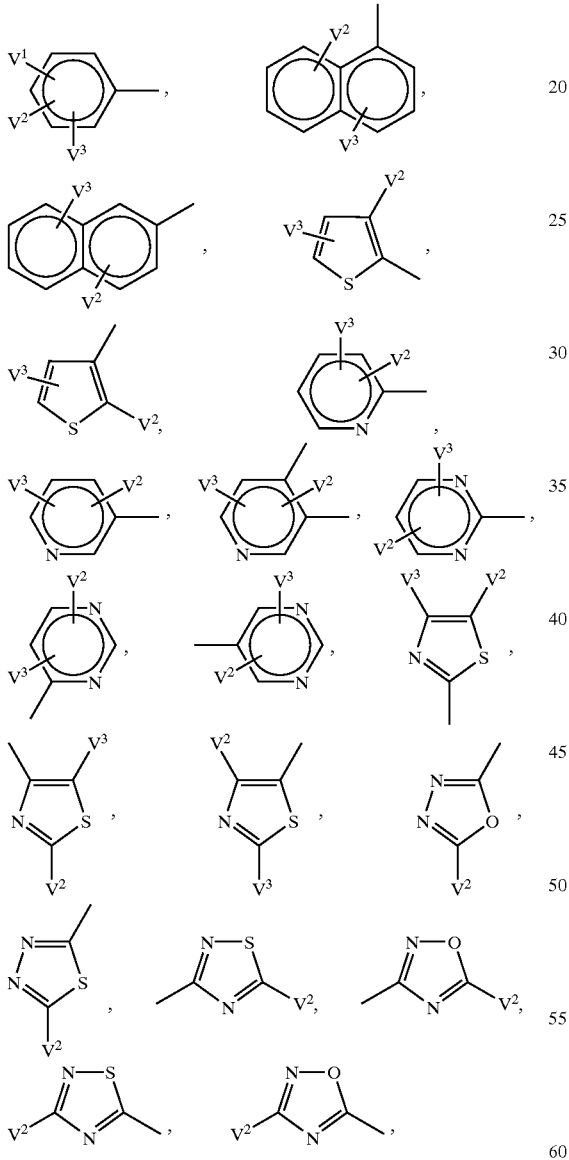

in which

V¹ preferably represents hydrogen, halogen. $C_1$–$C_{12}$-alkyl, $C_1$–$C_6$-alkoxy, $C_1$–$C_4$-halogenoalkyl, $C_1$–$C_4$-halogenoalkoxy, nitro, cyano or phenyl, phenoxy, phenoxy-$C_1$–$C_4$-alkyl, phenyl-$C_1$–$C_4$-alkoxy, phenylthio-$C_1$–$C_4$-alkyl or phenyl-$C_1$–$C_4$-alkylthio, each of which is optionally mono- or polysubstituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano, V² and V³ independently of one another represent hydrogen, halogen, $C_1$–$C_6$-alkyl, $C_1$–$C_6$-alkoxy, $C_1$–$C_4$-halogenoalkyl or $C_1$–$C_4$-halogenoalkoxy, Z preferably represents hydrogen, halogen, $C_1$–$C_6$-alkyl, $C_1$–$C_6$-halogenoalkyl, $C_1$–$C_6$-alkoxy or $C_1$–$C_6$-halogenoalkoxy, CKE preferably represents one of the groups

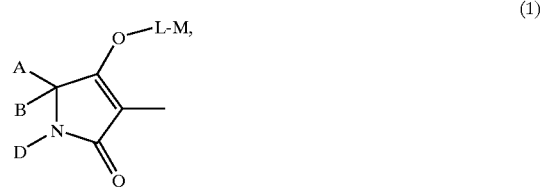 (1)

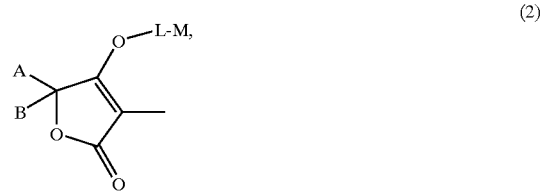 (2)

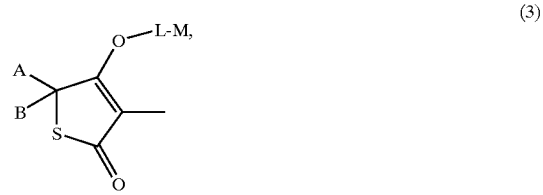 (3)

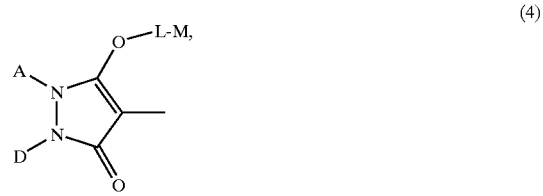 (4)

 (5)

 (6)

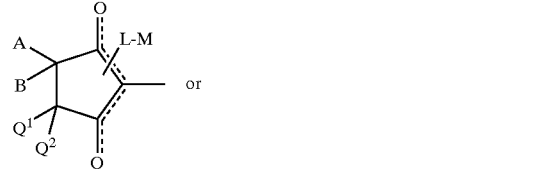 (7)

or

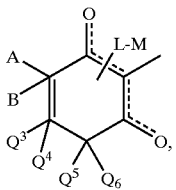
(8)

in which

A preferably represents hydrogen or in each case optionally halogen-substituted $C_1$–$C_{12}$-alkyl, $C_3$–$C_8$-alkenyl, $C_1$–$C_{10}$-alkoxy-$C_1$–$C_8$-alkyl, di-, tri- or tetra-$C_1$–$C_8$-alkoxy-$C_1$–$C_8$-alkyl, $C_1$–$C_{10}$-alkylthio-$C_1$–$C_6$-alkyl, optionally halogen-, $C_1$–$C_6$-alkyl- or $C_1$–$C_6$-alkoxy-substituted $C_3$–$C_8$-cycloalkyl, in which optionally one or two not directly adjacent ring members are replaced by oxygen and/or sulphur, or represents in each case optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano- or nitro-substituted $C_6$- or $C_{10}$-aryl (phenyl or naphthyl), hetaryl having 5 or 6 ring atoms (for example furanyl, pyridyl, imidazolyl, triazolyl, pyrazolyl, pyrimidyl, thiazolyl or thienyl) or $C_6$- or $C_{10}$-aryl-$C_1$–$C_6$-alkyl(phenyl-$C_1$–$C_6$-alkyl or naphthyl-$C_1$–$C_6$-alkyl), B preferably represents hydrogen, $C_1$–$C_{12}$-alkyl or $C_1$–$C_8$-alkoxy-$C_1$–$C_6$-alkyl, or A, B and the carbon atom to which they are attached preferably represent saturated $C_3$–$C_{10}$-cycloalkyl or unsaturated $C_5$–$C_{10}$-cycloalkyl in which optionally one ring member is replaced by oxygen or sulphur and which are optionally mono- or disubstituted by $C_1$–$C_8$-alkyl, $C_3$–$C_{10}$-cycloalkyl, $C_1$–$C_8$-halogenoalkyl, $C_1$–$C_8$-alkoxy, $C_1$–$C_8$-alkylthio, halogen or phenyl, or A, B and the carbon atom to which they are attached preferably represent $C_3$–$C_6$-cycloalkyl which is substituted by an alkylenediyl group which optionally contains one or two not directly adjacent oxygen and/or sulphur atoms or by an alkylenedioxyl or by an alkylenedithiol group which, together with the carbon atom to which they are attached, form a further five- to eight-membered ring, or A, B and the carbon atom to which they are attached preferably represent $C_3$–$C_8$-cycloalkyl or $C_5$–$C_8$-cycloalkenyl in which two substituents together with the carbon atoms to which they are attached represent in each case optionally $C_1$–$C_6$-alkyl-, $C_1$–$C_6$-alkoxy- or halogen-substituted $C_2$–$C_6$-alkanediyl, $C_2$–$C_6$-alkenediyl or $C_4$–$C_6$-alkanedienediyl in which optionally one methylene group is replaced by oxygen or sulphur, D preferably represents hydrogen, in each case optionally halogen-substituted $C_1$–$C_{12}$-alkyl, $C_3$–$C_8$-alkenyl, $C_3$–$C_8$-alkinyl, $C_1$–$C_{10}$-alkoxy-$C_2$–$C_8$-alkyl, poly-$C_1$–$C_8$-alkoxy-$C_2$–$C_8$-alkyl, $C_1$–$C_{10}$-alkylthio-$C_2$–$C_8$-alkyl, optionally halogen-, $C_1$–$C_4$-alkyl-, $C_1$–$C_4$-alkoxy- or $C_1$–$C_4$-halogenoalkyl-substituted $C_3$–$C_8$-cycloalkyl in which optionally one ring member is replaced by oxygen or sulphur or in each case optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano- or nitro-substituted phenyl, hetaryl having 5 or 6 ring atoms (for example furanyl, imidazolyl, pyridyl, thiazolyl, pyrazolyl, pyrimidyl, pyrrolyl, thienyl or triazolyl), phenyl-$C_1$–$C_6$-alkyl or hetaryl-$C_1$–$C_6$-alkyl having 5 or 6 ring atoms (for example furanyl-, imidazolyl-, pyridyl-, thiazolyl-, pyrazolyl-, pyrimidyl-, pyrrolyl-, thienyl- or triazolyl-$C_1$–$C_6$-alkyl), or A and D together preferably represent in each case optionally substituted $C_3$–$C_6$-alkanediyl or $C_3$–$C_6$-alkenediyl in which optionally one methylene group is replaced by oxygen or sulphur, possible substituents being in each case: halogene, hydroxyl, mercapto or in each case optionally halogen-substituted $C_1$–$C_{10}$-alkyl, $C_1$–$C_6$-alkoxy, $C_1$–$C_6$-alkylthio, $C_3$–$C_7$-cycloalkyl, phenyl or benzyloxy, or a further $C_3$–$C_6$-alkanediyl grouping, $C_3$–$C_6$-alkenediyl grouping or a butadienyl grouping, which is optionally substituted by $C_1$–$C_6$-alkyl or in which optionally two adjacent substituents together with the carbon atoms to which they are attached form a further saturated or unsaturated cycle having 5 or 6 ring atoms (in the case of the compound of the formula (I-1), A and D then together with the atoms to which they are attached represent, for example, the groups AD-1 to AD-10 shown further below), which may contain oxygen or sulphur, or which optionally contain one of the groups below

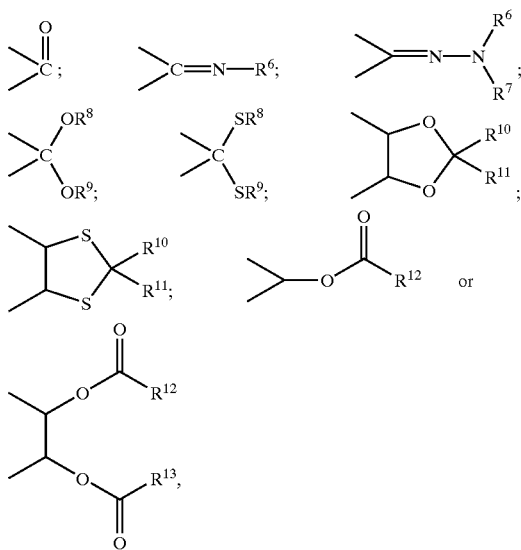

or

A and $Q^1$ together preferably represent $C_3$–$C_6$-alkanediyl or $C_4$–$C_6$-alkenediyl, each of which is optionally mono- or disubstituted by identical or different substituents from the group consisting of halogen, hydroxyl, of $C_1$–$C_{10}$-alkyl, $C_1$–$C_6$-alkoxy, $C_1$–$C_6$-alkylthio, $C_3$–$C_7$-cycloalkyl, each of which is optionally mono- to tri-substituted by identical or different halogens, and benzyloxy or phenyl, each of which is optionally mono- to tri-substituted by identical or different substituents from the groups consisting of halogen, $C_1$–$C_6$-alkyl and $C_1$–$C_6$-alkoxy, which $C_1$–$C_6$-alkanediyl or $C_4$–$C_6$-alkenediyl furthermore optionally contains one of the groups below

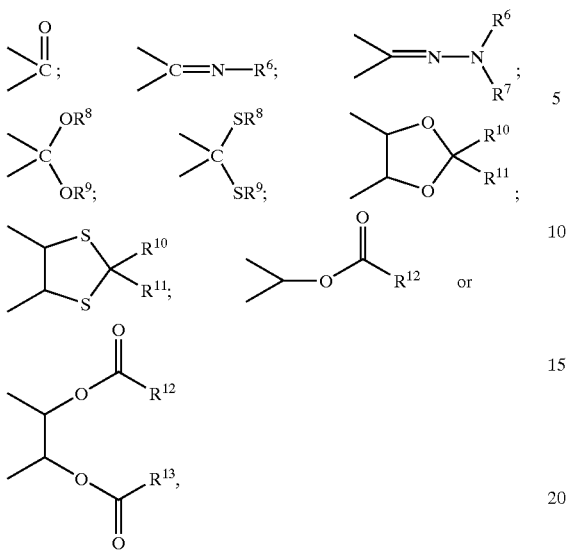

or is bridged by a $C_1$–$C_2$-alkanediyl group or by an oxygen atom or $Q^1$ preferably represents hydrogen or $C_1$–$C_4$-alkyl, $Q^2$, $Q^4$, $Q^5$ and $Q^6$ independently of one another preferably represent hydrogen or $C_1$–$C_4$-alkyl, $Q^3$ represents hydrogen, $C_1$–$C_6$-alkyl, $C_1$–$C_6$-alkoxy-$C_1$–$C_2$-alkyl, $C_1$–$C_6$-alkylthio-$C_1$–$C_2$-alkyl, optionally $C_1$–$C_4$-alkyl- or $C_1$–$C_4$-alkoxy-substituted $C_3$–$C_8$-cycloalkyl, in which optionally one methylene group is replaced by oxygen or sulphur, or optionally halogen-, $C_1$–$C_4$-alkyl-, $C_1$–$C_4$-alkoxy-, $C_1$–$C_2$-halogenoalkyl-, $C_1$–$C_2$-halogenoalkoxy-, cyano- or nitro-substituted phenyl, or $Q^3$ and $Q^4$ together with the carbon atom to which they are attached preferably represent optionally $C_1$–$C_4$-alkyl-, $C_1$–$C_4$-alkoxy- or $C_1$–$C_2$-halogenoalkyl-substituted $C_3$–$C_7$-cycloalkyl in which optionally one ring member is replaced by oxygen or sulphur, L preferably represents an alkanediyl group having 1 to 6 carbon atoms, M preferably represents one of the groupings below:
CN;

—$CO_2R^2$, —$OR^2$, —$SR^2$, —$COR^3$,

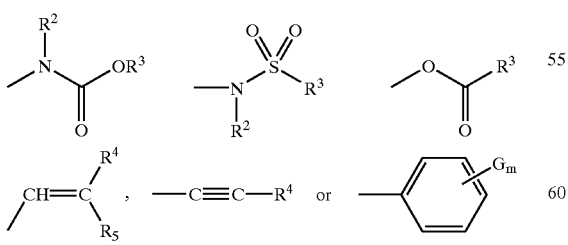

$R^1$ preferably represents hydrogen or $C_1$–$C_{12}$-alkyl, $R^2$ preferably represents in each case optionally halogen-substituted $C_1$–$C_{12}$-alkyl, $C_3$–$C_8$-alkenyl, $C_3$–$C_8$-alkinyl, $C_3$–$C_8$-cycloalkyl, $C_1$–$C_8$-alkoxy-$C_2$–$C_8$-alkyl, $C_1$–$C_8$-alkylthio-$C_1$–$C_8$-alkyl, represents in each case optionally halogen-, nitro-, cyano-, $C_1$–$C_6$-alkoxy-, $C_1$–$C_6$-halogenoalkoxy-, $C_1$–$C_6$-alkylthio-, $C_1$–$C_6$-halogenoalkylthio-, $C_1$–$C_6$-alkyl- or $C_1$–$C_6$-halogenoalkyl-substituted phenyl or benzyl, $R^3$ preferably represents optionally halogen-substituted $C_1$–$C_{12}$-alkyl or represents in each case optionally halogen-, $C_1$–$C_6$-alkyl-, $C_1$–$C_6$-halogenoalkyl-, $C_1$–$C_6$-alkoxy- or $C_1$–$C_6$-halogenoalkoxy-substituted phenyl or benzyl, $R^4$ preferably represents hydrogen, halogen, optionally halogen-substituted $C_1$–$C_6$-alkyl or in each case optionally halogen-, $C_1$–$C_6$-alkyl-, $C_1$–$C_6$-alkoxyl-, $C_1$–$C_4$-halogenoalkyl-, $C_1$–$C_4$-halogenoalkoxy-, cyano- or nitro-substituted phenyl, $R^5$ preferably represents hydrogen, halogen or optionally halogen-substituted $C_1$–$C_6$-alkyl, G preferably represents halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, m preferably represents a number 0, 1, 2 or 3, $R^6$ preferably represents hydrogen, represents in each case optionally halogen-substituted $C_1$–$C_8$-alkyl or $C_1$–$C_8$-alkoxy, represents optionally halogen-, $C_1$–$C_4$-alkyl- or $C_1$–$C_4$-alkoxy-substituted $C_1$–$C_8$-cycloalkyl, in which optionally one methylene group is replaced by oxygen or sulphur, or represents in each case optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenyl-$C_1$–$C_4$-alkyl or phenyl-$C_1$–$C_4$-alkoxy, $R^7$ preferably represents hydrogen or $C_1$–$C_8$-alkyl, or $R^6$ and $R^7$ together preferably represent $C_4$–$C_6$-alkanediyl, $R^8$ and $R^9$ are identical or different and preferably represent $C_1$–$C_6$-alkyl, or $R^8$ and $R^9$ together preferably represent a $C_2$–$C_4$-alkanediyl radical which is optionally substituted by $C_1$–$C_6$-alkyl, $C_1$–$C_6$-halogenoalkyl or by optionally halogen-, $C_1$–$C_6$-alkyl-, $C_1$–$C_4$-halogenoalkyl-, $C_1$–$C_6$-alkoxy-, $C_1$–$C_4$-halogenoalkoxy-, nitro- or cyano-substituted phenyl, $R^{10}$ and $R^{11}$ independently of one another preferably represent hydrogen, represent optionally halogen-substituted $C_1$–$C_8$-alkyl or represent optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, or $R^{10}$ and $R^{11}$ together with the carbon atom to which they are attached preferably represent a carbonyl group or represent optionally halogen-, $C_1$–$C_4$-alkyl- or $C_1$–$C_4$-alkoxy-substituted $C_5$–$C_7$-cycloalkyl in which optionally one methylene group is replaced by oxygen or sulphur, $R^{12}$ and $R^{13}$ independently of one another preferably represent $C_1$–$C_{10}$-alkyl, $C_2$–$C_{10}$- alkenyl, $C_1-C_{10}$-alkoxy, $C_1-C_{10}$-alkylamino, $C_3-C_{10}$-alkenylamino, di-$(C_1-C_{10}$-alkyl)amino or di-$(C_3-C_{10}$-alkenyl)amino.

In the radical definitions mentioned as being preferred, halogen, also as substituent, such as, for example, in halogenoalkyl, represents fluorine, chlorine, bromine and iodine, in particular fluorine and chlorine, W particularly preferably represents hydrogen, fluorine, chlorine, bromine, $C_1-C_4$-alkyl, $C_1-C_4$-alkoxy, $C_1-C_4$-halogenoalkyl, $C_1-C_4$-halogenoalkoxy, nitro or cyano, X particularly preferably represents fluorine, chlorine, bromine, $C_1-C_4$-alkyl, $C_1-C_4$-alkoxy, $C_3-C_4$-alkenyloxy, $C_1-C_4$-halogenoalkyl, $C_1-C_4$-halogenoalkoxy, $C_3-C_4$-halogenoalkenyloxy, nitro or cyano, Y particularly preferably represents one of the radicals

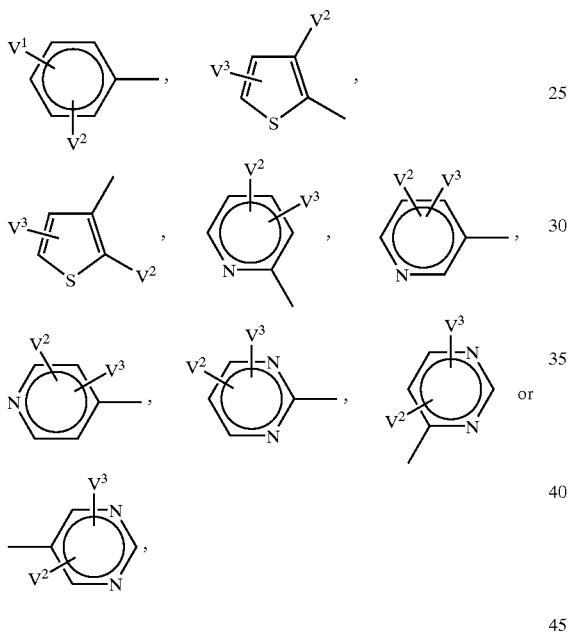

in which

V¹ particularly preferably represents hydrogen, fluorine, chlorine, bromine, $C_1-C_6$-alkyl, $C_1-C_4$-alkoxy, $C_1-C_2$-halogenoalkyl, $C_1-C_2$-halogenoalkoxy, nitro, cyano or represents phenyl, phenoxy, phenoxy-$C_1-C_2$-alkyl, phenyl-$C_1-C_2$-alkoxy, phenylthio-$C_1-C_2$-alkyl or phenyl-$C_1-C_2$-alkylthio, each of which is optionally mono- or disubstituted by fluorine, chlorine, bromine, $C_1-C_4$-alkyl, $C_1-C_4$-alkoxy, $C_1-C_2$-halogenoalkyl, $C_1-C_2$-halogenoalkoxy, nitro or cyano, V² and V³ independently of one another particularly preferably represent hydrogen, fluorine, chlorine, bromine, $C_1-C_4$-alkyl, $C_1-C_4$-alkoxy, $C_1-C_2$-halogenoalkyl or $C_1-C_2$-halogenoalkoxy, Z particularly preferably represents hydrogen, fluorine, chlorine, bromine, $C_1-C_4$-alkyl, $C_1-C_4$-halogenoalkyl, $C_1-C_4$-alkoxy or $C_1-C_4$-halogenoalkoxy, CKE particularly preferably represents one of the groups

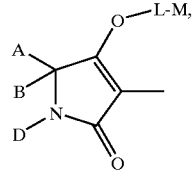 (1)

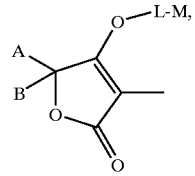 (2)

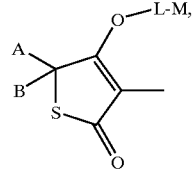 (3)

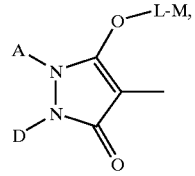 (4)

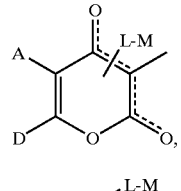 (5)

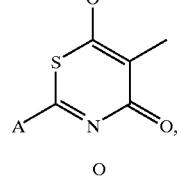 (6)

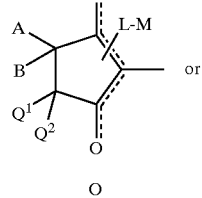 (7)

or

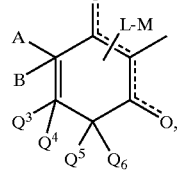 (8)

A particularly preferably represents hydrogen, in each case optionally fluorine- or chlorine-substituted $C_1-C_{10}$-alkyl, $C_1-C_8$-alkoxy-$C_1-C_6$-alkyl, optionally fluorine-, chlorine-, $C_1-C_4$-alkyl- or $C_1-C_4$- alkoxy-substituted $C_3-C_7$-cycloalkyl, in which optionally one ring member is replaced by oxygen or sulphur, or (but not in the case of the compounds of the formulae (I-5), (I-7) and (I-8)) in each case optionally fluorine-, chlorine-, bromine-, $C_1-C_4$-alkyl-, $C_1-C_4$-halogenoalkyl-, $C_1-C_4$-alkoxy-, cyano-, nitro- or $C_1-C_4$-halogenoalkoxy-substituted phenyl, furanyl, pyridyl, imidazolyl, triazolyl, pyrazolyl, pyrimidyl, thiazolyl, thienyl or phenyl-$C_1-C_4$-alkyl, B particularly preferably represents hydrogen or $C_1-C_6$-alkyl, or A, B and the carbon atom to which they are attached particularly preferably represent saturated or unsaturated $C_5-C_7$-cycloalkyl in which optionally one ring member is replaced by oxygen or sulphur and which is optionally monosubstituted by $C_1-C_6$-alkyl, $C_5-C_8$-cycloalkyl, $C_1-C_3$-halogenoalkyl, $C_1-C_6$-alkoxy, fluorine, chlorine or phenyl, or A, B and the carbon atom to which they are attached particularly preferably represent $C_5-C_6$-cycloalkyl which is substituted by an alkylenediyl group which optionally contains one or two not directly adjacent oxygen or sulphur atoms or by an alkylenedioxyl or an alkylenedithiol group which, together with the carbon atom to which they are attached, form a further 5- or 6-membered ring, or A, B and the carbon atom to which they are attached particularly preferably represent $C_3-C_6$-cycloalkyl or $C_5-C_6$-cycloalkenyl in which two substituents together with the carbon atoms to which they are attached represent in each case optionally $C_1-C_5$-alkyl-, $C_1-C_5$-alkoxy-, fluorine-, chlorine- or bromine-substituted $C_2-C_4$-alkanediyl, $C_2-C_4$-alkenediyl, in which optionally one methylene group is replaced by oxygen or sulphur, or butyldienediyl, D particularly preferably represents hydrogen, represents in each case optionally fluorine- or chlorine-substituted $C_1-C_{10}$-alkyl, $C_3-C_6$-alkenyl, $C_1-C_8$-alkoxy-$C_2-C_6$-alkyl or $C_1-C_8$-alkylthio-$C_2-C_6$-alkyl, represents optionally fluorine-, chlorine- $C_1-C_4$-alkyl-, $C_1-C_4$-alkoxy- or $C_1-C_2$-halogenoalkyl-substituted $C_3-C_7$-cycloalkyl, in which optionally one methylene group is replaced by oxygen or sulphur, or (but not in the case of the compounds of the formulae (I-1) and (I-4)) represents in each case optionally fluorine-, chlorine, bromine-, $C_1-C_4$-alkyl-, $C_1-C_4$-halogenoalkyl-, $C_1-C_4$-alkoxy- or $C_1-C_4$-halogenoalkoxy-substituted phenyl, furanyl, imidazolyl, pyridyl, thiazolyl, pyrazolyl, pyrimidyl, pyrrolyl, thienyl, triazolyl or phenyl-$C_1-C_4$-alkyl, or A and D together particularly preferably represent optionally substituted $C_3-C_5$-alkanediyl in which one methylene group may be replaced by a carbonyl group, oxygen or sulphur, possible substituents being hydroxyl, $C_1-C_6$-alkyl and $C_1-C_4$-alkoxy, or A and D (in the case of the compounds of the formula (I-1)) together with the atoms to which they are attached represent one of the groups AD-1 to AD-10:

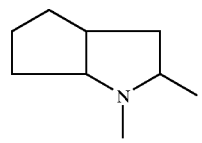
AD-1

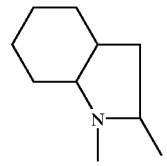
AD-2

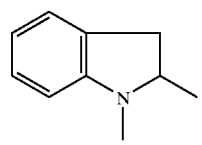
AD-3

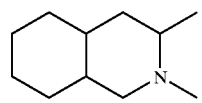
AD-4

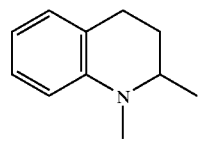
AD-5

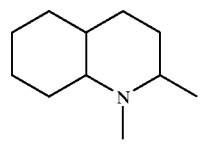
AD-6

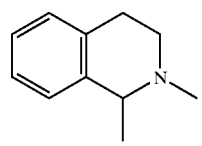
AD-7

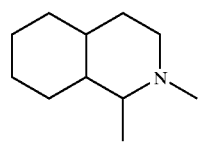
AD-8

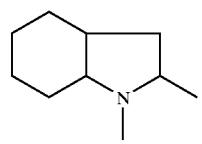
AD-9

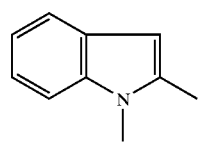
AD-10 or

A and $Q^1$ together particularly preferably represent $C_3-C_4$-alkanediyl or $C_3-C_4$-alkenediyl, each of which is optionally mono- or disubstituted by identical or different substituents from the group consisting of fluorine, chlorine, hydroxyl and $C_1-C_8$-alkyl and $C_1$–$C_4$-alkoxy, each of which may optionally be mono- to trisubstituted by fluorine, or $Q^1$ particularly preferably represents hydrogen, $Q^2$ particularly preferably represents hydrogen, $Q^4$, $Q^5$ and $Q^6$ independently of one another particularly preferably represent hydrogen or $C_1$–$C_3$-alkyl, $Q^3$ particularly preferably represents hydrogen, $C_1$–$C_4$-alkyl, $C_1$–$C_4$-alkoxy-$C_1$–$C_2$-alkyl, $C_1$–$C_4$-alkylthio-$C_1$–$C_2$-alkyl or optionally methyl- or methoxy-substituted $C_3$–$C_6$-cycloalkyl in which optionally one methylene group is replaced by oxygen or sulphur, or $Q^3$ and $Q^4$ together with the carbon to which they are attached particularly preferably represent optionally $C_1$–$C_4$-alkyl- or $C_1$–$C_4$-alkoxy-substituted saturated $C_5$–$C_6$-cycloalkyl in which optionally one ring member is replaced by oxygen or sulphur, L particularly preferably represents an alkanediyl group having 1 to 4 carbon atoms, M particularly preferably represents one of the groupings below:

CN;

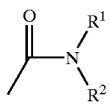

—CO$_2$R$^2$, —OR$^2$, —SR$^2$, —COR$^3$,

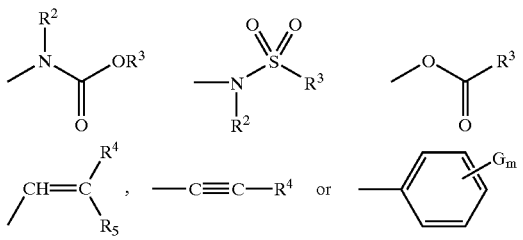

in which

R$^1$ particularly preferably represents hydrogen or $C_1$–$C_{10}$-alkyl,

R$^2$ particularly preferably represents in each case optionally fluorine-, chlorine-, bromine-substituted $C_1$–$C_{10}$-alkyl, $C_3$–$C_6$-alkenyl, $C_3$–$C_6$-alkinyl, $C_3$–$C_8$-cycloalkyl, $C_1$–$C_6$-alkoxy-$C_2$–$C_6$-alkyl, $C_1$–$C_6$-alkylthio-$C_1$–$C_6$-alkyl, represents in each case optionally fluorine-, chlorine-, bromine-, nitro-, cyano-, $C_1$–$C_4$-alkylthio-, $C_1$–$C_6$-alkoxy-, $C_1$–$C_6$-halogenoalkoxy-, $C_1$–$C_4$-halogenoalkylthio-, $C_1$–$C_6$-alkyl- or $C_1$–$C_6$-halogenoalkyl-substituted phenyl or benzyl, R$^3$ particularly preferably represents optionally fluorine-, chlorine-, bromine-substituted $C_1$–$C_{10}$-alkyl or represents in each case optionally fluorine-, chlorine-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl or benzyl, R$^4$ particularly preferably represents hydrogen, fluorine, chlorine, bromine, optionally fluorine- or chlorine-substituted $C_1$–$C_6$-alkyl or optionally fluorine-, chlorine-, bromine-, $C_1$–$C_4$-alkyl-, $C_1$–$C_4$-alkoxy-, $C_1$–$C_6$-halogenoalkyl-, $C_1$–$C_6$-halogenoalkoxy, cyano- or nitro-substituted phenyl, R$^5$ particularly preferably represents hydrogen, fluorine, chlorine, bromine or optionally fluorine- or chlorine-substituted $C_1$–$C_4$-alkyl, G particularly preferably represents fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, m particularly preferably represents a number 0, 1 or 2.

In the radical definitions mentioned as being particularly preferred, halogen, also as substituent, such as, for example, in halogenoalkyl, represents fluorine, chlorine, bromine and iodine, in particular fluorine, chlorine and bromine, very particularly preferably fluorine or chlorine, W very particularly preferably represents hydrogen, chlorine, fluorine, methyl, ethyl, methoxy, ethoxy (especially hydrogen, methyl, ethyl or chlorine), X very particularly preferably represents fluorine, chlorine, methyl, ethyl, n-propyl, isopropyl, methoxy, ethoxy, n-propoxy, isopropoxy, trifluoromethyl, difluoromethoxy, trifluoromethoxy, nitro or cyano (especially fluorine, chlorine, methyl, ethyl, n-propyl or isopropyl), Y very particularly preferably represents one of the radicals

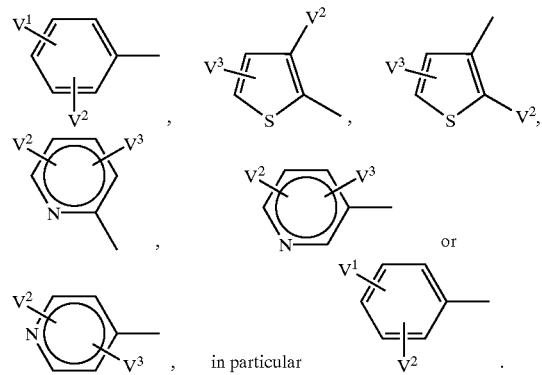

in which

V$^1$ very particularly preferably represents hydrogen, fluorine, chlorine, bromine, methyl, ethyl, n-propyl, isopropyl, n-butyl, isobutyl, tert-butyl, methoxy, ethoxy, n-propoxy, isopropoxy, trifluoromethyl, trifluoromethoxy, nitro, cyano or phenyl, V$^2$ and V$^3$ independently of one another very particularly preferably represent hydrogen, fluorine, chlorine, methyl, ethyl, n-propyl, isopropyl, methoxy, ethoxy, trifluoromethyl or trifluoromethoxy, Z very particularly preferably represents hydrogen, fluorine, chlorine, methyl or methoxy (especially hydrogen or methyl), CKE very particularly preferably represents one of the groups

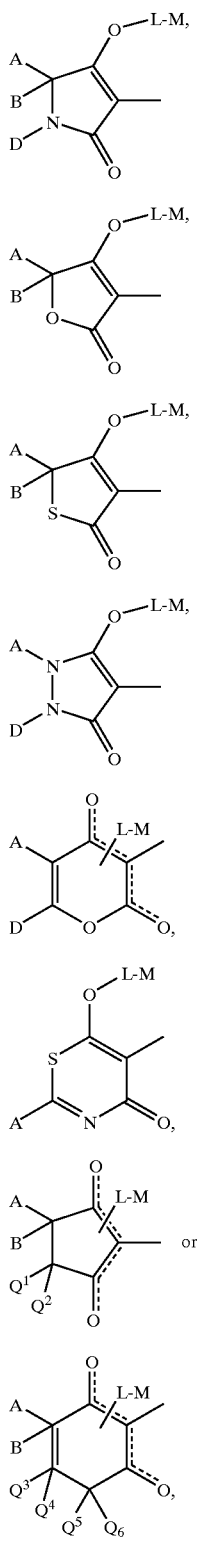

(1)
(2)
(3)
(4)
(5)
(6)
(7)
(8)

in which

A very particularly preferably represents hydrogen, in each case optionally fluorine-substituted $C_1$–$C_8$-alkyl or $C_1$–$C_6$-alkoxy-$C_1$–$C_4$-alkyl, optionally fluorine-, methyl-, ethyl- or methoxy-substituted $C_3$–$C_6$-cycloalkyl, in which optionally one ring member is replaced by oxygen or sulphur, or (but not in the case of the compounds of formulae (I-5), (I-7) and (I-8)) represents in each case optionally fluorine-, chlorine-, bromine-, methyl-, ethyl-, n-propyl-, isopropyl-, methoxy-, ethoxy-, trifluoromethyl-, trifluoromethoxy-, cyano- or nitro-substituted phenyl or benzyl, B very particularly preferably represents hydrogen or $C_1$–$C_4$-alkyl, or A, B and the carbon atom to which they are attached very particularly preferably represent saturated $C_5$–$C_6$-cycloalkyl in which optionally one ring member is replaced by oxygen or sulphur and which is optionally monosubstituted by methyl, ethyl, n-propyl, isopropyl, butyl, isobutyl, sec-butyl, tert-butyl, trifluoromethyl, methoxy, ethoxy, n-propoxy, isopropoxy, n-butoxy, isobutoxy, sec-butoxy, tert-butoxy, fluorine or chlorine, or A, B and the carbon atom to which they are attached very particularly preferably represent $C_5$–$C_6$-cycloalkyl in which two substituents together with the carbon atoms to which they are attached represent $C_2$–$C_4$-alkanediyl or $C_2$–$C_4$-alkenediyl, in which in each case, optionally one methylene group is replaced by oxygen or sulphur, or butadienediyl, D very particularly preferably represents hydrogen, represents in each case optionally fluorine- or chlorine-substituted $C_1$–$C_8$-alkyl, $C_3$–$C_4$-alkenyl, $C_1$–$C_6$-alkoxy-$C_2$–$C_4$-alkyl, $C_1$–$C_4$-alkylthio-$C_2$–$C_4$-alkyl or $C_3$–$C_6$-cycloalkyl, in which optionally one methylene group is replaced by oxygen or sulphur, or (but not in the case of the compounds of formulae (I-1) and (I-4)) represents in each case optionally fluorine-, chlorine-, methyl-, ethyl-, n-propyl-, isopropyl-, methoxy-, ethoxy-, trifluoromethyl- or trifluoromethoxy-substituted phenyl, furanyl, pyridyl, thienyl or benzyl (in compounds of the formula (I-1) especially hydrogen), or A and D together very particularly preferably represent optionally substituted $C_3$–$C_4$-alkanediyl in which optionally one carbon atom is replaced by sulphur and which is optionally substituted by hydroxyl, methyl, ethyl, methoxy or ethoxy, or A and D (in the case of the compounds of the formula (I-1)) together with the atoms to which they are attached very particularly preferably represent one of the groups AD below:

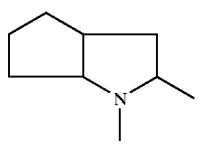

AD-1

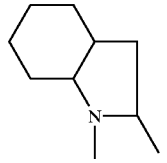

AD-2

25
-continued

AD-3

[structure: N-methyl-2-methylindoline]

AD-4

[structure: decahydroisoquinoline with N-methyl and 3-methyl]

AD-6

[structure: decahydroquinoline with N-methyl and 2-methyl]

AD-8

[structure: decahydroisoquinoline with N-methyl and 1-methyl]

AD-10

[structure: N-methyl-2-methylindole]

A and $Q^1$ together very particularly preferably represent butenediyl or $C_3$–$C_4$-alkanediyl, optionally mono- or disubstituted by fluorine, hydroxyl, methyl or methoxy, or $Q^1$ very particularly preferably represents hydrogen, $Q^2$ very particularly preferably represents hydrogen, $Q^4$, $Q^5$ and $Q^6$ independently of one another very particularly preferably represent hydrogen, methyl or ethyl, $Q^3$ very particularly preferably represents hydrogen, methyl, ethyl or $C_3$–$C_6$-cycloalkyl, in which optionally one methylene group is replaced by oxygen or sulphur (especially hydrogen, methyl or ethyl), or $Q^3$ and $Q^4$ together with the carbon to which they are attached very particularly preferably represent optionally methyl- or methoxy-substituted saturated $C_5$–$C_6$-cycloalkyl in which optionally one ring member is replaced by oxygen or sulphur, L very particularly preferably represents one of the groupings below:
—CH$_2$—,

[structure: CH(CH$_3$)$_2$ group],  [structure: C(CH$_3$)$_3$ group],

CH$_2$—CH$_2$,

[structure: CH(CH$_3$)CH$_2$ group],

M very particularly preferably represents one of the groupings below:

26

CN;

[structure: C(=O)N(R$^1$)(R$^2$) group]

—CO$_2$R$^2$, —OR$^2$, —SR$^2$, —COR$^3$,

[structure: N(R$^2$)C(=O)OR$^3$], [structure: sulfonamide N(R$^2$)S(=O)$_2$R$^3$], [structure: OC(=O)R$^3$]

[structure: CH=C(R$^4$)(R$_5$)], —C≡C—R$^4$ or

[structure: phenyl with G$_m$ substituents]

in which $R^1$ very particularly preferably represents hydrogen or $C_1$–$C_6$-alkyl, $R^2$ very particularly preferably represents in each case optionally fluorine-, chlorine-, bromine-substituted $C_1$–$C_8$-alkyl, $C_3$–$C_4$-alkenyl, $C_3$–$C_4$-alkinyl, cyclopropyl, cyclopentyl, cyclohexyl, $C_1$–$C_6$-alkoxy-$C_2$–$C_4$-alkyl, $C_1$–$C_6$-alkylthio-$C_2$–$C_4$-alkyl, represents in each case optionally fluorine-, chlorine-, bromine-, nitro-, cyano-, methylthio-, ethylthio-, methoxy-, ethoxy-, trifluoromethylthio-, trifluoromethoxy-, methyl-, ethyl-, trifluoromethyl-substituted phenyl or benzyl, $R^3$ very particularly preferably represents optionally fluorine-, chlorine-, bromine-substituted $C_1$–$C_8$-alkyl or in each case optionally fluorine-, chlorine-, $C_1$–$C_2$-alkyl-, trifluoromethyl-, $C_1$–$C_2$-alkoxy- or trifluoromethoxy-substituted phenyl or benzyl, $R^4$ very particularly preferably represents hydrogen, fluorine, chlorine, optionally fluorine- or chlorine-substituted $C_1$–$C_4$-alkyl or optionally fluorine-, chlorine-, methyl-, ethyl-, methoxy-, ethoxy-, trifluoromethyl-, difluoromethoxy-, trifluoromethoxy-, cyano- or nitro-substituted phenyl, $R^5$ very particularly preferably represents hydrogen, fluorine, chlorine or in each case optionally fluorine- or chlorine-substituted methyl, ethyl, propyl or isopropyl, G very particularly preferably represents fluorine, chlorine, methyl, ethyl, propyl, isopropyl, methoxy, ethoxy, propoxy, isopropoxy, trifluoromethyl, difluoromethoxy, trifluoromethoxy, cyano or nitro, m very particularly preferably represents a number from 0 to 2.

W most preferably represents hydrogen, chlorine, fluorine, methyl, ethyl, methoxy, ethoxy (especially hydrogen, methyl, ethyl or chlorine), X most preferably represents fluorine, chlorine, methyl, ethyl, n-propyl, isopropyl, methoxy, ethoxy, n-propoxy, isopropoxy, trifluoromethyl, difluoro-difluoromethoxy, trifluoromethoxy, nitro or cyano (especially chlorine, methyl, ethyl, n-propyl or isopropyl), Y most preferably represents one of the radicals

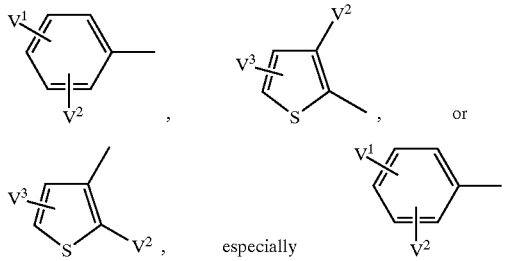, especially.

in which

V¹ most preferably represents hydrogen, fluorine, chlorine, methyl, ethyl, n-propyl, isopropyl, n-butyl, isobutyl, tert-butyl, methoxy, ethoxy, n-propoxy, isopropoxy, trifluoromethyl, trifluoromethoxy, nitro, cyano or phenyl, V² most preferably represents hydrogen, fluorine, chlorine, methyl, methoxy, trifluoromethyl or trifluoromethoxy, V³ most preferably represents hydrogen, methyl or chlorine, Z most preferably represents hydrogen, fluorine, chlorine, methyl or methoxy, especially hydrogen or methyl, CKE most preferably represents one of the groups

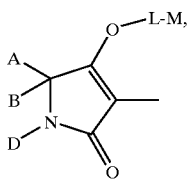 (1)

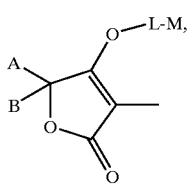 (2)

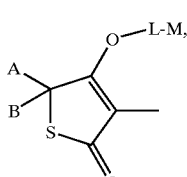 (3)

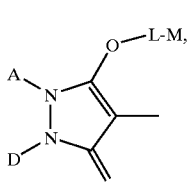 (4)

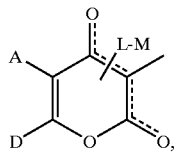 (5)

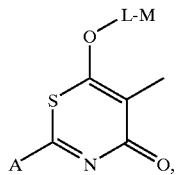 (6)

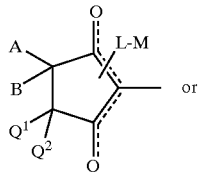 or (7)

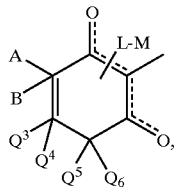 (8)

in which

A most preferably represents hydrogen, in each case optionally fluorine-substituted $C_1$–$C_8$-alkyl or $C_1$–$C_6$-alkoxy-$C_1$–$C_4$-alkyl, optionally fluorine-, methyl- or methoxy-substituted $C_3$–$C_6$-cycloalkyl, in which optionally one ring member is replaced by oxygen or sulphur, or (but not in the case of the compounds of the formulae (I-5), (I-7) and (I-8)) represents in each case optionally fluorine-, chlorine-, bromine-, methyl-, methoxy-, trifluoromethyl- or trifluoromethoxy-substituted phenyl or benzyl, B most preferably represents hydrogen or $C_1$–$C_4$-alkyl, or A, B and the carbon atom to which they are attached most preferably represent saturated $C_5$–$C_6$-cycloalkyl in which optionally one ring member is replaced by oxygen or sulphur and which is optionally monosubstituted by methyl, ethyl, n-propyl, isopropyl, trifluoromethyl, methoxy, ethoxy, n-propoxy, isopropoxy, n-butoxy or isobutoxy, or A, B and the carbon atom to which they are attached most preferably represent $C_5$–$C_6$-cycloalkyl in which two substituents together with the carbon atoms to which they attached represent $C_2$–$C_4$-alkanediyl or $C_2$–$C_4$-alkenediyl in which in each case optionally one methylene group is replaced by oxygen or sulphur, or butadienediyl, D most preferably represents hydrogen, represents in each case optionally fluorine- or chlorine-substituted $C_1$–$C_6$-alkyl, $C_3$–$C_4$-alkenyl, $C_1$–$C_4$-alkoxy-$C_2$–$C_4$-alkyl, $C_1$–$C_4$-alkylthio-$C_2$–$C_4$-alkyl or $C_3$–$C_6$-cycloalkyl, in which optionally one methylene group is replaced by oxygen or sulphur, or (but not in the case of the compounds of the formulae (I-1) and (I-4)), represents in each case optionally fluorine-, chlorine-, methyl-, methoxy-, trifluoromethyl- or trifluoromethoxy-substituted phenyl, pyridyl or benzyl, or A and D together most preferably represent optionally substituted $C_3$–$C_4$-alkanediyl in which optionally one carbon atom is replaced by sulphur and which is optionally substituted by methyl or methoxy, A and $Q^1$ together most preferably represent butenediyl or $C_3$–$C_4$-alkanediyl, optionally mono- or disubstituted by methyl or methoxy, or $Q^1$ most preferably represents hydrogen, $Q^2$ most preferably represents hydrogen, $Q^4$, $Q^5$ and $Q^6$ independently of one another most preferably represent hydrogen, methyl or ethyl, $Q^3$ most preferably represents hydrogen, methyl, ethyl or $C_3$–$C_6$-cycloalkyl in which optionally one methylene group is replaced by oxygen or sulphur (especially hydrogen, methyl or ethyl), or $Q^3$ and $Q^4$ together with the carbon to which they are attached most preferably represent optionally methyl- or methoxy-substituted saturated $C_5$–$C_6$-cycloalkyl in which optionally one ring member is replaced by oxygen or sulphur, L most preferably represents one of the groupings below:

—CH$_2$—,

—CH$_2$—CH$_2$,

M most preferably represents one of the groupings below:

CN;

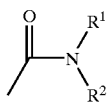

—CO$_2$R$^2$, —OR$^2$, —SR$^2$, —COR$^3$,

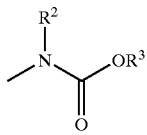 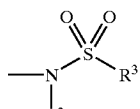

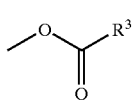 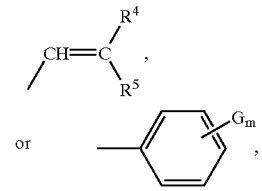

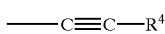 or 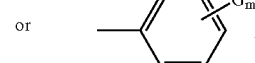

in which $R^1$ most preferably represents hydrogen or $C_1$–$C_4$-alkyl, $R^2$ most preferably represents in each case optionally fluorine-substituted $C_1$–$C_4$-alkyl, $C_1$–$C_6$-alkenyl, $C_1$–$C_4$-alkinyl, cyclopropyl, cyclopentyl, cyclohexyl, $C_1$–$C_4$-alkoxy-$C_1$–$C_4$-alkyl, represents in each case optionally fluorine-, chlorine-, bromine-, nitro-, cyano-, methylthio-, ethylthio-, methoxy-, ethoxy-, trifluoromethylthio, trifluoromethoxy-, methyl-, ethyl-, trifluoromethyl-substituted phenyl or benzyl, $R^3$ most preferably represents optionally fluorine-substituted $C_1$–$C_4$-alkyl or optionally fluorine-, chlorine-, methyl-, trifluoromethyl-, methoxy- or trifluoromethoxy-substituted phenyl, $R^4$ most preferably represents hydrogen, fluorine, chlorine, optionally fluorine-substituted $C_1$–$C_4$-alkyl or optionally fluorine-, chlorine-, methyl-, ethyl-, methoxy-, ethoxy-, trifluoromethyl-, difluoromethoxy-, trifluoromethoxy-, cyano- or nitro-substituted phenyl, $R^5$ most preferably represents hydrogen, fluorine, chlorine or optionally fluorine-substituted methyl, G most preferably represents fluorine, chlorine, methyl, methoxy, trifluoromethyl, difluoromethoxy, trifluoromethoxy, cyano or nitro, m most preferably represents a number from 0 to 1.

The abovementioned general or preferred radical definitions or illustrations can be combined with one another as desired, i.e. including combinations between the respective ranges and preferred ranges. They apply both to the end products and, correspondingly, to the precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Most preference is given to compounds of the formula (I), in which G is hydrogen.

Saturated or unsaturated hydrocarbon radicals, such as alkyl or alkenyl, can in each case to straight-chain or branched as far as this is possible, including in combination with heteroatoms, such as, for example, an alkoxy.

Unless indicated otherwise, optionally substituted radicals can be mono- or substituted where, in the case of polysubstitution, the substituents can be identical or different.

In addition to the compounds mentioned in the Preparation Examples, the following compounds of the formula (I-1) may be specifically mentioned:

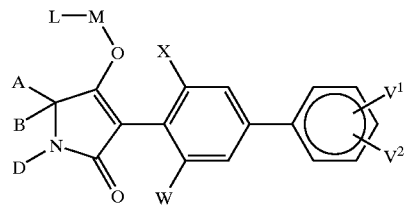

TABLE 1

L—M = CH$_2$—O—C$_2$H$_5$, X = CH$_3$, W = CH$_3$, V$^1$ = H, V$^2$ = H.

| A | B | D |
|---|---|---|
| CH$_3$ | H | H |
| C$_2$H$_5$ | H | H |
| C$_3$H$_7$ | H | H |
| i-C$_3$H$_7$ | H | H |
| C$_4$H$_9$ | H | H |
| i-C$_4$H$_9$ | H | H |
| s-C$_4$H$_9$ | H | H |
| t-C$_4$H$_9$ | H | H |
| CH$_3$ | CH$_3$ | H |
| C$_2$H$_5$ | CH$_3$ | H |
| C$_3$H$_7$ | CH$_3$ | H |
| i-C$_3$H$_7$ | CH$_3$ | H |
| C$_4$H$_9$ | CH$_3$ | H |
| i-C$_4$H$_9$ | CH$_3$ | H |
| s-C$_4$H$_9$ | CH$_3$ | H |
| t-C$_4$H$_9$ | CH$_3$ | H |
| C$_2$H$_5$ | C$_2$H$_5$ | H |
| C$_3$H$_7$ | C$_3$H$_7$ | H |
| cyclopropyl | CH$_3$ | H |
| cyclopentyl | CH$_3$ | H |
| cyclohexyl | CH$_3$ | H |
| —(CH$_2$)$_2$— |  | H |
| —(CH$_2$)$_4$— |  | H |
| —(CH$_2$)$_5$— |  | H |
| —(CH$_2$)$_6$— |  | H |
| —(CH$_2$)$_7$— |  | H |
| —(CH$_2$)$_2$—O—(CH$_2$)$_2$— |  | H |
| —CH$_2$—O—(CH$_2$)$_3$— |  | H |
| —(CH$_2$)$_2$—S—(CH$_2$)$_2$— |  | H |
| —CH$_2$—CHCH$_3$—(CH$_2$)$_3$— |  | H |
| —(CH$_2$)$_2$—CHCH$_3$—(CH$_2$)$_2$— |  | H |
| —(CH$_2$)$_2$—CHC$_2$H$_5$—(CH$_2$)$_2$— |  | H |
| —(CH$_2$)$_2$—CHC$_3$H$_7$—(CH$_2$)$_2$— |  | H |
| —(CH$_2$)$_2$—CHi-C$_3$H$_7$—(CH$_2$)$_2$— |  | H |
| —(CH$_2$)$_2$—CHOCH$_3$—(CH$_2$)$_2$— |  | H |
| —(CH$_2$)$_2$—CHOC$_2$H$_5$—(CH$_2$)$_2$— |  | H |
| —(CH$_2$)$_2$—CHOC$_3$H$_7$—(CH$_2$)$_2$— |  | H |
| —(CH$_2$)$_2$—CHi-C$_3$H$_7$—(CH$_2$)$_2$— |  | H |

| A | D | B |
|---|---|---|
| —(CH$_2$)$_3$— |  | H |
| —(CH$_2$)$_4$— |  | H |
| —CH$_2$—CHCH$_3$—CH$_2$— |  | H |
| —CH$_2$—CH$_2$—CHCH$_3$— |  | H |
| —CH$_2$—CHCH$_3$—CHCH$_3$— |  | H |
| —CH$_2$—S—CH$_2$— |  | H |
| —CH$_2$—S—(CH$_2$)$_2$— |  | H |
| —(CH$_2$)$_2$—S—CH$_2$— |  | H |
| —CH$_2$—CH—CH—(CH$_2$)$_3$ (bridged) |  | H |
| H | CH$_3$ | H |
| H | C$_2$H$_5$ | H |
| H | C$_3$H$_7$ | H |
| H | i-C$_3$H$_7$ | H |
| H | cyclopropyl | H |
| H | cyclopentyl | H |
| H | cyclohexyl | H |
| CH$_3$ | CH$_3$ | H |
| CH$_3$ | C$_2$H$_5$ | H |
| CH$_3$ | C$_3$H$_7$ | H |
| CH$_3$ | i-C$_3$H$_7$ | H |
| CH$_3$ | cyclopropyl | H |
| CH$_3$ | cyclopentyl | H |
| CH$_3$ | cyclohexyl | H |
| C$_2$H$_5$ | CH$_3$ | H |
| C$_2$H$_5$ | C$_2$H$_5$ | H |

Table 2: A, B, D, L and M are as stated in Table 1 X=C$_2$H$_5$; W=CH$_3$; V$^1$=H; V$^2$=H.

Table 3: A, B, D, L and M are as stated in Table 1 X=C$_2$H$_5$; W=C$_2$H$_5$; V$^1$=H; V$^2$=H.

Table 4: A, B, D, L and M are as stated in Table 1 X=CH$_3$; W=CH$_3$; V$^1$=4-Cl; V$^2$=H.

Table 5: A, B, D, L and M are as stated in Table 1 X=C$_2$H$_5$; W=CH$_3$; V$^1$=4-Cl; V$^2$=H.

Table 6: A, B, D, L and M are as stated in Table 1 X=C$_2$H$_5$; W=C$_2$H$_5$; V$^1$=4-Cl; V$^2$=H.

Table 7: A, B, D, L and M are as stated in Table 1 X=CH$_3$; W=CH$_3$; V$^1$=3-Cl; V$^2$=H.

Table 8: A, B, D, L and M are as stated in Table 1 X=C$_2$H$_5$; W=CH$_3$; V$^1$=3-Cl; V$^2$=H.

Table 9: A, B, D, L and M are as stated in Table 1 X=C$_2$H$_5$; W=C$_2$H$_5$; V$^1$=3-Cl; V$^2$=H.

Table 10: A, B, D, L and M are as stated in Table 1 X=CH$_3$; W=CH$_3$; V$^1$=2-Cl; V$^2$=4-Cl.

Table 11: A, B, D, L and M are as stated in Table 1 X=C$_2$H$_5$; W=CH$_3$; V$^1$=2-Cl; V$^2$=4-Cl.

Table 12: A, B, D, L and M are as stated in Table 1 X=C$_2$H$_5$; W=C$_2$H$_5$; V$^1$=2-Cl; V$^2$=4-Cl.

Table 13: A, B, D, L and M are as stated in Table 1 X=CH$_3$; W=CH$_3$; V$^1$=4-CF$_3$; V$^2$=H.

Table 14: A, B, D, L and M are as stated in Table 1 X=C$_2$H$_5$; W=CH$_3$; V$^1$=4-CF$_3$; V$^2$=H.

Table 15: A, B, D, L and M are as stated in Table 1 X=C$_2$H$_5$; W=C$_2$H$_5$; V$^1$=4-CF$_3$; V$^2$=H.

Table 16: A, B, D, L and M are as stated in Table 1 X=CH$_3$; W=CH$_3$; V$^1$=4-CH$_3$; V$^2$=H.

Table 17: A, B, D, L and M are as stated in Table 1 X=C$_2$H$_5$; W=CH$_3$; V$^1$=4-CH$_3$; V$^2$=H.

Table 18: A, B, D, L and M are as stated in Table 1 X=C$_2$H$_5$, W=C$_2$H$_5$; V$^1$=4-CH$_3$; V$^2$=H.

Table 19: A, B, D, L and M are as stated in Table 1 X=CH$_3$; W=CH$_3$; V$^1$=4-OCH$_3$; V$^2$=H.

Table 20: A, B, D, L and M are as stated in Table 1 X=C$_2$H$_5$; W=CH$_3$; V$^1$=4-OCH$_3$; V$^2$=H.

Table 21: A, B, D, L and M are as stated in Table 1 X=$C_2H_5$; W=$C_2H_5$; $V^1$=4-$OCH_3$; $V^2$=H.

In addition to the compounds mentioned in the Preparation Examples, the following compounds of the formula (I-1) may be specifically mentioned:

TABLE 22

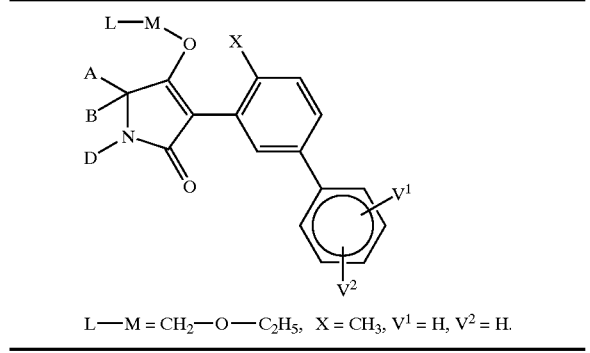

L—M = $CH_2$—O—$C_2H_5$, X = $CH_3$, $V^1$ = H, $V^2$ = H.

| A | B | D |
|---|---|---|
| $CH_3$ | H | H |
| $C_2H_5$ | H | H |
| $C_3H_7$ | H | H |
| i-$C_3H_7$ | H | H |
| $C_4H_9$ | H | H |
| i-$C_4H_9$ | H | H |
| s-$C_4H_9$ | H | H |
| t-$C_4H_9$ | H | H |
| $CH_3$ | $CH_3$ | H |
| $C_2H_5$ | $CH_3$ | H |
| $C_3H_7$ | $CH_3$ | H |
| i-$C_3H_7$ | $CH_3$ | H |
| $C_4H_9$ | $CH_3$ | H |
| i-$C_4H_9$ | $CH_3$ | H |
| s-$C_4H_9$ | $CH_3$ | H |
| t-$C_4H_9$ | $CH_3$ | H |
| $C_2H_5$ | $C_2H_5$ | H |
| $C_3H_7$ | $C_3H_7$ | H |
| cyclopropyl | $CH_3$ | H |
| cyclopentyl | $CH_3$ | H |
| cyclohexyl | $CH_3$ | H |
| —($CH_2$)$_2$— | | H |
| —($CH_2$)$_4$— | | H |
| —($CH_2$)$_5$— | | H |
| —($CH_2$)$_6$— | | H |
| —($CH_2$)$_7$— | | H |
| —($CH_2$)$_2$—O—($CH_2$)$_2$— | | H |
| —$CH_2$—O—($CH_2$)$_3$— | | H |
| —($CH_2$)$_2$—S—($CH_2$)$_2$— | | H |
| —$CH_2$—CH$CH_3$—($CH_2$)$_3$— | | H |
| —($CH_2$)$_2$—CH$CH_3$—($CH_2$)$_2$— | | H |
| —($CH_2$)$_2$—CH$C_2H_5$—($CH_2$)$_2$— | | H |
| —($CH_2$)$_2$—CH$C_3H_7$—($CH_2$)$_2$— | | H |
| —($CH_2$)$_2$—CHi-$C_3H_7$—($CH_2$)$_2$— | | H |
| —($CH_2$)$_2$—CH$OCH_3$—($CH_2$)$_2$— | | H |
| —($CH_2$)$_2$—CH$OC_2H_5$—($CH_2$)$_2$— | | H |
| —($CH_2$)$_2$—CH$OC_3H_7$—($CH_2$)$_2$— | | H |
| —($CH_2$)$_2$—CHi-$C_3H_7$—($CH_2$)$_2$— | | H |

| A | D | B |
|---|---|---|
| —($CH_2$)$_3$— | | H |
| —($CH_2$)$_4$— | | H |

TABLE 22-continued

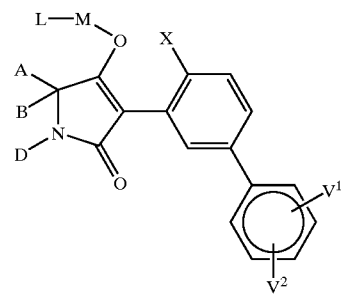

L—M = $CH_2$—O—$C_2H_5$, X = $CH_3$, $V^1$ = H, $V^2$ = H.

| A | B | D |
|---|---|---|
| —$CH_2$—CH$CH_3$—$CH_2$— | | H |
| —$CH_2$—$CH_2$—CH$CH_3$— | | H |
| —$CH_2$—CH$CH_3$—CH$CH_3$— | | H |
| —$CH_2$—S—$CH_2$— | | H |
| —$CH_2$—S—($CH_2$)$_2$— | | H |
| —($CH_2$)$_2$—S—$CH_2$— | | H |
| —$CH_2$—CH———CH—($CH_2$)$_3$— (bridged) | | H |
| H | $CH_3$ | H |
| H | $C_2H_5$ | H |
| H | $C_3H_7$ | H |
| H | i-$C_3H_7$ | H |
| H | cyclopropyl | H |
| H | cyclopentyl | H |
| H | cyclohexyl | H |
| $CH_3$ | $CH_3$ | H |
| $CH_3$ | $C_2H_5$ | H |
| $CH_3$ | $C_3H_7$ | H |
| $CH_3$ | i-$C_3H_7$ | H |
| $CH_3$ | cyclopropyl | H |
| $CH_3$ | cyclopentyl | H |
| $CH_3$ | cyclohexyl | H |
| $C_2H_5$ | $CH_3$ | H |
| $C_2H_5$ | $C_2H_5$ | H |

Table 23: A, B, D, L and M are as stated in Table 22 X=Cl; $V^1$=H; $V^2$=H.

Table 24: A, B, D, L and M are as stated in Table 22 X=$C_2H_5$; $V^1$=H; $V^2$=H.

Table 25: A, B, D, L and M are as stated in Table 22 X=$CH_3$; $V^1$=4-Cl; $V^2$=H.

Table 26: A, B, D, L and M are as stated in Table 22 X=$C_2H_5$; $V^1$=4-Cl; $V^2$=H.

Table 27: A, B, D, L and M are as stated in Table 22 X=Cl; $V^1$=4-Cl; $V^2$=H.

Table 28: A, B, D, L and M are as stated in Table 22 X=CH₃; V¹=3-Cl; V²=H.
Table 29: A, B, D, L and M are as stated in Table 22 X=C₂H₅; V¹=3-Cl; V²=H.
Table 30: A, B, D, L and M are as stated in Table 22 X=Cl; V¹=3-Cl; V²=H.
Table 31: A, B, D, L and M are as stated in Table 22 X=CH₃; V¹=2-Cl; V²=4-Cl.
Table 32: A, B, D, L and M are as stated in Table 22 X=C₂H₅; V¹=2-Cl; V²=4-Cl.
Table 33: A, B, D, L and M are as stated in Table 22 X=Cl; V¹=2-Cl; V²=4-Cl.
Table 34: A, B, D, L and M are as stated in Table 22 X=CH₃; V¹=4-CF₃; V²=H.
Table 35: A, B, D, L and M are as stated in Table 22 X=C₂H₅; V¹=4-CF₃; V²=H.
Table 36: A, B, D, L and M are as stated in Table 22 X=Cl; V¹=4CF₃; V²=H.
Table 37: A, B, D, L and M are as stated in Table 22 X=CH₃; V¹=4-CH₃; V²=H.
Table 38: A, B, D, L and M are as stated in Table 22 X=C₂H₅; V¹=4-CF₃; V²=H.
Table 39: A, B, D, L and M are as stated in Table 22 X=Cl; V¹=4-CH₃; V²=H.
Table 40: A, B, D, L and M are as stated in Table 22 X=CH₃; V¹=4-OCH₃; V²=H.
Table 41: A, B, D, L and M are as stated in Table 22 X=C₂H₅; V¹=4-OCH₃; V²=H.
Table 42: A, B, D, L and M are as stated in Table 22 X=Cl; V¹=4-OCH₃; V²=H.

In addition to the compounds mentioned in the Preparation Examples, the following compounds of the formula (I-1) may be specifically mentioned:

TABLE 43

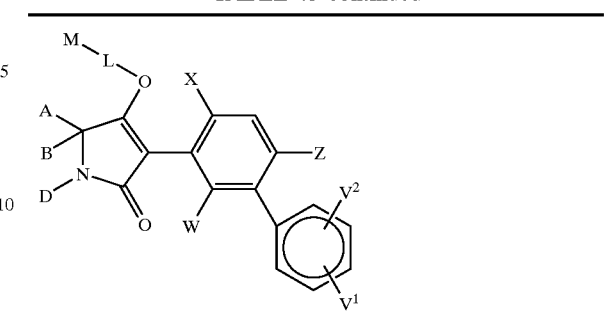

L—M = CH₂—O—C₂H₅, W = CH₃, X = CH₃, Z = H, V¹ = H, V² = H

| A | B | D |
|---|---|---|
| CH₃ | H | H |
| C₂H₅ | H | H |
| C₃H₇ | H | H |
| i-C₃H₇ | H | H |
| C₄H₉ | H | H |
| i-C₄H₉ | H | H |
| s-C₄H₉ | H | H |
| t-C₄H₉ | H | H |
| CH₃ | CH₃ | H |
| C₂H₅ | CH₃ | H |
| C₃H₇ | CH₃ | H |
| i-C₃H₇ | CH₃ | H |
| C₄H₉ | CH₃ | H |
| i-C₄H₉ | CH₃ | H |
| s-C₄H₉ | CH₃ | H |
| t-C₄H₉ | CH₃ | H |
| C₂H₅ | C₂H₅ | H |
| C₃H₇ | C₃H₇ | H |

TABLE 43-continued

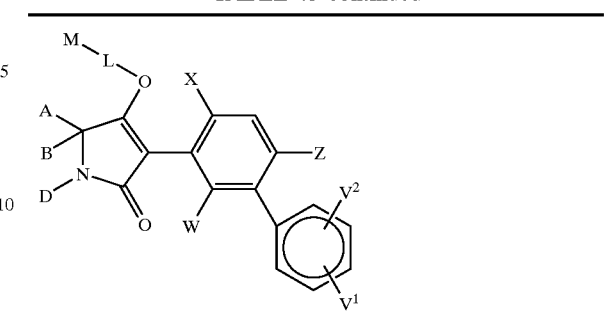

L—M = CH₂—O—C₂H₅, W = CH₃, X = CH₃, Z = H, V¹ = H, V² = H

| A | B | D |
|---|---|---|
| (cyclopropyl) | CH₃ | H |
| (cyclopentyl) | CH₃ | H |
| (cyclohexyl) | CH₃ | H |
| —(CH₂)₂— | | H |
| —(CH₂)₄— | | H |
| —(CH₂)₅— | | H |
| —(CH₂)₆— | | H |
| —(CH₂)₇— | | H |
| —(CH₂)₂—O—(CH₂)₂— | | H |
| —CH₂—O—(CH₂)₃— | | H |
| —(CH₂)₂—S—(CH₂)₂— | | H |
| —CH₂—CHCH₃—(CH₂)₃— | | H |
| —(CH₂)₂—CHCH₃—(CH₂)₂— | | H |
| —(CH₂)₂—CHC₂H₅—(CH₂)₂— | | H |
| —(CH₂)₂—CHC₃H₇—(CH₂)₂— | | H |
| —(CH₂)₂—CHi-C₃H₇—(CH₂)₂— | | H |
| —(CH₂)₂—CHOCH₃—(CH₂)₂— | | H |
| —(CH₂)₂—CHOC₂H₅—(CH₂)₂— | | H |
| —(CH₂)₂—CHOC₃H₇—(CH₂)₂— | | H |
| —(CH₂)₂—CHi-C₃H₇—(CH₂)₂— | | H |

| A | D | B |
|---|---|---|
| —(CH₂)₃— | | H |
| —(CH₂)₄— | | H |
| —CH₂—CHCH₃—CH₂— | | H |
| —CH₂—CH₂—CHCH₃— | | H |
| —CH₂—CHCH₃—CHCH₃— | | H |
| —CH₂—S—CH₂— | | H |
| —CH₂—S—(CH₂)₂— | | H |
| —(CH₂)₂—S—CH₂— | | H |
| —CH₂—CH————CH—— with —(CH₂)₃— bridge | | H |
| H | CH₃ | H |
| H | C₂H₅ | H |
| H | C₃H₇ | H |
| H | i-C₃H₇ | H |
| H | (cyclopropyl) | H |
| H | (cyclopentyl) | H |

TABLE 43-continued

[Structure: pyrrolidinone-biphenyl skeleton with substituents M-L-O, A, B, D-N, X, Z, W, V¹, V²]

L—M = $CH_2$—O—$C_2H_5$, W = $CH_3$, X = $CH_3$, Z = H, V¹ = H, V² = H

| A | B | | |
|---|---|---|---|
| H | cyclohexyl | H | |
| $CH_3$ | $CH_3$ | H | |
| $CH_3$ | $C_2H_5$ | H | |
| $CH_3$ | $C_3H_7$ | H | |
| $CH_3$ | i-$C_3H_7$ | H | |
| $CH_3$ | cyclopropyl | H | |
| $CH_3$ | cyclopentyl | H | |
| $CH_3$ | cyclopentyl | H | |
| $C_2H_5$ | $CH_3$ | H | |
| $C_2H_5$ | $C_2H_5$ | H | |

Table 44: A, B, D, L and M are as stated in Table 43 W=H; X=$CH_3$; Z=$CH_3$; V¹=H; V²=H.
Table 45: A, B, D, L and M are as stated in Table 43 W=$CH_3$, X=$CH_3$; Z=H; V¹=4-Cl; V²=H.
Table 46: A, B, D, L and M are as stated in Table 43 W=H; X=$CH_3$; Z=$CH_3$; V¹=4-C; V²=H.
Table 47: A, B, D, L and M are as stated in Table 43 W=$CH_3$; X=$CH_3$; Z=H; V¹=3-Cl; V²=H.
Table 48: A, B, D, L and M are as stated in Table 43 W=H; X=$CH_3$; Z=$CH_3$; V¹=3-Cl; V²=H.
Table 49: A, B, D, L and M are as stated in Table 43 W=$CH_3$; X=$CH_3$; Z=H; V¹=2-Cl; V²=4-Cl.
Table 50: A, B, D, L and M are as stated in Table 43 W=H; X=$CH_3$; Z=$CH_3$; V¹=2-Cl; V²=4-Cl.
Table 51: A, B, D, L and M are as stated in Table 43 W=$CH_3$; X=$CH_3$; Z=H; V¹=4-$CF_3$; V²=H.
Table 52: A, B, D, L and M are as stated in Table 43 W=H; X=$C_2H_5$; Z=$CH_3$; V¹=4-$CF_3$; V²=H.
Table 53: A, B, D, L and M are as stated in Table 43 W=$CH_3$; X=$CH_3$; Z=H; V¹=4-$CH_3$; V²=H.
Table 54: A, B, D, L and M are as stated in Table 43 W=H; X $C_2H_5$; Z=$CH_3$; V¹=4-$CH_3$; V²=H.
Table 55: A, B, D, L and M are as stated in Table 43 W=$CH_3$; X=$CH_3$; Z=H; V¹=4-$OCH_3$; V²=H.
Table 56: A, B, D, L and M are as stated in Table 43 W=H; X=$C_2H_5$; Z=$CH_3$; V¹=4-$OCH_3$; V²=H.

In addition to the compounds mentioned in the Preparation Examples, the following compounds of the formula (I-2) may be specifically mentioned:

TABLE 57

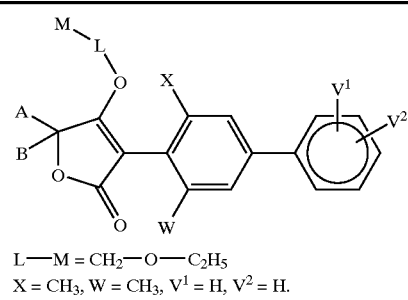

L—M = $CH_2$—O—$C_2H_5$
X = $CH_3$, W = $CH_3$, V¹ = H, V² = H.

| A | B |
|---|---|
| $CH_3$ | H |
| $C_2H_5$ | H |
| $C_3H_7$ | H |
| i-$C_3H_7$ | H |
| $C_4H_9$ | H |
| i-$C_4H_9$ | H |
| s-$C_4H_9$ | H |
| t-$C_4H_9$ | H |
| $CH_3$ | $CH_3$ |
| $C_2H_5$ | $CH_3$ |
| $C_3H_7$ | $CH_3$ |
| i-$C_3H_7$ | $CH_3$ |
| $C_4H_9$ | $CH_3$ |
| i-$C_4H_9$ | $CH_3$ |
| s-$C_4H_9$ | $CH_3$ |
| t-$C_4H_9$ | $CH_3$ |
| $C_2H_5$ | $C_2H_5$ |
| $C_3H_7$ | $C_3H_7$ |
| cyclopropyl | $CH_3$ |
| cyclopentyl | $CH_3$ |
| cyclohexyl | $CH_3$ |
| —$(CH_2)_2$— | |
| —$(CH_2)_4$— | |
| —$(CH_2)_5$— | |
| —$(CH_2)_6$— | |
| —$(CH_2)_7$— | |
| —$(CH_2)_2$—O—$(CH_2)_2$— | |
| —$CH_2$—O—$(CH_2)_3$— | |
| —$(CH_2)_2$—S—$(CH_2)_2$— | |
| —$CH_2$—$CHCH_3$—$(CH_2)_3$— | |
| —$(CH_2)_2$—$CHCH_3$—$(CH_2)_2$— | |
| —$(CH_2)_2$—$CHC_2H_5$—$(CH_2)_2$— | |
| —$(CH_2)_2$—$CHC_3H_7$—$(CH_2)_2$— | |
| —$(CH_2)_2$—$CHi$-$C_3H_7$—$(CH_2)_2$— | |
| —$(CH_2)_2$—$CHOCH_3$—$(CH_2)_2$— | |
| —$(CH_2)_2$—$CHOC_2H_5$—$(CH_2)_2$— | |
| —$(CH_2)_2$—$CHOC_3H_7$—$(CH_2)_2$— | |
| —$(CH_2)_2$—$CHi$-$C_3H_7$—$(CH_2)_2$— | |
| —$(CH_2)_2$—$C(CH_3)_2$—$(CH_2)_2$— | |
| —$CH_2$—$(CHCH_3)_2$—$(CH_2)_2$— | |
| —$CH_2$—CH—$(CH_2)_2$—CH— with —$CH_2$— bridge | |
| —$CH_2$—CH——CH—$CH_2$— with —$(CH_2)_4$— bridge | |

TABLE 57-continued

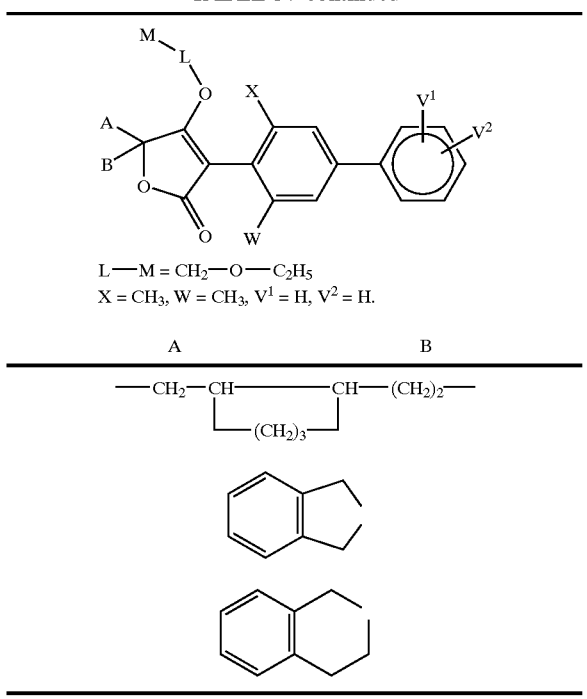

L—M = CH$_2$—O—C$_2$H$_5$
X = CH$_3$, W = CH$_3$, V$^1$ = H, V$^2$ = H.

| A | B |
|---|---|
| —CH$_2$—CH——————CH—(CH$_2$)$_2$— with —(CH$_2$)$_3$— bridge | |
| indane group | |
| tetrahydronaphthalene group | |

Table 58: A, B, L and M are as stated in Table 57 X=C$_2$H$_5$; W=CH$_3$; V$^1$=H; V$^2$=H.
Table 59: A, B, L and M are as stated in Table 57 X=C$_2$H$_5$; W=C$_2$H$_5$; V$^1$=H; V$^2$=H.
Table 60: A, B, L and M are as stated in Table 57 X=CH$_3$; W=CH$_3$; V$^1$=4-Cl; V$^2$=H.
Table 61: A, B, L and M are as stated in Table 57 X=C$_2$H$_5$; W=CH$_3$; V$^1$=4-Cl; V$^2$=H.
Table 62: A, B, L and M are as stated in Table 57 X=C$_2$H$_5$; W=C$_2$H$_5$; V$^1$=4-Cl; V$^2$=H.
Table 63: A, B, L and M are as stated in Table 57 X=CH$_3$; W=CH$_3$; V$^1$=3-C; V$^2$=H.
Table 64: A, B, L and M are as stated in Table 57 X=C$_2$H$_5$; W=CH$_3$; V$^1$=3-Cl; V$^2$=H.
Table 65: A, B, L and M are as stated in Table 57 X=C$_2$H$_5$; W=C$_2$H$_5$; V$^1$=3Cl; V$^2$=H.
Table 66: A, B, L and M are as stated in Table 57 X=CH$_3$; W=CH$_3$; V$^1$=4-CF$_3$; V$^2$=H.
Table 67: A, B, L and M are as stated in Table 57 X=C$_2$H$_5$; W=CH$_3$; V$^1$=4CF$_3$; V$^2$=H.
Table 68: A, B, L and M are as stated in Table 57 X=C$_2$H$_5$; W=C$_2$H$_5$; V%1=4-CF$_3$; V$^2$=H.
Table 69: A, B, L and M are as stated in Table 57 X=CH$_3$; W=CH$_3$; V$^1$=2-Cl; V$^2$=4-Cl.
Table 70: A, B, L and M are as stated in Table 57 X=C$_2$H$_5$; W=CH$_3$; V$^1$=2-Cl; V$^2$=4-Cl.
Table 71: A, B, L and M are as stated in Table 57 X=C$_2$H$_5$; W=C$_2$H$_5$; V$^1$=2-Cl; V$^2$=4-Cl.
Table 72: A, B, L and M are as stated in Table 57 X=CH$_3$; W=CH$_3$; V$^1$=4-CH$_3$; V$^2$=H.
Table 73: A, B, L and M are as stated in Table 57 X=C$_2$H$_5$; W=CH$_3$; V$^1$=4-CH$_3$; V$^2$=H.
Table 74: A, B, L and M are as stated in Table 57 X=C$_2$H$_5$; W=C$_2$H$_5$; V$^1$=4-CH$_3$; V$^2$=H.
Table 75: A, B, L and M are as stated in Table 57 X=CH$_3$; W=CH$_3$; V$^1$=4-OCH$_3$; V$^2$=H.
Table 76: A, B, L and M are as stated in Table 57 X=C$_2$H$_5$; W=CH$_3$; V$^1$=4-OCH$_3$; V$^2$=H.
Table 77: A, B, L and M are as stated in Table 57 X=C$_2$H$_5$; W=C$_2$H$_5$; V$^1$=4-OCH$_3$; V$^2$=H.

In addition to the compounds mentioned in the Preparation Examples, the following compounds of formula (I-2) may be specifically mentioned:

TABLE 78

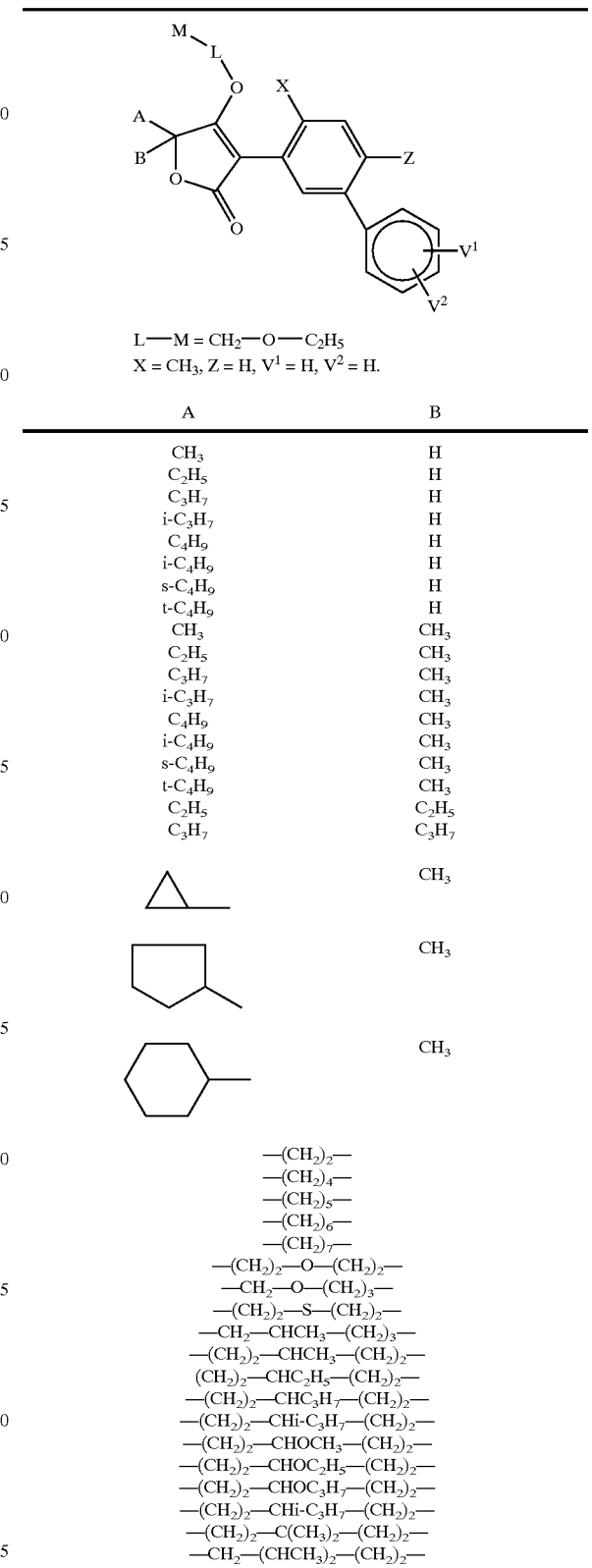

L—M = CH$_2$—O—C$_2$H$_5$
X = CH$_3$, Z = H, V$^1$ = H, V$^2$ = H.

| A | B |
|---|---|
| CH$_3$ | H |
| C$_2$H$_5$ | H |
| C$_3$H$_7$ | H |
| i-C$_3$H$_7$ | H |
| C$_4$H$_9$ | H |
| i-C$_4$H$_9$ | H |
| s-C$_4$H$_9$ | H |
| t-C$_4$H$_9$ | H |
| CH$_3$ | CH$_3$ |
| C$_2$H$_5$ | CH$_3$ |
| C$_3$H$_7$ | CH$_3$ |
| i-C$_3$H$_7$ | CH$_3$ |
| C$_4$H$_9$ | CH$_3$ |
| i-C$_4$H$_9$ | CH$_3$ |
| s-C$_4$H$_9$ | CH$_3$ |
| t-C$_4$H$_9$ | CH$_3$ |
| C$_2$H$_5$ | C$_2$H$_5$ |
| C$_3$H$_7$ | C$_3$H$_7$ |
| cyclopropyl | CH$_3$ |
| cyclopentyl | CH$_3$ |
| cyclohexyl | CH$_3$ |
| —(CH$_2$)$_2$— | |
| —(CH$_2$)$_4$— | |
| —(CH$_2$)$_5$— | |
| —(CH$_2$)$_6$— | |
| —(CH$_2$)$_7$— | |
| —(CH$_2$)$_2$—O—(CH$_2$)$_2$— | |
| —CH$_2$—O—(CH$_2$)$_3$— | |
| —(CH$_2$)$_2$—S—(CH$_2$)$_2$— | |
| —CH$_2$—CHCH$_3$—(CH$_2$)$_3$— | |
| —(CH$_2$)$_2$—CHCH$_3$—(CH$_2$)$_2$— | |
| (CH$_2$)$_2$—CHC$_2$H$_5$—(CH$_2$)$_2$— | |
| —(CH$_2$)$_2$—CHC$_3$H$_7$—(CH$_2$)$_2$— | |
| —(CH$_2$)$_2$—CHi-C$_3$H$_7$—(CH$_2$)$_2$— | |
| —(CH$_2$)$_2$—CHOCH$_3$—(CH$_2$)$_2$— | |
| —(CH$_2$)$_2$—CHOC$_2$H$_5$—(CH$_2$)$_2$— | |
| —(CH$_2$)$_2$—CHOC$_3$H$_7$—(CH$_2$)$_2$— | |
| —(CH$_2$)$_2$—CHi-C$_3$H$_7$—(CH$_2$)$_2$— | |
| —(CH$_2$)$_2$—C(CH$_3$)$_2$—(CH$_2$)$_2$— | |
| —CH$_2$—(CHCH$_3$)$_2$—(CH$_2$)$_2$— | |

TABLE 78-continued

*Structure: L—M—O—[ring A-B with O and C=O]—phenyl(X,Z)—phenyl(V¹,V²)*

L—M = CH$_2$—O—C$_2$H$_5$
X = CH$_3$, Z = H, V$^1$ = H, V$^2$ = H.

| A | B |
|---|---|
| —CH$_2$—CH—(CH$_2$)$_2$—CH— with —CH$_2$— bridge | |
| —CH$_2$—CH——CH—CH$_2$— with —(CH$_2$)$_4$— bridge | |
| —CH$_2$—CH——CH—(CH$_2$)$_2$— with —(CH$_2$)$_3$— bridge | |
| indane ring | |
| tetralin ring | |

Table 79: A, B, L and M are as stated in Table 78 X=Cl; Z=H; V$^1$=H; V$^2$=H.
Table 80: A, B, L and M are as stated in Table 78 X=CH$_3$; Z=CH$_3$; V$^1$=H; V$^2$=H.
Table 81: A, B, L and M are as stated in Table 78 X=CH$_3$; Z=H; V$^1$=4-Cl; V$^2$=H.
Table 82: A, B, L and M are as stated in Table 78 X=Cl; Z=H; V$^1$=4-Cl; V$^2$=H.
Table 83: A, B, L and M are as stated in Table 78 X=CH$_3$; Z=CH$_3$; V$^1$=4-Cl; V$^2$=H.
Table 84: A, B, L and M are as stated in Table 78 X=CH$_3$; Z=H; V$^1$=3-Cl; V$^2$=H.
Table 85: A, B, L and M are as stated in Table 78 X=Cl; Z=H; V$^1$=3-Cl; V$^2$=H.
Table 86: A, B, L and M are as stated in Table 78 X=CH$_3$; Z=CH$_3$; V$^1$=3Cl; V$^2$=H.
Table 87: A, B, L and M are as stated in Table 78 X=CH$_3$; Z=H; V$^1$=4-CF$_3$; V$^2$=H.
Table 88: A, B, L and M are as stated in Table 78 X=Cl; Z=H; V$^1$=4-CF$_3$; V$^2$=H.
Table 89: A, B, L and M are as stated in Table 78 X=CH$_3$; Z=CH$_3$; V$^1$=4CF$_3$; V$^2$=H.
Table 90: A, B, L and M are as stated in Table 78 X=CH$_3$; Z=H; V$^1$=2-Cl; V$^2$=4-Cl.
Table 91: A, B, L and M are as stated in Table 78 X=Cl; Z=H; V$^1$=2-Cl; V$^2$=4-Cl.
Table 92: A, B, L and M are as stated in Table 78 X=CH$_3$; Z=CH$_3$; V$^1$=2-Cl; V$^2$=4-Cl.
Table 93: A, B, L and M are as stated in Table 78 X=CH$_3$; Z=H; V$^1$=4-CH$_3$; V$^2$=H.
Table 94: A, B, L and M are as stated in Table 78 X=Cl; Z=H; V$^1$=4-CH$_3$; V$^2$=H.
Table 95: A, B, L and M are as stated in Table 78 X=CH$_3$; Z=CH$_3$; V$^1$=4-CH$_3$; V$^2$=H.
Table 96: A, B, L and M are as stated in Table 78 X=CH$_3$; Z=H; V$^1$=4-OCH$_3$; V$^2$=H.
Table 97: A, B, L and M are as stated in Table 78 X=Cl; Z=H; V$^1$=4-OCH$_3$; V$^2$=H.
Table 98: A, B, L and M are as stated in Table 78 X=CH$_3$; Z=CH$_3$; V$^1$=4-OCH$_3$; V$^2$=H.

In addition to the compounds mentioned in the Preparation Examples, the following compounds of the formula (I-7) may be specifically mentioned:

TABLE 99

*Structure: L—M—O—[ring A-B with cyclopentanone]—phenyl(X,W)—phenyl(V¹,V²)*

L—M = CH$_2$—O—C$_2$H$_5$
X = CH$_3$, W = CH$_3$, V$^1$ = H, V$^2$ = H.

| A | B |
|---|---|
| CH$_3$ | H |
| C$_2$H$_5$ | H |
| C$_3$H$_7$ | H |
| i-C$_3$H$_7$ | H |
| CH$_3$ | CH$_3$ |
| C$_2$H$_5$ | CH$_3$ |
| C$_3$H$_7$ | CH$_3$ |
| i-C$_3$H$_7$ | CH$_3$ |
| —(CH$_2$)$_4$— | |
| —(CH$_2$)$_5$— | |
| —(CH$_2$)$_2$—O—(CH$_2$)$_2$— | |
| —CH$_2$—O—(CH$_2$)$_3$— | |
| —(CH$_2$)$_2$—CHCH$_3$—(CH$_2$)$_2$— | |
| —(CH$_2$)$_2$—CHOCH$_3$—(CH$_2$)$_2$— | |
| —(CH$_2$)$_2$—CHOC$_2$H$_5$—(CH$_2$)$_2$— | |
| —(CH$_2$)$_2$—CHOC$_3$H$_7$—(CH$_2$)$_2$— | |

Table 100: A, B, L and M are as stated in Table 99 X=C$_2$H$_5$; W=CH$_3$, V$^1$=H; V$^2$=H.
Table 101: A, B, L and M are as stated in Table 99 X=C$_2$H$_5$; W=C$_2$H$_5$; V$^1$=H; V$^2$=H.
Table 102: A, B, L and M are as stated in Table 99 X=CH$_3$; W=CH$_3$; V$^1$=4-Cl; V$^2$=H.
Table 103: A, B, L and M are as stated in Table 99 X=C$_2$H$_5$; W=CH$_3$; V$^1$=4-Cl; V$^2$=H.
Table 104: A, B, L and M are as stated in Table 99 X=C$_2$H$_5$; W=C$_2$H$_5$; V$^1$=4-Cl; V$^2$=H.
Table 105: A, B, L and M are as stated in Table 99 X=CH$_3$; W=CH$_3$; V$^1$=3-Cl; V$^2$=H.
Table 106: A, B, L and M are as stated in Table 99 X=C$_2$H$_5$; W=CH$_3$; V$^1$=3-Cl; V$^2$=H.
Table 107: A, B, L and M are as stated in Table 99 X=C$_2$H$_5$; W=C$_2$H$_5$; V$^1$=3-Cl; V$^2$=H.
Table 108: A, B, L and M are as stated in Table 99 X=CH$_3$; W=CH$_3$; V$^1$=4-CF$_3$; V$^2$=H.
Table 109: A, B, L and M are as stated in Table 99 X=C$_2$H$_5$; W=CH$_3$; V$^1$=4-CF$_3$; V$^2$=H.
Table 110: A, B, L and M are as stated in Table 99 X=C$_2$H$_5$; W=C$_2$H$_5$; V$^1$=4-CF$_3$; V$^2$=H.
Table 111: A, B, L and M are as stated in Table 99 X=CH$_3$; W=CH$_3$; V$^1$=2-Cl; V$^2$=4-Cl.

Table 112: A, B, L and M are as stated in Table 99 X=$C_2H_5$; W=$CH_3$; $V^1$=2-Cl; $V^2$=4-Cl.
Table 113: A, B, L and M are as stated in Table 99 X=$C_2H_5$; W=$C_2H_5$; $V^1$=2-Cl; $V^2$=4-Cl.
Table 114: A, B, L and M are as stated in Table 99 X=$CH_3$; W=$CH_3$; $V^1$=4-$CH_3$; $V^2$=H.
Table 115: A, B, L and M are as stated in Table 99 X=$C_2H_5$; W=$CH_3$; $V^1$=4-$CH_3$; $V^2$=H.
Table 116: A, B, L and M are as stated in Table 99 X=$C_2H_5$; W=$C_2H_5$; $V^1$=4-$CH_3$; $V^2$=H.
Table 117: A, B, L and M are as stated in Table 99 X=$CH_3$; W $CH_3$; $V^1$=4-$OCH_3$; $V^2$=H.
Table 118: A, B, L and M are as stated in Table 99 X=$C_2H_5$; W=$CH_3$; $V^1$=4-$OCH_3$; $V^2$=H.
Table 119: A, B, L and M are as stated in Table 99 X=$C_2H_5$; W=$C_2H_5$; $V^1$=4-$OCH_3$; $V^2$=H.

In addition to the compounds mentioned in the Preparation Examples, the following compounds of the formula (I-7) may be specifically mentioned:

TABLE 120

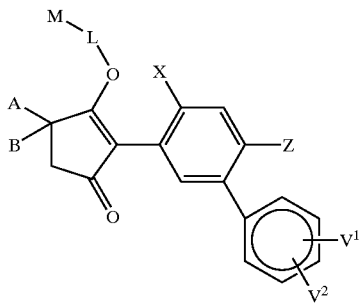

L—M = $CH_2$—O—$C_2H_5$
X = $CH_3$, Z = H, $V^1$ = H, $V^2$ = H.

| A | B |
|---|---|
| $CH_3$ | H |
| $C_2H_5$ | H |
| $C_3H_7$ | H |
| i-$C_3H_7$ | H |
| $CH_3$ | $CH_3$ |
| $C_2H_5$ | $CH_3$ |
| $C_3H_7$ | $CH_3$ |
| i-$C_3H_7$ | $CH_3$ |
| —$(CH_2)_4$— | |
| —$(CH_2)_5$— | |
| —$(CH_2)_2$—O—$(CH_2)_2$— | |
| —$CH_2$—O—$(CH_2)_3$— | |
| —$(CH_2)_2$—$CHCH_3$—$(CH_2)_2$— | |
| —$(CH_2)_2$—$CHC_2H_5$—$(CH_2)_2$— | |
| —$(CH_2)_2$—$CHOCH_3$—$(CH_2)_2$— | |
| —$(CH_2)_2$—$CHOC_2H_5$—$(CH_2)_2$— | |
| —$(CH_2)_2$—$CHOC_3H_7$—$(CH_2)_2$— | |

Table 121: A, B, L and M are as stated in Table 120 X=Cl; Z=H; $V^1$=H; $V^2$=H.
Table 122: A, B, L and M are as stated in Table 120 X=$CH_3$; Z=$CH_3$; $V^1$=H; $V^2$=H.
Table 123: A, B, L and M are as stated in Table 120 X=$CH_3$; Z=H; $V^1$=4-Cl; $V^2$=H.
Table 124: A, B, L and M are as stated in Table 120 X=Cl; Z=H; $V^1$=4-Cl; $V^2$=H.
Table 125: A, B, L and M are as stated in Table 120 X=$CH_3$; Z=$CH_3$; $V^1$=4-Cl; $V^2$=H.
Table 126: A, B, L and M are as stated in Table 120 X=$CH_3$; Z=H; $V^1$=3-Cl; $V^2$=H.
Table 127: A, B, L and M are as stated in Table 120 X=Cl; Z=H; $V^1$=3-Cl; $V^2$=H.
Table 128: A, B, L and M are as stated in Table 120 X=$CH_3$; Z=$CH_3$; $V^1$=4-Cl; $V^2$=H.
Table 129: A, B, L and M are as stated in Table 120 X=$CH_3$; Z=H; $V^1$=2-Cl; $V^2$=4-Cl.
Table 130: A, B, L and M are as stated in Table 120 X=Cl; Z=H; $V^1$=2-Cl; $V^2$=4-Cl.
Table 131: A, B, L and M are as stated in Table 120 X=$CH_3$; Z=$CH_3$; $V^1$=2-Cl; $V^2$=4-Cl.
Table 132: A, B, L and M are as stated in Table 120 X=$CH_3$; Z=H; $V^1$=4-$CF_3$; $V^2$=H.
Table 133: A, B, L and M are as stated in Table 120 X=Cl; Z=H; $V^1$=4-$CF_3$; $V^2$=H.
Table 134: A, B, L and M are as stated in Table 120 X=$CH_3$; Z=$CH_3$; $V^1$=4-$CF_3$; $V^2$=H.
Table 135: A, B, L and M are as stated in Table 120 X=$CH_3$; Z=H; $V^1$=4-$CH_3$; $V^2$=H.
Table 136: A, B, L and M are as stated in Table 120 X=Cl; Z=H; $V^1$=4-$CH_3$; $V^2$=H.
Table 137: A, B, L and M are as stated in Table 120 X=$CH_3$; Z=$CH_3$; $V^1$=4-CH ; $V^2$=H.
Table 138: A, B, L and M are as stated in Table 120 X=$CH_3$; Z=H; $V^1$=4-$OCH_3$; $V^2$=H.
Table 139: A, B, L and M are as stated in Table 120 X=Cl; Z=H; $V^1$=4-$OCH_3$; $V^2$=H.
Table 140: A, B, L and M are as stated in Table 120 X=$CH_3$; Z=$CH_3$; $V^1$=4-$OCH_3$; $V^2$=H.

In addition to the compounds mentioned in the Preparation Examples, the following compounds of the formula (I-8) may be specifically mentioned:

TABLE 141

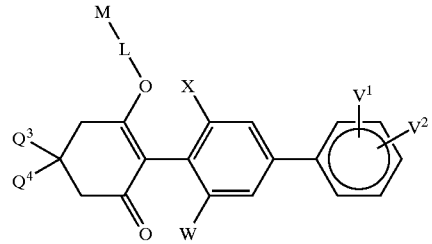

L—M = $CH_2$—O—$C_2H_5$
X = $CH_3$, W = $CH_3$, $V^1$ = H, $V^2$ = H.

| $Q^3$ | $Q^4$ |
|---|---|
| H | H |
| $CH_3$ | H |
| $C_2H_5$ | H |
| $C_3H_7$ | H |
| i-$C_3H_7$ | H |
| $CH_3$ | $CH_3$ |
| $C_2H_5$ | $CH_3$ |
| $C_3H_7$ | $CH_3$ |
| i-$C_3H_7$ | $CH_3$ |
| —$(CH_2)_4$— | |
| —$(CH_2)_5$— | |
| —$(CH_2)_2$—O—$(CH_2)_2$— | |
| —$CH_2$—O—$(CH_2)_3$— | |
| —$(CH_2)_2$—$CHCH_3$—$(CH_2)_2$— | |
| $(CH_2)_2$—$CHC_2H_5$—$(CH_2)_2$— | |
| —$(CH_2)_2$—$CHOCH_3$—$(CH_2)_2$— | |
| —$(CH_2)_2$—$CHOC_2H_5$—$(CH_2)_2$— | |
| —$(CH_2)_2$—$CHOC_3H_7$—$(CH_2)_2$— | |

Table 142: $Q^3$, $Q^4$, L and M are as stated in Table 141 X=$C_2H_5$; W=$CH_3$; $V^1$=H; $V^2$=H.
Table 143: $Q^3$, $Q^4$, L and M are as stated in Table 141 X=$C_2H_5$; W=$C_2H_5$; $V^1$=H; $V^2$=H.
Table 144: $Q^3$, $Q^4$, L and M are as stated in Table 141 X=$CH_3$; W=$CH_3$; $V^1$=4-Cl; $V^2$=H.

Table 145: $Q^3$, $Q^4$, L and M are as stated in Table 141 X=$C_2H_5$; W=$CH_3$; $V^1$=4-Cl; $V^2$=H.
Table 146: $Q^3$, $Q^4$, L and M are as stated in Table 141 X=$C_2H_5$; W=$C_2H_5$; $V^1$=4-Cl; $V^2$=H.
Table 147: $Q^3$, $Q^4$, L and M are as stated in Table 141 X=$CH_3$; W=$CH_3$; $V^1$=3-Cl; $V^2$=H.
Table 148: $Q^3$, $Q^4$, L and M are as stated in Table 141 X=$C_2H_5$; W=$CH_3$; $V^1$=3Cl; $V^2$=H.
Table 149: $Q^3$, $Q^4$, L and M are as stated in Table 141 X=$C_2H_5$; W=$C_2H_5$; $V^1$=3-Cl; $V^2$=H.
Table 150: $Q^3$, $Q^4$, L and M are as stated in Table 141 X=$CH_3$; W=$CH_3$; $V^1$=4-$CF_3$; $V^2$=H.
Table 151: $Q^3$, $Q^4$, L and M are as stated in Table 141 X=$C_2H_5$; W=$CH_3$; $V^1$=4-$CF_3$; $V^2$=H.
Table 152: $Q^3$, $Q^4$, L and M are as stated in Table 141 X=$C_2H_5$; W=$C_2H_5$; $V^1$=4-$CF_3$; $V^2$=H.
Table 153: $Q^3$, $Q^4$, L and M are as stated in Table 141 X=$CH_3$; W=$CH_3$; $V^1$=2-Cl; $V^2$=4-Cl.
Table 154: $Q^3$, $Q^4$, L and M are as stated in Table 141 X=$C_2H_5$; W=$CH_3$; $V^1$=2-Cl; $V^2$=4-Cl.
Table 155: $Q^3$, $Q^4$, L and M are as stated in Table 141 X=$C_2H_5$; W=$C_2H_5$; $V^1$=2-Cl; $V^2$=4-Cl.
Table 156: $Q^3$, $Q^4$, L and M are as stated in Table 141 X=$CH_3$; W=$CH_3$; $V^1$=4-$CH_3$; $V^2$=H.
Table 157: $Q^3$, $Q^4$, L and M are as stated in Table 141 X=$C_2H_5$; W=$CH_3$; $V^1$=4-$CH_3$; $V^2$=H.
Table 158: $Q^3$, $Q^4$, and M are as stated in Table 141 X=$C_2H_5$; W=$C_2H_5$; $V^1$=4-$CH_3$; $V^2$=H.
Table 159: $Q^3$, $Q^4$, L and M are as stated in Table 141 X=$CH_3$; W=$CH_3$; $V^1$=4-$OCH_3$; $V^2$=H.
Table 160: $Q^3$, $Q^4$, L and M are as stated in Table 141 X=$C_2H_5$; W=$CH_3$; $V^1$=4-$OCH_3$; $V^2$=H.
Table 161: $Q^3$, $Q^4$, L and M are as stated in Table 141 X=$C_2H_5$; W=$C_2H_5$; $V^1$=4-$OCH_3$; $V^2$=H.

In addition to the compounds mentioned in the Preparation Examples, the following compounds of the formula (I-8) may be specifically mentioned:

TABLE 162

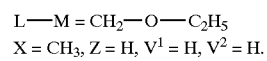

L—M = $CH_2$—O—$C_2H_5$
X = $CH_3$, Z = H, $V^1$ = H, $V^2$ = H.

| $Q^3$ | $Q^4$ |
|---|---|
| H | H |
| $CH_3$ | H |
| $C_2H_5$ | H |
| $C_3H_7$ | H |
| i-$C_3H_7$ | H |
| $CH_3$ | $CH_3$ |
| $C_2H_5$ | $CH_3$ |
| $C_3H_7$ | $CH_3$ |
| i-$C_3H_7$ | $CH_3$ |
| —$(CH_2)_4$— | |
| —$(CH_2)_5$— | |

TABLE 162-continued

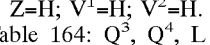

L—M = $CH_2$—O—$C_2H_5$
X = $CH_3$, Z = H, $V^1$ = H, $V^2$ = H.

| $Q^3$ | $Q^4$ |
|---|---|
| —$(CH_2)_2$—O—$(CH_2)_2$— | |
| —$CH_2$—O—$(CH_2)_3$— | |
| —$(CH_2)_2$—$CHCH_3$—$(CH_2)_2$— | |
| —$(CH_2)_2$—$CHC_2H_5$—$(CH_2)_2$— | |
| —$(CH_2)_2$—$CHOCH_3$—$(CH_2)_2$— | |
| —$(CH_2)_2$—$CHOC_2H_5$—$(CH_2)_2$— | |
| —$(CH_2)_2$—$CHOC_3H_7$—$(CH_2)_2$— | |

Table 163: $Q^3$, $Q^4$, L and M are as stated in Table 162 X=Cl; Z=H; $V^1$=H; $V^2$=H.
Table 164: $Q^3$, $Q^4$, L and M are as stated in Table 162 X=$CH_3$; Z=$CH_3$; $V^1$=H; $V^2$=H.
Table 165: $Q^3$, $Q^4$, L and M are as stated in Table 162 X=$CH_3$; Z=H; $V^1$=4-Cl; $V^2$=H.
Table 166: $Q^3$, $Q^4$, L and M are as stated in Table 162 X=Cl; Z=H; $V^1$=4-Cl; $V^2$=H.
Table 167: $Q^3$, $Q^4$, L and M are as stated in Table 162 X=$CH_3$; Z=$CH_3$; $V^1$=4-Cl; $V^2$=H.
Table 168: $Q^3$, $Q^4$, L and M are as stated in Table 162 X=$CH_3$; Z=H; $V^1$=3-Cl; $V^2$=H.
Table 169: $Q^3$, $Q^4$, L and M are as stated in Table 162 X=Cl; Z=H; $V^1$=3-Cl; $V^2$=H.
Table 170: $Q^3$, $Q^4$, L and M are as stated in Table 162 X=$CH_3$; Z=$CH_3$; $V^1$=3-Cl; $V^2$=H.
Table 171: $Q^3$, $Q^4$, L and M are as stated in Table 162 X=$CH_3$; Z=H; $V^1$=4-$CF_3$; $V^2$=H.
Table 172: $Q^3$, $Q^4$, L and M are as stated in Table 162 X=Cl; Z=H; $V^1$=4-$CF_3$; $V^2$=H.
Table 173: $Q^3$, $Q^4$, L and M are as stated in Table 162 X=$CH_3$; Z=$CH_3$; $V^1$=4-$CF_3$; $V^2$=H.
Table 174: $Q^3$, $Q^4$, L and M are as stated in Table 162 X=$CH_3$; Z=H; $V^1$=2-Cl; $V^2$=4-Cl.
Table 175: $Q^3$, $Q^4$, L and M are as stated in Table 162 X=Cl; Z=H; $V^1$=2-Cl; $V^2$=4-Cl.
Table 176: $Q^3$, $Q^4$, L and M are as stated in Table 162 X=$CH_3$; Z=$CH_3$; $V^1$=2-Cl; $V^2$=4-Cl.
Table 177: $Q^3$, $Q^4$, L and M are as stated in Table 162 X=$CH_3$; Z=H; $V^1$=4$CH_3$; $V^2$=H.
Table 178: $Q^3$, $Q^4$, L and M are as stated in Table 162 X=Cl; Z=H; $V^1$=4-$CH_3$; $V^2$=H.
Table 179: $Q^3$, $Q^4$, L and M are as stated in Table 162 X=$CH_3$; Z=$CH_3$; $V^1$=4-$CH_3$; $V^2$=H.
Table 180: $Q^3$, $Q^4$, L and M are as stated in Table 162 X=$CH_3$; Z=H; $V^1$=4-$OCH_3$; $V^2$=H.
Table 181: $Q^3$, $Q^4$, L and M are as stated in Table 162 X=Cl; Z=H; $V^1$=4-$OCH_3$; $V^2$=H.
Table 182: $Q^3$, $Q^4$, L and M are as stated in Table 162 X=$CH_3$; Z=$CH_3$; $V^1$=4-$OCH_3$; $V^2$=H.

Using, according to process (A), 3-[4-(4-chlorophenyl)-2,6-dimethyl-phenyl]-4-hydroxy-1-isopropyl-$\Delta^3$-pyrrolin- 2-one and ethyl N-chloromethyl-N-methyl-carbamate, the course of the process according to the invention can be represented by the reaction scheme below:

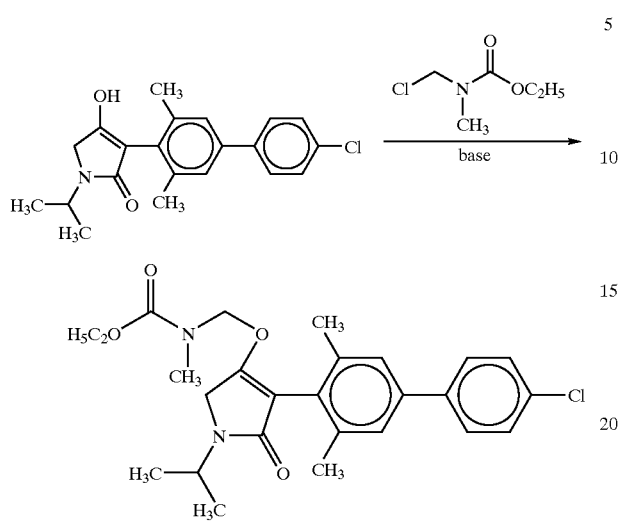

The compounds of the formulae (II-1) to (II-8)

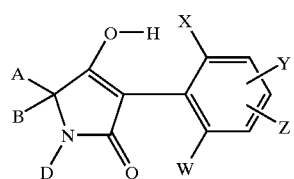
(II-1)

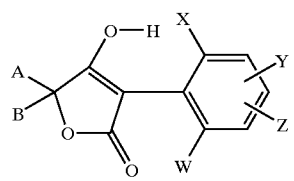
(II-2)

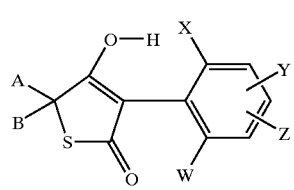
(II-3)

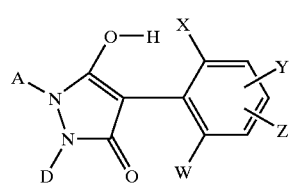
(II-4)

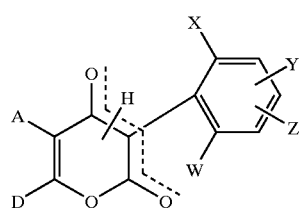
(II-5)

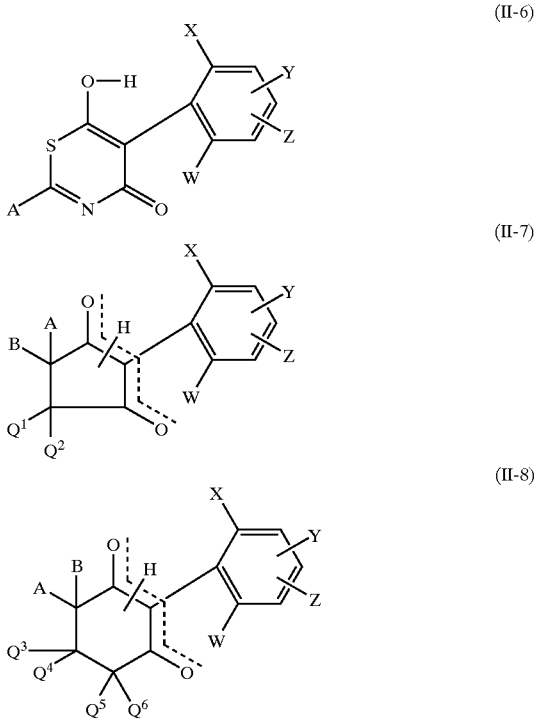

in which
A, B, D, L, M, $Q^1$, $Q^2$, $Q^3$, $Q^4$, $Q^5$, $Q^6$, W, X, Y and Z are as defined above,
which are required as starting materials in process (A) are known from not yet laid-open applications of the applicant (DE 19 808 261.4, DE 19813354.5 and DE 19818732.7)

The compounds of the formula (III) furthermore required for carrying out the process (A) according to the invention are generally known compounds of organic chemistry.

Suitable diluents for carrying out the process (A) according to the invention are all solvents which are inert to these compounds. Preference is given to using hydrocarbons, such as benzine, benzene, toluene, xylene and tetraline; furthermore halogenated hydrocarbons, such as methylene chloride, chloroform, carbon tetrachloride, chlorobenzene and o-dichlorobenzene; ethers, such as diethyl ether, tetrahydrofuran and dioxane; nitrites, such as acetonitrile or propionitrile; furthermore polar solvents which are inert to the compounds of the formula (III), such as dimethyl sulphoxide, dimethylformamide, sulpholane or N-methylpyrrolidone but also esters, such as ethyl acetate.

Suitable bases for carrying out the process (A) according to the invention are all customary acid acceptors. Preference is given to using alkali metal and alkaline earth metal oxides, hydroxides and carbonates, such as sodium hydroxide, potassium hydroxide, magnesium hydroxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464*) or TDA 1***) It is furthermore possible to use alkali metal and alkaline earth metal hydrides, such as sodium hydride and calcium hydride, and additionally also alkali metal alkoxides, such as sodium methoxide, sodium ethoxide and potassium tert-butoxide. Furthermore, it is possible to use tertiary amines, such as triethylamine, pyridine, DABCO, DBU, DBA, Hünig base and N,N-dimethylaniline.

*) Adogen 464=Methyltrialkyl($C_8$–$C_{10}$)ammonium chloride
***) TDA 1=Tris-(methoxyethoxyethyl)-amine When carrying out the process (A) according to the invention, the reaction temperatures can be varied within a relatively wide range. In general, the process is carried out at temperatures between −20° C. and 180° C. preferably between 0° C. and 130° C.

When carrying out the process (A) according to the invention, the reaction components (II-1) to (II-8) and (III) and the base are generally employed in approximately equimolar amounts. However, it is also possible to use a relatively large excess (up to 3 mol) of one component or the other.

The process (A) according to the invention is generally carried out under atmospheric pressure. Work-up is carried out by customary methods.

The active compounds are suitable for controlling animal pests, in particular insects, arachnids and nematodes, which are encountered in agriculture, in forestry, in the protection of stored products and of materials, and in the hygiene sector, and have good plant tolerance and favourable toxicity to warm-blooded animals. They may be preferably employed as plant protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spp.

From the order of the Symphyla, for example, *Scutigerella immaculate.*

From the order of the Thysanura, for example, *Lepisma saccharina.*

From the order of the Collembola, for example, *Onychiurus armatus.*

From the order of the Orthoptera, for example, *Acheta domesticus*, Gryllotalpa spp., *Locusta migratoria migratorioides*, Melanoplus spp. and *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, Reticulitermes spp.

From the order of the Phthiraptera, for example, *Pediculus humanus corporis*, Haematopinus spp., Linognathus spp., Trichodectes spp. and Damalinia spp.

From the order of the Thysanoptera, for example, *Hercinothrips femoralis, Thrips tabaci, Thrips palmi* and *Franklinielia occidentalis.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix*, Pemphigus spp., *Macrosiphum avenae*, Myzus spp., *Phorodon humuli, Rhopalosiphum padi*, Empoasca spp., *Euscelis bilobatus, Nephotettix cincticeps, Lecanium comi, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Mamestra brassicae, Panolis flammea*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana*, Cnaphalocerus spp., *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon soistitialis, Costelytra zealandica* and *Lissorhoptrus oryzophilus.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae, Tipula paludosa*, Hylemyia spp. and Liriomyza spp.

From the order of the Siphonaptera, for example, *Xenopsylla cheopis* and Ceratophyllus spp.

From the class of the Arachnida, for example, *Scorpio maurus, Latrodectus mactans, Acarus siro*, Argas spp., Omithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp., Hemitarsonemus spp., Brevipalpus spp.

The phytoparasitic nematodes include, for example, Pratylenchus spp., *Radopholus similis, Ditylenchus dipsaci, Tylenchulus semipenetrans*, Heterodera spp., Globodera spp., Meloidogyne spp., Aphelenchoides spp., Longidorus spp., Xiphinema spp., Trichodorus spp., Bursaphelenchus spp.

If appropriate, the compounds according to the invention can, at certain concentrations or application rates, also be used as herbicides or microbicides, for example as fungicides, antimycotics and bactericides. If appropriate, they can also be employed as intermediates or precursors for the synthesis of other active compounds.

The active compounds can be converted to the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the active compounds with extenders, that is, liquid solvents, and/or solid carriers, optionally with the use of surfactants, that is to say emulsifiers and/or dispersants, and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

Suitable solid carriers are:

for example ammonium salts and ground natural minerals such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; as emulsifiers and/or foam-formers there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; as dispersants there are suitable: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formnulations. Other possible additives are mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphoric acid esters, carbamates, carboxylates, chlorinated hydrocarbons, phenylureas and substances produced by microorganisms, inter alia.

Particularly favourable examples of co-components in mixtures are the following compounds:

Fungicides:

aldimorph, ampropylfos, ampropylfos-potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuiram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, fuirmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluamid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G, OK-8705,
OK-8801,
α-(1,1-dimethylethyl)-β-(2-phenoxyethyl)-1H-1,2,4-triazole-1-ethanol,
α-(2,4-dichlorophenyl)-β-fluoro-β-propyl-1H-1,2,4-triazole-1-ethanol,
α-(2,4-dichlorophenyl)-β-methoxy-α-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-α-(methoxyimino)-N-methyl-2-phenoxy-phenylacetamide,
1-isopropyl {2-methyl-1-[[[1-(4-methylphenyl)-ethyl]-amino]-carbonyl]-propyl}-carbamate,
1-(2,4-dichlorophenyl)-2-(1H-1,2,4-triazol-1-yl)-ethanone-O-(phenylmethyl)-oxime,
1-(2-methyl-1-naphthalenyl)-1H-pyrrol-2,5-dione,
1-(3,5-dichlorophenyl)-3-(2-propenyl)-2,5-pyrrolidindione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinole,
2',6'-dibromo-2-methyl-4'-trifluoromethoxy-4'-trifluoromethyl-1,3-thiazole-5-carboxanilide,
2,2-dichloro-N-[1-(4-chlorophenyl)-ethyl]-1-ethyl-3-methyl-cyclopropanecarboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrol-2,5-dione,
3,5-dichloro-N-[cyano[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy-]2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine hydrochloride,
ethyl [(4-chlorophenyl)-azo]-cyanoacetate,
potassium bicarbonate,
methanetetrathiol-sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro4-hydroxyphenyl)-1-methyl-cyclohexanecarboxamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one,
Bactericides:
  bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.
Insecticides/acaricides/nematicides:
  abamectin, acephate, acetamiprid, acrinathrin, alanycarb, aldicarb, aldoxycarb, alpha-cypermethrin, alphamethrin, amitraz, avernectin, AZ 60541, azadirachtin, azamethiphos, azinphos A, azinphos M, azocyclotin,
  *Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn, eflusilanate, emamectin, empenthrin, endosulfan, Entomopfthora spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, isazofos, isofenphos, isoxathion, ivermectin, nuclear polyhedrosis viruses, lambda-cyhalothrin, lufenuron, malathion, mecarbam, metaldehyde, methamidophos, *Metharhizium anisopliae, Metharhizium flavoviride*, methidathion, methiocarb, methomyl, methoxyfenozide, metolcarb, metoxadiazone, mevinphos, milbemectin, monocrotophos, naled, nitenpyram, nithiazine, novaluron, omethoate, oxamyl, oxydemethon M,

*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propoxur, prothiofos, prothoate, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, sulfotep, sulprofos, tau-fluvalinate, tebufenozide, tebufenpyrad, tebupirimiphos, teflubenzuron, tefluthrin, temephos, temivinphos, terbufos, tetrachlorvinphos, thetacypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii*,

YI 5302, zeta-cypermethrin, zolaprofos, (1R-cis)-[5-(phenylmethyl)-3-furanyl]-methyl-3-[(dihydro-2-oxo-3(2H)-furanylidene)-methyl]-2,2-dimethylcyclopropanecarboxylate, (3-phenoxyphenyl)-methyl-2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl)phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate, 4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy-2-(3,4-dichlorophenyl)-3(2H)-pyridazinone,

*Bacillus thuringiensis* strain EG-2348,

[2-benzoyl-1-(1,1-dimethylethyl)-hydrazinobenzoic acid, 2,2-dimethyl-3-(2,4-dichlorophenyl)-2-oxo-1-oxaspiro[4.5]dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N"-nitroguanidine, N-methyl-N'-(1-methyl-2-propenyl)-1,2-hydrazinedicarbothioamide, N-methyl-N'-2-propenyl-1,2-hydrazinedicarbothioamide, O,O-diethyl [2-(dipropylamino)-2-oxoethyl]-ethylphosphoramidothioate.

It is also possible to admix other known active compounds, such as herbicides, fertilizers and growth regulators.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and stored products pests, the active compound is distinguished by an excellent residual action on wood and clay as well as a good stability to alkali on limed substrates.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, Haematopinus spp., Linognathus spp., Pediculus spp., Phtirus spp. and Solenopotes spp.

From the order of the Mallophagida and the suborders Amblycerina and Ischnocerina, for example, Trimenopon spp., Menopon spp., Trinoton spp., Bovicola spp., Wemeckiella spp., Lepikentron spp., Damalina spp., Trichodectes spp. and Felicola spp.

From the order of the Diptera and the suborders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example *Blatta orientalis, Periplaneta americana, Blattela germanica* and Supella spp.

From the subclass of the Acaria (Acarida) and the orders of the Meta- and Mesostigmata, for example, Argas spp., Ornithodorus spp., Otobius spp., Ixodes spp., Amblyomma spp., Boophilus spp., Dermacentor spp., Haemophysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) und Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

The active compounds according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds according to the invention also have a strong insecticidal action against insects which destroy industrial materials.

The following insects may be mentioned as examples and as preferred—but without a limitation:

Beetles, such as

*Hylotrupes bajulus, Chlorophorus pilosis, Anobium punctatum, Xestobium rufovillosum, Ptilinus pecticomis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis,* Xyleborus spec. Tryptodendron spec. *Apate monachus, Bostrychus capucins, Heterobostrychus brunneus,* Sinoxylon spec. *Dinoderus minutus.*

Hymenopterons, such as

*Sirex juvencus, Urocerus gigas, Urocerus gigas taignus, Urocerus augur.*

Termites, such as

*Kalotermes flavicollis, Cryptotermes brevis, Heterotermnes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccarina.*

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agent according to the invention or mixtures comprising this are to be understood as meaning, for example:

building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, providing that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of, or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl)adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone. Possible solvents or diluents are, in particular, also water, if appropriate as a mixture with one or more of the above-mentioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners may be insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyfenozide and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The compounds according to the invention can at the same time be employed for protecting objects which come into contact with saltwater or brackish water, such as hulls, screens, nets, buildings, moorings and signaling systems, against fouling.

Fouling by sessile Oligochaeta, such as Serpulidae, and by shells and species from the Ledamorpha group (goose barnacles), such as various Lepas and Scalpellum species, or by species from the Balanomorpha group (acorn barnacles), such as Balanus or Pollicipes species, increases the frictional drag of ships and, as a consequence, leads to a marked increase in operation costs owing to higher energy consumption and additionally frequent residence in the dry dock.

Apart from fouling by algae, for example Ectocarpus sp. and Ceramium sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bis-dimethyldithiocarbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:
algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;
fungicides such as
benzo[b]thiophenecarboxylic acid cyclohexylamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole;
molluscicides such as
fentin acetate, metaldehyde, methiocarb, niclosamid, thiodicarb and trimethacarb;
or conventional antifouling active compounds such as
4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleimide.

The antifouling compositions used comprise the active compound according to the invention of the compositions according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730–732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colourants which are preferably insoluble in salt water. Paints may furthermore comprise materials such as colophonium to allow a controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus*, Bryobia spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, Avicullariidae, Araneidae.

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus*, Polydesmus spp.

From the order of the Chilopoda, for example, Geophilus spp.

From the order of the Zygentoma, for example, Ctenolepisma spp., *Lepisma saccharina, Lepismodes inquilinus.*

From the order of the Blattaria, for example, *Blatta orientalies, Blattella germanica, Blattella asahinai, Leucophaea maderae*, Panchlora spp., Parcoblatta spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, Kalotermes spp., Reticulitermes spp.

From the order of the Psocoptera, for example, Lepinatus spp., Liposcelis spp.

From the order of the Coleptera, for example, Anthrenus spp., Attagenus spp., Dermestes spp., *Latheticus oryzae*, Necrobia spp., Ptinus spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus*, Anopheles spp., *Calliphora erythrocephala, Chrysozona pluvialis, Culex quinquefasciatus, Culex pipiens, Culex tarsalis*, Drosophila spp., *Fannia canicularis, Musca domestica*, Phlebotomus spp., *Sarcophaga carnaria*, Simulium spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis,* Paravespula spp., *Tetramorium caespitum.*

From the order of the Anoplura, for example, *Pediculus humanus capitis, Pediculus humanus corporis, Phthirus pubis.*

From the order of the Heteroptera, for example, *Cimex hemipterus, Cimex lectularius, Rhodinus prolixus, Triatoma infestans.*

In the field of household insecticides, they are used alone or in combination with other suitable active compounds, such as phosphoric acid esters, carbamates, pyrethroids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

The active compounds according to the invention can be used as defoliants, desiccants, haulm killers and, especially, as weed killers. Weeds in the broadest sense are understood to mean all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindemia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.

Dicotyledonous crops of the genera: Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.

Monocotyledonous weeds of the genera: Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.

Monocotyledonous crops of the genera: Allium, Ananas, Asparagus, Avena, Hordeum, Oryza, Panicum, Saccharum, Secale, Sorghum, Triticale, Triticum, Zea.

However, the use of the active compounds according to the invention is in no way restricted to these genera, but also extends in the same manner to other plants.

The active compounds according to the invention are suitable, depending on the concentration, for the total control of weeds, for example on industrial terrain and rail tracks, and on paths and areas with and without tree plantings. Similarly, the active compounds according to the invention can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds according to the invention have strong herbicidal activity and a broad active spectrum when used on the soil and on above-ground parts of plants. To a certain extent they are also suitable for the selective control of monocotyledonous and dicotyledonous weeds in monocotyledonous and dicotyledonous crops, both by the pre-emergence and by the post-emergence method.

At certain concentrations or application rates, the active compounds according to the invention can also be employed for controlling animal pests and fungal or bacterial plant diseases. If appropriate, they can also be used as intermediates or precursors for the synthesis of other active compounds.

All plants and plant parts can be treated in accordance with the invention. In the present context, plants are to be understood as meaning all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on and, in the case of propagation material, in particular in the case of seeds, also by applying one or more coats.

The active compounds can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is to say, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are: for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colourants such as inorganic pigments, for example iron oxide, titanium oxide and Prussian Blue, and organic colourants such as alizarin colourants, azo colourants and metal phthalocyanine colourants, and trace nutrients such as salts of iron, manganese, boron, copper, cobalt, molybdenum and zinc.

The formulations generally comprise between 0.1 and 95% by weight of active compound, preferably between 0.5 and 90%.

For controlling weeds, the active compounds according to the invention, as such or in their formulations, can also be used as mixtures with known herbicides and/or substances which improve the compatibility with crop plants ("safeners"), finished formulations or tank mixes being possible. Also possible are mixtures with weed-killers comprising one or more known herbicides and a safener.

Possible components for the mixtures are known herbicides, for example acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, BAS-662H, beflubutamid, benazolin (-ethyl), benfuresate, bensulfuron (-methyl), bentazon, benzfendizone, benzobicyclon, benzofenap, benzoylprop(-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (-P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuiron (-methyl), ethofumesate, ethoxyfen, ethoxysulfuron, etobenzanid, fenoxaprop (-P-ethyl), fentrazamide, flamprop (-isopropyl, -isopropyl-L, -methyl), flazasulfuron, florasulam, fluazifop (-P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, -P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesotrione, metamitron, metazachlor, methabenzthiazuron, metobenzuron, metobromuron, (alpha-) metolachlor, metosulam, metoxuron, metribuzin, metsulfuiron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, picolinafen, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalid, pyriminobac (-methyl), pyrithiobac (-sodium), quinchlorac, quinmerac, quinoclamine, quizalofop (-P-ethyl, -P-teftiryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin, trifloxysulfuron, triflusulfuron (-methyl), tritosulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in a customary manner, for example by watering, spraying, atomizing or broadcasting.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention is illustrated by the examples below.

PREPARATION EXAMPLES

Example I-1-1

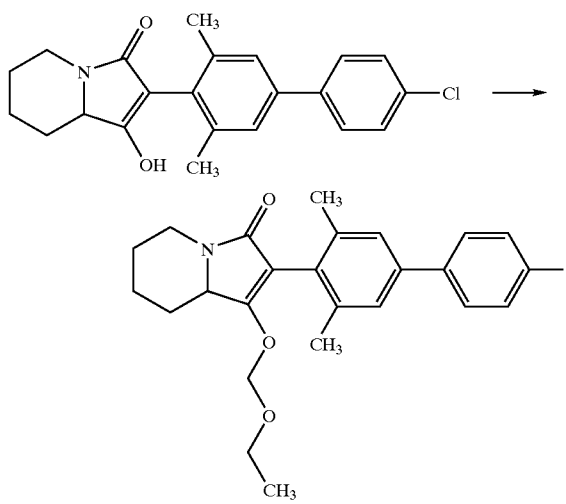

Example I-1

At 0° C., 0.29 g of chloromethyl ethyl ether dissolved in 5 ml of absolute ethyl acetate is added to a solution of the compound of the formula II-1 (known from DE 19 808 261.4) (1.1 g) in 30 ml of absolute ethyl acetate, the mixture is stirred at room temperature while the reaction is monitored by TLC and is concentrated and the residue is chromatographed on silica gel (n-hexane:ethyl acetate 2:1). 0.98 g (77%) of the compound I-1-1 shown above is isolated (solid, m.p.: 169° C.).

The compounds below were prepared analogously to Example I-1-1 and in accordance with the general statements on the preparation of compounds of the formula I-1.

TABLE 183

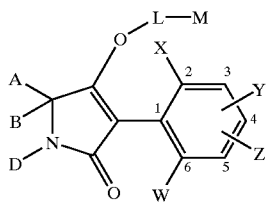

(I-1)

| Ex.-No. | W | X | Y | Z | D | A | B | L | M | m.p. ° C. |
|---|---|---|---|---|---|---|---|---|---|---|
| I-1-2 | CH₃ | CH₃ | 4-(4-Cl-C₆H₄)- | H | —(CH₂)₄— | H | —CH₂— | —N(CH₃)—CO₂CH₃ | Oil |
| I-1-3 | CH₃ | CH₃ | 4-(4-Cl-C₆H₄)- | H | —(CH₂)₄— | H | —CH₂— | —CO—(4-Cl-C₆H₄) | |
| I-1-4 | CH₃ | CH₃ | 4-(4-Cl-C₆H₄)- | H | i-C₃H₇ | H | H | —CH₂ | —OC₂H₅ | 115 |
| I-1-5 | CH₃ | CH₃ | 4-(4-Cl-C₆H₄)- | H | i-C₃H₇ | H | H | —CH₂ | —CO—CH₃ | 174 |
| I-1-6 | CH₃ | CH₃ | 3-(4-Cl-C₆H₄)- | H | H | —CH₂—O—(CH₂)₃— | CH₂ | —OC₂H₅ | Oil |

Example I-2-1

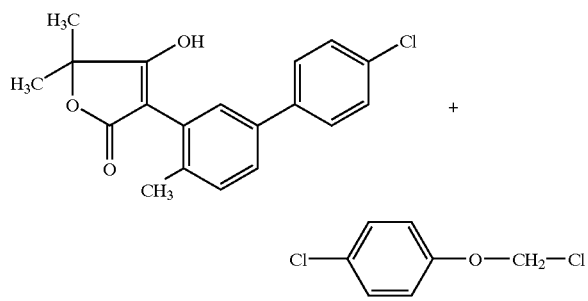

is stirred overnight and then washed with 10% strength citric acid and then with 10% aqueous sodium hydroxide solution and dried, the solvent is evaporated under reduced pressure and the residue is chromatographed on silica gel using the mobile phase methylene chloride. 0.39 g(+e,dus +e,cir +ee 21% of theory) of the compound I-2-1 shown above is isolated.

$^1$H-NMR (300 MHz, CDCl$_3$): δ=1.48 (s, 3H, CH$_3$), 1.52 (s, 3H, CH$_3$), 2.25 (s, 3H, Ar—C<u>H</u>$_3$), 5.5 (m, 2H, O—C<u>H</u>$_2$-O), 6.9 ("d", 2H, ArH), 7.25–7.65 (m, 9H, Ar<u>H</u>) ppm.

The compounds below were prepared analogously to Example I-2-1 and in accordance with the general statements on the preparation of compounds of the formula I-2.

TABLE 184

(I-2)

| Ex.-No. | W | X | Y | Z | A | B | L | M | m.p. ° C. |
|---|---|---|---|---|---|---|---|---|---|
| I-2-2 | H | CH$_3$ | 5—(Cl—⌬—) | H | CH$_3$ | CH$_3$ | —CH$_2$— | —C≡CH | Oil |
| I-2-3 | H | CH$_3$ | 5—(Cl—⌬—) | H | CH$_3$ | CH$_3$ | —CH$_2$— | —⌬ | Oil |

Example II-2

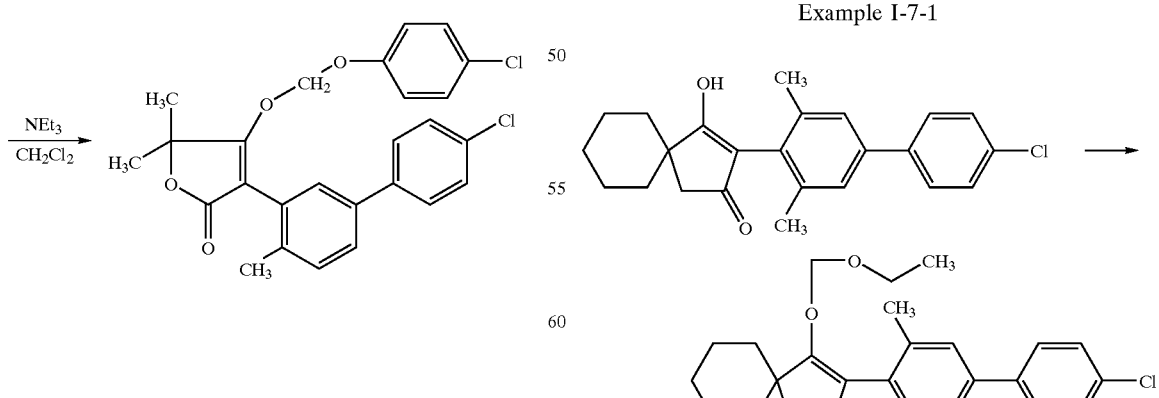

0.4 g of triethylamine is added to 0.98 g of the compound of the formula II-2 (known from DE 19 813 354.5) in 20 ml of anhydrous methylene chloride and, at 0–10° C., chloromethyl 4-chlorophenyl ether is added dropwise. The mixture

Example II-7

At 0° C., 0.24 ml of chloromethyl ethyl ether, dissolved in 3 ml of ethyl acetate, is added to a solution of the compound of the formula II-7 (known from DE 19 808 261.4) (1.0 g; 2.6 mmol) in 10 ml of ethyl acetate and triethylamine (0.36 ml; 2.6 mmol), and the mixture is stirred at room temperature for 8 h. The precipitate is filtered off and washed with ethyl acetate and the filtrate is then washed with sodium chloride solution, dried and concentrated.

1 g (88%) of the compound I-7-1 shown above is isolated (oil).

$^1$H-NMR (400 MHz, $d_6$-DMSO) δ=1,15–1.85 (m, 10H, $(CH_2)_5$), 2.09, 2.12 (2s, 6H, $CH_3$), 3.57 (q; 2H, O—$CH_2CH_3$); 5.32 (s, 2H, O—$CH_2$-O) 7.48 ("d"(AA', BB'), 2H, Ar—H), 7.67 ("d"(AA'BB'), 2H, Ar—H) ppm.

The compounds below were prepared analogously to Example I-7-1 and in accordance with the general statements on the preparation of the compounds of formula I-7.

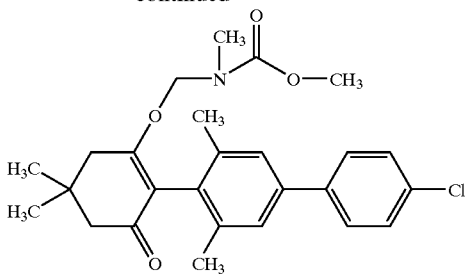

Example II-8

At 0° C., methyl N-chloromethyl-N-methyl-methyl-carbamate (0.58 ml; 4.2 mmol) dissolved in 3 ml of dichloromethane, is added to a solution of the compound of the formula II-8 (known from DE 198 08261.4) (1.0 g; 2.8

TABLE 185

(I-7)

| Ex.-No. | W | X | Y | Z | A | B | L | M | m.p. °C. |
|---|---|---|---|---|---|---|---|---|---|
| I-7-2 | H | $CH_3$ | 5—(Cl—⌬—) | 4-$CH_3$ | —$(CH_2)_5$— | —$CH_2$— | $OC_2H_5$ | | Oil |
| I-7-3 | $CH_3$ | $CH_3$ | 4—(Cl—⌬—) | H | —$(CH_2)_5$— | —$CH_2$— | —N(—i-$C_3H_7$)($CO_2C_2H_5$) | | Oil |
| I-7-4 | $CH_3$ | $CH_3$ | 3—(Cl—⌬—) | 4-$CH_3$ | —$(CH_2)_5$— | —$CH_2$— | —N(—$CH_3$)($CO_2CH_3$) | | Oil |
| I-7-5 | H | $CH_3$ | 4—(Cl—⌬—) | 5-$CH_3$ | —$(CH_2)_5$— | —$CH_2$— | —O-i-$C_4H_9$ | | Oil |
| I-7-6 | H | $CH_3$ | 4—(Cl—⌬—) | 5-$CH_3$ | —$(CH_2)_5$— | —$CH_2$— | —N(—$CH_3$)($CO_2CH_3$) | | Oil |

Example I-8-1

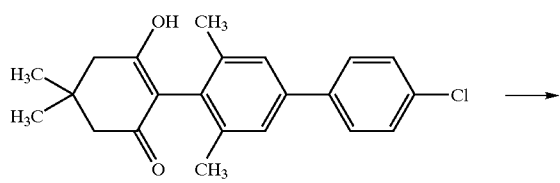

mmol) in 10 ml of dichloromethane and triethylamine (0.58 g; 4.2 mmol), and the mixture is stirred at room temperature for 8 h. The reaction solution is washed with 10% strength citric acid and extracted with dichloromethane. The organic phase is washed with 1N sodium hydroxide solution, extracted with dichloromethane and dried, and the organic phase is concentrated.

1.15 g (90%) of the compound I-8-1 shown above are isolated (oil).

$^1$H-NMR (400 MHz, $d_6$-DMSO): δ=1.16 (s, 6H, C($CH_3$)$_2$); 2.04 (s, 6H, Ar$CH_3$), 3.6 (s, 3H, O$CH_3$), 5.16 (s, 2H,

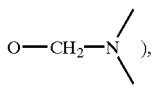

7.3 (s, 2H, ArH), 7.48 ("d"(AA'BB'), 2H, ArH), 7.67 ("d" (AA'BB'), 2H, Ar—H)ppm.

The following compounds were prepared analogously to Example (I-8-1) and in accordance with the general statements on the preparation of compounds of the formula (I-8):

In this test, for example, the following compounds of the Preparation Examples show good activity: I-7-2, I-8-2, I-8-1, I-8-5.

Example 2
*Spodoptera frugiperda* Test

Solvent: 7 parts by weight of dimethylformamide
Emulsifier: 1 parts by weight alkylaryl polyglycol ether To produce a suitable preparation of active compound, 1 part by weight of active compound is mixed with the stated

TABLE 186

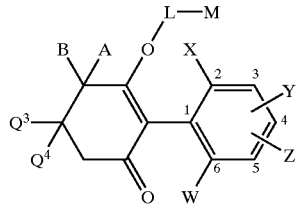

(I-8)

| Ex. No. | W | X | Y | Z | A | B | $Q^3$ | $Q^4$ | L | M | m.p. °C. |
|---|---|---|---|---|---|---|---|---|---|---|---|
| I-8-2 | H | CH$_3$ | 4-(Cl-⌬-) | 5-CH$_3$ | H | H | CH$_3$ | CH$_3$ | —CH$_2$— | —OC$_2$H$_5$ | Oil |
| I-8-3 | CH$_3$ | CH$_3$ | 4-(Cl-⌬-) | H | H | H | CH$_3$ | CH$_3$ | —CH$_2$— | —O-i-C$_4$H$_9$ | Oil |
| I-8-4 | H | CH$_3$ | 4-(Cl-⌬-) | 5-CH$_3$ | H | H | CH$_3$ | CH$_3$ | —CH$_2$— | —N(i-C$_3$H$_7$)(CO$_2$C$_2$H$_5$) | Oil |
| I-8-5 | H | CH$_3$ | 5-(Cl-⌬-) | 4-CH$_3$ | H | H | CH$_3$ | CH$_3$ | —CH$_2$— | —N(i-C$_3$H$_7$)(CO$_2$C$_2$H$_5$) | Oil |
| I-8-6 | CH$_3$ | CH$_3$ | 5-(Cl-⌬-) | 4-CH$_3$ | H | H | CH$_3$ | CH$_3$ | —CH$_2$— | —O-i-C$_4$H$_9$ | Oil |

USE EXAMPLES

Example 1
Phaedon-larvae Test

Solvent: 7 parts by weight of dimethylformamide
Emulsifier: 1 part by weight of alkylaryl polyglycol ether To produce a suitable preparation of active compound, 1 part by weight of active compound is mixed with a stated amount of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the armyworm (*Spodoptera frugiperda*) while the leaves are still moist.

After the desired period of time, the kill in % is determined. 100% means that all caterpillars have been killed; 0% means that none of the caterpillars have been killed.

In this test, for example, the following compounds of the Preparation Examples show good activity: I-8-5, I-8-6.

Example 3
Tetranychus Test (OP-resistant/dip Treatment)

Solvent: 7 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*), which are heavily infested by all stages of the greenhouse red spider mite (*Tetranychus urticae*) are dipped into a preparation of active compound of the desired concentration.

After the desired period of time, the effect in % is determined. 100% means that all spider mites have been killed; 0% means that none of the spider mites have been killed.

In this test, for example, the following compounds of the Preparation Examples show good activity: I-7-2, I-8-5, I-7-4.

Example 4

Meloidogyne Test

Solvent: 7 parts by weight of dimethylformamide

Emulsifier: 1 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

Containers are filled with sand, solution of active compound, Meloidogyne incognita-egg/larvae suspension and lettuce seeds. The lettuce seeds germinate and the plants develop. On the roots, galls are formed.

After the desired period of time, the nematicidal action is determined in % by the gall formation. 100% means that no galls were found; 0% means that the number of galls on the treated plants corresponds to that of the untreated control.

In this test, for example, the following compound of the Preparation Examples show good activity: I-7-3, I-8-1, I-8-5, I-7-4.

Example 5

Pre-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, with the stated amounts of emulsifiers added and the concentrate is diluted with water to the desired concentration.

Seeds of the test plants are sown in normal soil. After about 24 hours, the soil is sprayed with the preparation of active compound such that the particular amounts of active compound desired are applied per unit area. The concentration of the spray liquor is chosen such that the particular amounts of active compound desired are applied in 1000 l of water/ha.

After 3 weeks, the degree of damage to the plants is rated in % damage in comparison to the development of the untreated control.

The figures denote:

0%=no effect (like untreated control)

100%=total destruction

Pre-emergence/greenhouse

| | g ai./ha | *Avena fatua* | Echinochloa | Setaria | Sinapis |
|---|---|---|---|---|---|
| Ex. I-7-3 | 250 | 95 | 100 | 100 | 70 |

| | g ai./ha | Alopecurus | *Avena fatua* | Echinochloa | Setaria | Abutilon |
|---|---|---|---|---|---|---|
| Ex. I-8-1 | 250 | 90 | 90 | 100 | 100 | 80 |

Example 6

Post-emergence Test

Solvent: 5 parts by weight of acetone

Emulsifier: 1 parts by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants of a height of 5–15 cm are sprayed with the preparation of active compound such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:

0% no effect (like untreated control)

100%=total destruction

Post-emergence/greenhouse

| | g ai./ha | *Avena fatua* | Echinochloa | Setaria | Sinapis |
|---|---|---|---|---|---|
| Ex. I-7-3 | 250 | 80 | 100 | 100 | 80 |

| | g ai./ha | Sugar beet | Alopecurus | Echinochloa | Setaria |
|---|---|---|---|---|---|
| Ex. I-8-1 | 250 | 0 | 80 | 100 | 100 |

Example 7

Cockroach Test

Test animals: *Blattella germanica* or *Periplaneta americana*

Solvent: Dimethyl sulphoxide 20 mg of active compound are dissolved in 1 ml of dimethyl sulphoxide, more dilute concentrations are prepared by dilution with dist. $H_2O$.

5 ml of this preparation of active compound are pipetted on baked biscuit wafers (Ø 9.5 cm) in petri dishes of corresponding size. The biscuit wafers are dried and then populated with four test animals and covered.

After 7 days of storage in a controlled-environment room, the kill rate is determined.

100% means that all cockroaches have been killed, 0% means that none of the cockroaches have been killed.

In this test, for example, the following compounds of Preparation Examples I-7-2 and I-8-5 show, at an exemplary active compound concentration of 100 ppm, a kill of 100%.

Example 8

Cockroach Test

Test animals: *Blattella germanica* or *Periplaneta americana*

Solvent: Dimethyl sulphoxide 20 mg of active compound are dissolved in 1 ml of dimethyl sulphoxide, more dilute concentrations are prepared by dilution with dist. $H_2O$.

4 test animals are dipped for 1 minute into the preparation of active compound to be tested. The test animals are transferred into plastic beakers and kept in a controlled-environment room for 7 days, after which the kill rate is determined.

100% means that all cockroaches have been killed, 0% means that none of the cockroaches have been killed.

In this test, for example, the following compounds of Preparation Examples I-7-2 and I-8-5 show, at an exemplary active compound concentration of 100 ppm, a kill of 100% (I-7-2) and 75% (I-8-5), respectively.

What is claimed is:

1. A compound of the formula (I)

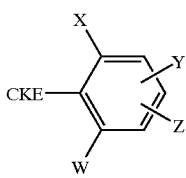
(I)

wherein

W represents hydrogen, halogen, alkyl, alkoxy, alkenyloxy, halogenoalkyl, halogenoalkoxy, halogenoalkenyloxy, nitro or cyano, X represents halogen, alkyl, alkoxy, alkenyloxy, alkylthio, alkylsulphinyl, alkylsulphonyl, halogenoalkyl, halogenoalkoxy, halogenoalkenyloxy, nitro, cyano or optionally substituted phenyl, phenoxy, phenylthio, phenylalkoxy or phenylalkylthio, Y represents optionally substituted cycloalkyl, aryl or hetaryl, Z represents hydrogen, halogen, alkyl, alkoxy, halogenoalkyl or halogenoalkoxy, CKE represents one of the groups

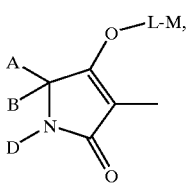
(1)

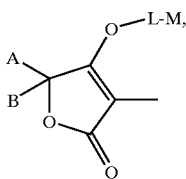
(2)

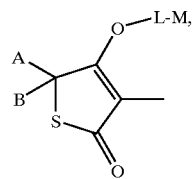
(3)

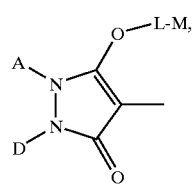
(4)

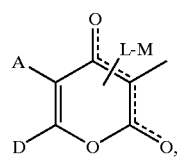
(5)

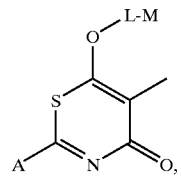
(6)

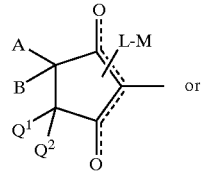
or (7)

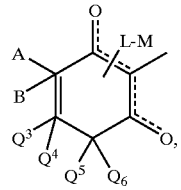
(8)

A represents hydrogen, optionally halogen-substituted alkyl, alkenyl, alkoxyalkyl, polyalkoxyalkyl, alkylthioalkyl, saturated or unsaturated, optionally substituted cycloalkyl, with optionally at least one ring atom replaced by a heteroatom, or optionally halogen-, alkyl-, halogenoalkyl, alkoxy-, halogenoalkoxy-, cyano- or nitro-substituted aryl, arylalkyl or hetaryl, B represents hydrogen, alkyl or alkoxyalkyl, or A and B together with the carbon atom to which they are attached represent a saturated or unsaturated, unsubstituted or substituted cyclic ring which optionally contains at least one heteroatom, D represents hydrogen or an optionally substituted radical from the group consisting of alkyl, alkenyl, alkynyl, alkoxyalkyl, polyalkoxyalkyl, alkylthioalkyl, saturated or unsaturated cycloalkyl, in which optionally one or more ring members are replaced by heteroatoms, arylalkyl, aryl, hetarylalkyl or hetaryl or A and D together with the atoms to which they are attached represent a saturated or unsaturated cyclic ring which is unsubstituted or substituted in the A,D moiety and optionally contains at least one (in the case of CKE=(4) further) heteroatom, or A and $Q^1$ together represent alkanediyl or alkenediyl, which is optionally substituted by optionally substituted alkyl, hydroxyl, alkoxy, alkylthio, cycloalkyl, benzyloxy or aryl, or $Q^1$ represents hydrogen or alkyl, $Q^2$, $Q^4$, $Q^5$ and $Q^6$ Independently represent hydrogen or alkyl, $Q^3$ represents hydrogen, alkyl, alkoxyalkyl, alkylthioalkyl, optionally substituted cycloalkyl (in which optionally one methylene group is replaced by oxygen or sulphur) or optionally substituted phenyl, or $Q^3$ and $Q^4$ together with the carbon atom to which they are attached represent a saturated or unsaturated, unsubstituted or substituted cyclic ring which optionally contains a heteroatom, L represents an alkanediyl group, M represents one of the groups below:
CN;

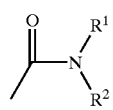

—$CO_2R^2$, —$OR^2$, —$SR^2$, —$COR^3$,

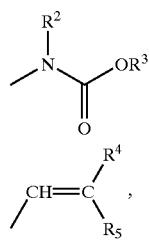 

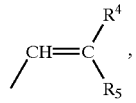 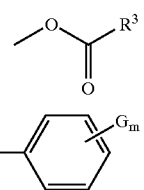 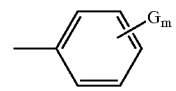

in which
$R^1$ represents hydrogen or alkyl,
$R^2$ represents optionally substituted alkyl, alkenyl, alkynyl, cycloalkyl, alkoxyalkyl, alkylthioalkyl, aryl or aralkyl,
$R^3$ represents optionally substituted alkyl, aryl or aralkyl,
$R^4$ represents hydrogen, halogen, optionally substituted alkyl or phenyl,
$R^5$ represents hydrogen, halogen or optionally substituted alkyl,
G represents halogen, alkyl, alkoxy, halogenoalkyl, halogenoalkoxy, cyano or nitro and
m represents the number 0, 1, 2 or 3.

2. The compound of claim 1, wherein

W represents hydrogen, halogen, $C_1$–$C_6$-alkyl, $C_1$–$C_6$-alkoxy, $C_1$–$C_6$-halogenoalkyl, $C_1$–$C_6$-halogenoalkoxy, nitro or cyano, X represents halogen, $C_1$–$C_6$-alkyl, $C_1$–$C_6$-halogenoalkyl, $C_1$–$C_6$-alkoxy, $C_3$–$C_6$-alkenyloxy, $C_1$–$C_6$-alkylthio, $C_1$–$C_6$-alkylsulphinyl, $C_1$–$C_6$-alkylsulphonyl, $C_1$–$C_6$-halogenoalkoxy, $C_3$–$C_6$-halogenoalkenyloxy, nitro, cyano or optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenoxy, phenylthio, benzyloxy or benzylthio, Y represents one of the radicals

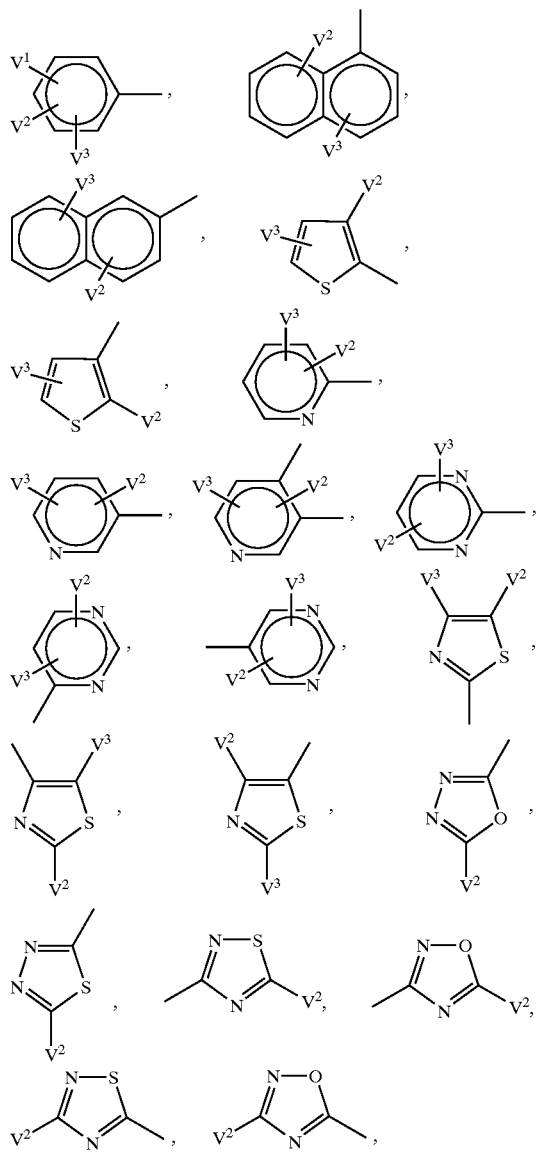

wherein $V^1$ represents hydrogen, halogen, $C_1$–$C_{12}$-alkyl, $C_1$–$C_6$-alkoxy, $C_1$–$C_4$-halogenoalkyl, $C_1$–$C_4$-halogenoalkoxy, nitro, cyano or phenyl, phenoxy, phenoxy-$C_1$–$C_4$-alkyl, phenyl-$C_1$–$C_4$-alkoxy, phenylthio-$C_1$–$C_4$-alkyl or phenyl-$C_1$–$C_4$-alkylthio, which is optionally mono- or polysubstituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano, $V^2$ and $V^3$ independently represent hydrogen, halogen, $C_1$–$C_6$-alkyl, $C_1$–$C_6$-alkoxy, $C_1$–$C_4$-halogenoalkyl or $C_1$–$C_4$-halogenoalkoxy, Z represents hydrogen, halogen, $C_1$–$C_6$-alkyl, $C_1$–$C_6$-halogenoalkyl, $C_1$–$C_6$-alkoxy or $C_1$–$C_6$-halogenoalkoxy, CKE represents one of the groups

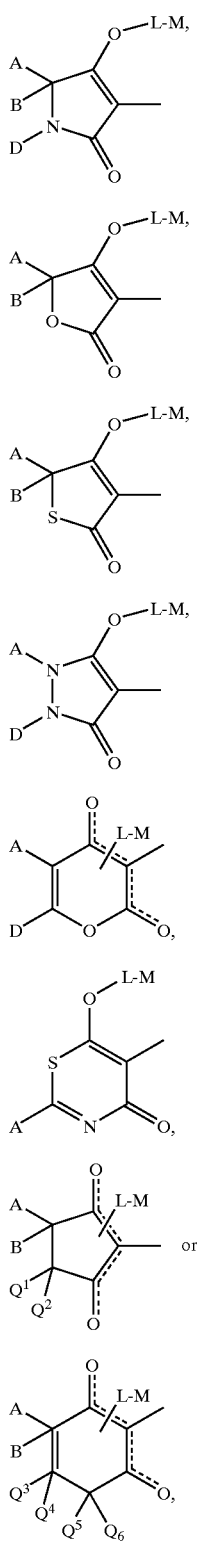

wherein
A represents hydrogen or optionally halogen-substituted $C_1$–$C_{12}$-alkyl, $C_3$–$C_8$-alkenyl, $C_1$–$C_{10}$-alkoxy-$C_1$–$C_8$-alkyl, di-, tri- or tetra-$C_1$–$C_8$-alkoxy-$C_1$–$C_8$-alkyl, $C_1$–$C_{10}$-alkylthio-$C_1$–$C_6$-alkyl, optionally halogen-, $C_1$–$C_6$-alkyl- or $C_1$–$C_6$-alkoxy-substituted $C_3$–$C_8$-cycloalkyl, in which optionally one or two not directly adjacent ring members are replaced by oxygen and/or sulphur, or represents optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano- or nitro-substituted $C_6$- or $C_{10}$-aryl, hetaryl having 5 or 6 ring atoms or $C_6$- or $C_{10}$-aryl-$C_1$–$C_6$-alkyl, B represents hydrogen, $C_1$–$C_{12}$-alkyl or $C_1$–$C_8$-alkoxy-$C_1$–$C_6$-alkyl, or A, B and the carbon atom to which they are attached represent saturated $C_3$–$C_{10}$-cycloalkyl or unsaturated $C_5$–$C_{10}$-cycloalkyl in which optionally one ring member is replaced by oxygen or sulphur and which are optionally mono- or disubstituted by $C_1$–$C_8$-alkyl, $C_3$–$C_{10}$-cycloalkyl, $C_1$–$C_8$-halogenoalkyl, $C_1$–$C_8$-alkoxy, $C_1$–$C_8$-alkylthio, halogen or phenyl, or A, B and the carbon atom to which they are attached represent $C_3$–$C_6$-cycloalkyl which is substituted by an alkylenediyl group which optionally contains one or two not directly adjacent oxygen and/or sulphur atoms or by an alkylenedioxyl or by an alkylenedithiol group which, together with the carbon atom to which they are attached, form a further five- to eight-membered ring, or A, B and the carbon atom to which they are attached represent $C_3$–$C_8$-cycloalkyl or $C_5$–$C_8$-cycloalkenyl in which two substituents together with the carbon atoms to which they are attached represent optionally $C_1$–$C_6$-alkyl-, $C_1$–$C_6$-alkoxy- or halogen-substituted $C_2$–$C_6$-alkanediyl, $C_2$–$C_6$-alkenediyl or $C_4$–$C_6$-alkanedienediyl in which optionally one methylene group is replaced by oxygen or sulphur, D represents hydrogen, optionally halogen-substituted $C_1$–$C_{12}$-alkyl, $C_3$–$C_8$-alkenyl, $C_3$–$C_8$-alkynyl, $C_1$–$C_{10}$-alkoxy-$C_2$–$C_8$-alkyl, poly-$C_1$–$C_8$-alkoxy-$C_2$–$C_8$-alkyl, $C_1$–$C_{10}$-alkylthio-$C_2$–$C_8$-alkyl, optionally halogen-, $C_1$–$C_4$-alkyl-, $C_1$–$C_4$-alkoxy- or $C_1$–$C_4$-halogenoalkyl-substituted $C_3$–$C_8$-cycloalkyl in which optionally one ring member is replaced by oxygen or sulphur or optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano- or nitro-substituted phenyl, hetaryl having 5 or 6 ring atoms, phenyl-$C_1$–$C_6$-alkyl or hetaryl-$C_1$–$C_6$-alkyl having 5 or 6 ring atoms, or A and D together represent optionally substituted $C_3$–$C_6$-alkanediyl or $C_3$–$C_6$-alkenediyl in which optionally one methylene group is replaced by oxygen or sulphur, a substituent selected from halogen, hydroxyl, mercapto or optionally halogen-substituted $C_1$–$C_{10}$-alkyl, $C_1$–$C_6$-alkoxy, $C_1$–$C_6$-alkylthio, $C_3$–$C_7$-cycloalkyl, phenyl or benzyloxy, or a further $C_3$–$C_6$-alkanediyl grouping, $C_3$–$C_6$-alkenediyl grouping or a butadienyl grouping, which is optionally substituted by $C_1$–$C_6$-alkyl or in which optionally two adjacent substituents together with the carbon atoms to which they are attached form a further saturated or unsaturated cyclic ring having 5 or 6 ring atoms (in the case of the compound of the formula (I-1), A and D together with the atoms to which they are attached represent, the groups AD-1 to AD-10), which may contain oxygen or sulphur, or which optionally contains one of the groups below

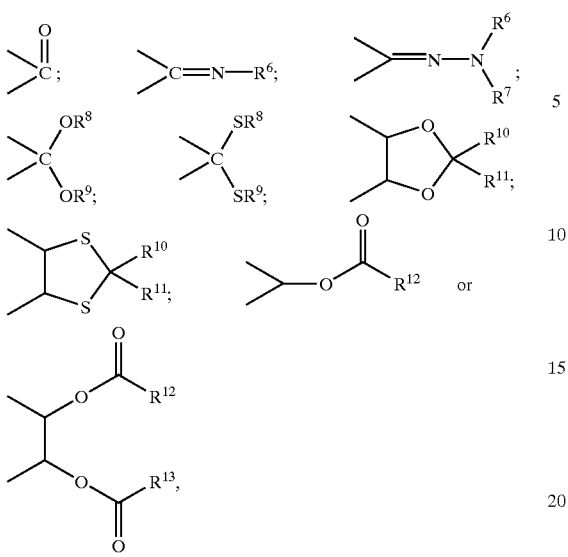

or

A and $Q^1$ together represent $C_3$–$C_6$-alkanediyl or $C_4$–$C_6$-alkenediyl, which is optionally mono- or disubstituted by a substituent selected from the group consisting of halogen, hydroxyl, of $C_1$–$C_{10}$-alkyl, $C_1$–$C_6$-alkoxy, $C_1$–$C_6$-alkylthio, $C_3$–$C_7$-cycloalkyl, which is optionally mono- to tri-substituted by halogens, and benzyloxy or phenyl, which is optionally mono- to tri-substituted by substituents selected from the group consisting of halogen, $C_1$–$C_6$-alkyl and $C_1$–$C_6$-alkoxy, which $C_3$–$C_6$-alkanediyl or $C_4$–$C_6$-alkenediyl optionally containing one of the groups below

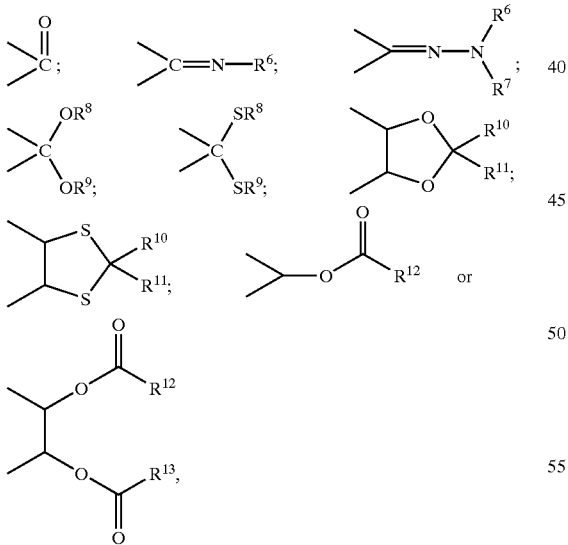

or is bridged by a $C_1$–$C_2$-alkanediyl group or by an oxygen atom or $Q^1$ represents hydrogen or $C_1$–$C_4$-alkyl, $Q^2$, $Q^4$, $Q^5$ and $Q^6$ independently represent hydrogen or $C_1$–$C_4$-alkyl, $Q^3$ represents hydrogen, $C_1$–$C_6$-alkyl, $C_1$–$C_6$-alkoxy-$C_1$–$C_2$-alkyl, $C_1$–$C_6$-alkylthio-$C_1$–$C_2$-alkyl, optionally $C_1$–$C_4$-alkyl- or $C_1$–$C_4$-alkoxy-substituted $C_3$–$C_8$-cycloalkyl, in which optionally one methylene group is replaced by oxygen or sulphur, or optionally halogen-, $C_1$–$C_4$-alkyl-, $C_1$–$C_4$-alkoxy-, $C_1$–$C_2$-halogenoalkyl, $C_1$–$C_2$-halogenoalkoxy-, cyano- or nitro-substituted phenyl, or $Q^3$ and $Q^4$ together with the carbon atom to which they are attached represent optionally $C_1$–$C_4$-alkyl-, $C_1$–$C_4$-alkoxy- or $C_1$–$C_2$-halogenoalkyl-substituted $C_3$–$C_7$-cycloalkyl in which optionally one ring member is replaced by oxygen or sulphur, L represents an alkanediyl group having 1 to 6 carbon atoms, M represents one of the groupings below:

CN;

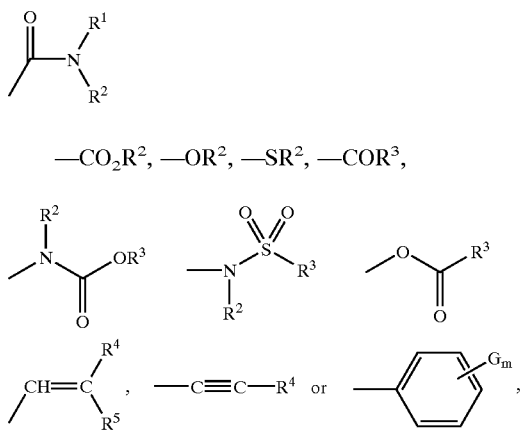

—$CO_2R^2$, —$OR^2$, —$SR^2$, —$COR^3$, $R^1$ represents hydrogen or $C_1$–$C_{12}$-alkyl, $R^2$ represents optionally halogen-substituted $C_1$–$C_{12}$-alkyl, $C_3$–$C_8$-alkenyl, $C_3$–$C_8$-alkynyl, $C_3$–$C_8$-cycloalkyl, $C_1$–$C_8$-alkoxy-$C_2$–$C_8$-alkyl, $C_1$–$C_8$-alkylthio-$C_2$–$C_8$-alkyl, represents optionally halogen-, nitro-, cyano-, $C_1$–$C_6$-alkoxy-, $C_1$–$C_6$-halogenoalkoxy-, $C_1$–$C_6$-alkylthio-, $C_1$–$C_6$-halogenoalkylthio-, $C_1$–$C_6$-alkyl- or $C_1$–$C_6$-halogenoalkyl-substituted phenyl or benzyl, $R^3$ represents optionally halogen-substituted $C_1$–$C_{12}$-alkyl or represents optionally halogen-, $C_1$–$C_6$-alkyl-, $C_1$–$C_6$-halogenoalkyl-, $C_1$–$C_6$-alkoxy- or $C_1$–$C_6$-halogenoalkoxy-substituted phenyl or benzyl, $R^4$ represents hydrogen, halogen, optionally halogen-substituted $C_1$–$C_6$-alkyl or optionally halogen-, $C_1$–$C_6$-alkyl-, $C_1$–$C_6$-alkoxyl-, $C_1$–$C_4$-halogenoalkyl-, $C_1$–$C_4$-halogenoalkoxy-, cyano- or nitro-substituted phenyl, $R^5$ represents hydrogen, halogen or optionally halogen-substituted $C_1$–$C_6$-alkyl, G represents halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, m represents the number 0, 1, 2 or 3, $R^6$ represents hydrogen, represents optionally halogen- substituted $C_1$–$C_8$-alkyl or $C_1$–$C_8$-alkoxy, represents optionally halogen-, $C_1$–$C_4$-alkyl- or $C_1$–$C_4$-alkoxy-substituted $C_3$–$C_8$-cycloalkyl, in which optionally one methylene group is replaced by oxygen or sulphur, or represents optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenyl-$C_1$–$C_4$-alkyl or phenyl-$C_1$–$C_4$-alkoxy, $R^7$ represents hydrogen or $C_1$–$C_8$-alkyl, or $R^6$ and $R^7$ together represent $C_4$–$C_6$-alkanediyl, $R^8$ and $R^9$ represent $C_1$–$C_6$-alkyl, or $R^8$ and $R^9$ together represent a $C_2$–$C_4$-alkanediyl radical which is optionally substituted by $C_1$–$C_6$-alkyl, $C_1$–$C_6$-halogenoalkyl or by optionally halogen-, $C_1$–$C_6$-alkyl-, $C_1$–$C_4$-halogenoalkyl-, $C_1$–$C_6$-alkoxy-, $C_1$–$C_4$-halogenoalkoxy-, nitro- or cyano-substituted phenyl, $R^{10}$ and $R^{11}$ independently represent hydrogen, represent optionally halogen-substituted $C_1$–$C_8$-alkyl or represent optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano- substituted phenyl, or $R^{10}$ and $R^{11}$ together with the carbon atom to which they are attached represent a carbonyl group or represent optionally halogen-, $C_1$–$C_4$-alkyl- or $C_1$–$C_4$-alkoxy-substituted $C_5$–$C_7$-cycloalkyl in which optionally one methylene group is replaced by oxygen or sulphur, $R^{12}$ and $R^{13}$ independently represent $C_1$–$C_{10}$-alkyl, $C_2$–$C_{10}$-alkenyl, $C_1$–$C_{10}$-alkoxy, $C_1$–$C_{10}$-alkylamino, $C_3$–$C_{10}$-alkenylamino, di-($C_1$–$C_{10}$-alkyl)amino or di-($C_3$–$C_{10}$-alkenyl)amino.

3. The compound of claim 1, wherein

W represents hydrogen, fluorine, chlorine, bromine, $C_1$–$C_4$-alkyl, $C_1$–$C_4$-alkoxy, $C_1$–$C_4$-halogenoalkyl, $C_1$–$C_4$-halogenoalkoxy, nitro or cyano, X represents fluorine, chlorine, bromine, $C_1$–$C_4$-alkyl, $C_1$–$C_4$-alkoxy, $C_3$–$C_4$-alkenyloxy, $C_1$–$C_4$-halogenoalkyl, $C_1$–$C_4$-halogenoalkoxy, $C_3$–$C_4$-halogenoalkenyloxy, nitro or cyano, Y represents one of the radicals

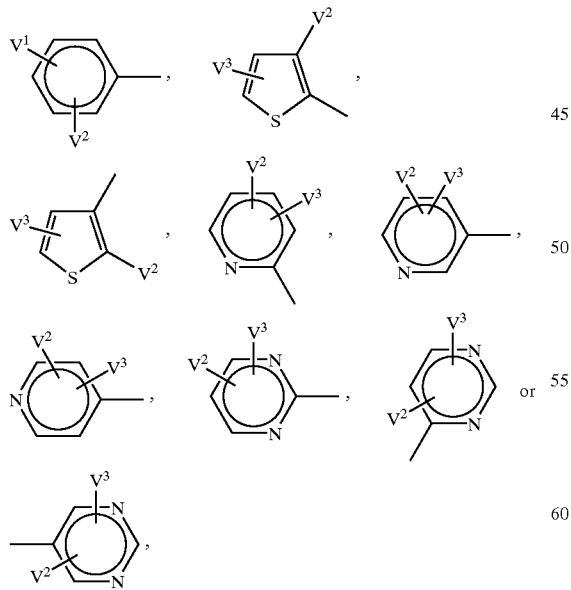

wherein $V^1$ represents hydrogen, fluorine, chlorine, bromine, $C_1$–$C_6$-alkyl, $C_1$–$C_4$-alkoxy, $C_1$–$C_2$-halogenoalkyl, $C_1$–$C_2$-halogenoalkoxy, nitro, cyano or represents phenyl, phenoxy, phenoxy-$C_1$–$C_2$-alkyl, phenyl-$C_1$–$C_2$-alkoxy, phenylthio-$C_1$–$C_2$-alkyl or phenyl-$C_1$–$C_2$-alkylthio, which is optionally mono- or dis-ubstituted by fluorine, chlorine, bromine, $C_1$–$C_4$-alkyl, $C_1$–$C_4$-alkoxy, $C_1$–$C_2$-halogenoalkyl, $C_1$–$C_2$halogenoalkoxy, nitro or cyano, $V^2$ and $V^3$ independently represent hydrogen, fluorine, chlorine, bromine, $C_1$–$C_4$-alkyl, $C_1$–$C_4$-alkoxy, $C_1$–$C_2$-halogenoalkyl or $C_1$–$C_2$-halogenoalkoxy, Z represents hydrogen, fluorine, chlorine, bromine, $C_1$–$C_4$-alkyl, $C_1$–$C_4$-halogenoalkyl, $C_1$–$C_4$-alkoxy or $C_1$–$C_4$-halogenoalkoxy, CKE represents one of the groups

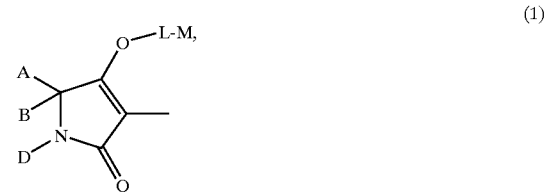

(1)

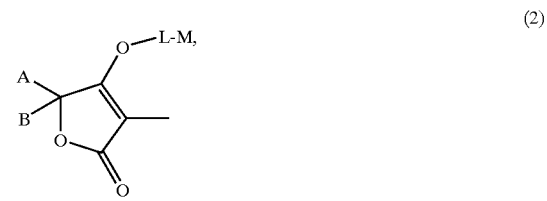

(2)

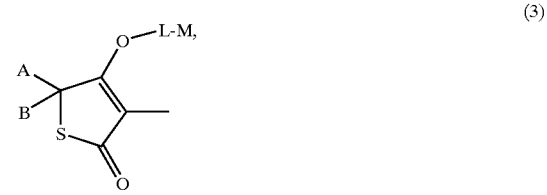

(3)

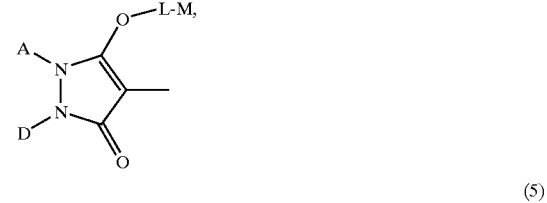

(4)

(5)

(6)

(7)

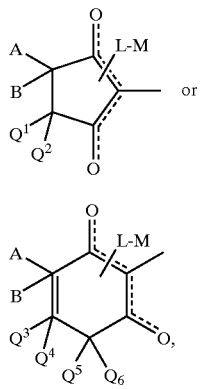

or (8)

wherein

A represents hydrogen, optionally fluorine- or chlorine-substituted $C_1$–$C_{10}$-alkyl, $C_1$–$C_8$-alkoxy-$C_1$–$C_6$-alkyl, optionally fluorine-, chlorine-, $C_1$–$C_4$-alkyl- or $C_1$–$C_4$-alkoxy-substituted $C_3$–$C_7$-cycloalkyl, in which optionally one ring member is replaced by oxygen or sulphur, or (but not in the case of the compounds of the formulae (I-5), (I-7) and (I-8)) optionally fluorine-, chlorine-, bromine-, $C_1$–$C_4$-alkyl-, $C_1$–$C_4$-halogenoalkyl-, $C_1$–$C_4$-alkoxy-, cyano-, nitro- or $C_1$–$C_4$-halogenoalkoxy-substituted phenyl, furanyl, pyridyl, imidazolyl, triazolyl, pyrazolyl, pyrimidyl, thiazolyl, thienyl or phenyl-$C_1$–$C_4$-alkyl, B represents hydrogen or $C_1$–$C_6$-alkyl, or A, B and the carbon atom to which they are attached represent saturated or unsaturated $C_5$–$C_7$-cycloalkyl in which optionally one ring member is replaced by oxygen or sulphur and which is optionally mono-substituted by $C_1$–$C_6$-alkyl, $C_5$–$C_8$-cycloalkyl, $C_1$–$C_3$-halogenoalkyl, $C_1$–$C_6$-alkoxy, fluorine, chlorine or phenyl, or A, B and the carbon atom to which they are attached represent $C_5$–$C_6$-cycloalkyl which is substituted by an alkylenediyl group which optionally contains one or two not directly adjacent oxygen or sulphur atoms or by an alkylenedioxyl or an alkylenedithiol group which, together with the carbon atom to which they are attached, form a further 5- or 6-membered ring, or A, B and the carbon atom to which they are attached represent $C_3$–$C_6$-cycloalkyl or $C_5$–$C_6$-cycloalkenyl in which two substituents together with the carbon atoms to which they are attached represent optionally $C_1$–$C_5$-alkyl-, $C_1$–$C_5$-alkoxy-, fluorine-, chlorine- or bromine-substituted $C_2$–$C_4$-alkanediyl, $C_2$–$C_4$-alkenediyl, in which optionally one methylene group is replaced by oxygen or sulphur, or butyldienediyl, D represents hydrogen, represents optionally fluorine- or chlorine-substituted $C_1$–$C_{10}$-alkyl, $C_3$–$C_6$-alkenyl, $C_1$–$C_8$-alkoxy-$C_2$–$C_6$-alkyl or $C_1$–$C_8$-alkylthio-$C_2$–$C_6$-alkyl, represents optionally fluorine-, chlorine-, $C_1$–$C_4$-alkyl-, $C_1$–$C_4$-alkoxy- or $C_1$–$C_2$-halogenoalkyl-substituted $C_3$–$C_7$-cycloalkyl, in which optionally one methylene group is replaced by oxygen or sulphur, or (but not in the case of the compounds of the formulae (I-1) and (I-4)) represents optionally fluorine-, chlorine-, bromine-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, furanyl, imidazolyl, pyridyl, thiazolyl, pyrazolyl, pyrimidyl, pyrrolyl, thienyl, triazolyl or phenyl-$C_1$–$C_4$-alkyl, or A and D together represent optionally substituted $C_3$–$C_5$-alkanediyl in which one methylene group may be replaced by a carbonyl group, oxygen or sulphur, possible substituents being hydroxyl, $C_1$–$C_6$-alkyl and $C_1$–$C_4$-alkoxy, or A and D (in the case of the compounds of the formula (I-1)) together with the atoms to which they are attached represent one of the groups AD-1 to AD-10:

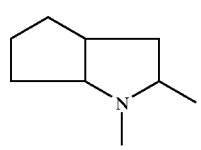
AD-1

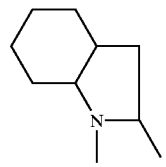
AD-2

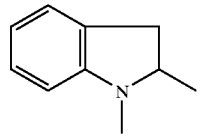
AD-3

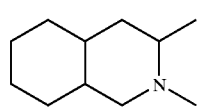
AD-4

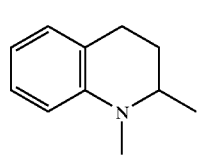
AD-5

AD-6

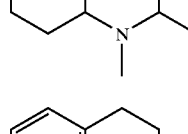
AD-7

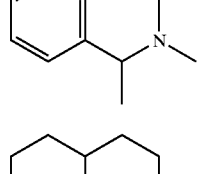
AD-8

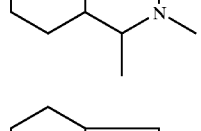
AD-9

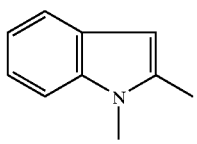
AD-10 or

A and $Q^1$ together represent $C_3$–$C_4$-alkanediyl or $C_3$–$C_4$-alkenediyl, which is optionally mono- or disubstituted by a substituent selected from the group consisting of fluorine, chlorine, hydroxyl and $C_1$–$C_8$-alkyl and $C_1$–$C_4$-alkoxy, which may optionally be mono- to trisubstituted by fluorine, or $Q^1$ represents hydrogen, $Q^2$ represents hydrogen, $Q^4$, $Q^5$ and $Q^6$ independently represent hydrogen or $C_1$–$C_3$-alkyl, $Q^3$ represents hydrogen, $C_1$–$C_4$-alkyl, $C_1$–$C_4$-alkoxy-$C_1$–$C_2$-alkyl, $C_1$–$C_4$-alkylthio-$C_1$–$C_2$-alkyl or optionally methyl- or methoxy-substituted $C_3$–$C_6$-cycloalkyl in which optionally one methylene group is replaced by oxygen or sulphur, or $Q^3$ and $Q^4$ together with the carbon atom to which they are attached represent optionally $C_1$–$C_4$-alkyl- or $C_1$–$C_4$-alkoxy-substituted saturated $C_5$–$C_6$-cycloalkyl in which optionally one ring member is replaced by oxygen or sulphur, L represents an alkanediyl group having 1 to 4 carbon atoms, M represents one of the groupings below:

CN;

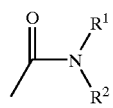

—$CO_2R^2$, —$OR^2$, —$SR^2$, —$COR^3$,

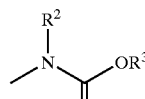 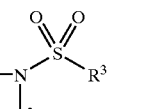 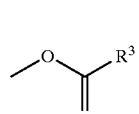

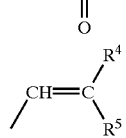

wherein $R^1$ represents hydrogen or $C_1$–$C_{10}$-alkyl, $R^2$ represents optionally fluorine-, chlorine-, bromine-substituted $C_1$–$C_{10}$-alkyl, $C_3$–$C_6$-alkenyl, $C_3$–$C_6$-alkynyl, $C_3$–$C_8$-cycloalkyl, $C_1$–$C_6$-alkoxy-$C_2$–$C_6$-alkyl, $C_1$–$C_6$-alkylthio-$C_2$–$C_6$-alkyl, represents optionally fluorine-, chlorine-, bromine-, nitro-, cyano-, $C_1$–$C_4$-alkylthio-, $C_1$–$C_4$-alkoxy-, $C_1$–$C_4$-halogenoalkoxy-, $C_1$–$C_4$-halogeno-alkylthio-, $C_1$–$C_4$-alkyl- or $C_1$–$C_4$-halogenoalkyl-substituted phenyl or benzyl, $R^3$ represents optionally fluorine-, chlorine-, bromine-substituted $C_1$–$C_{10}$-alkyl or represents optionally fluorine-, chlorine-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl or benzyl, $R^4$ represents hydrogen, fluorine, chlorine, bromine, optionally fluorine- or chlorine-substituted $C_1$–$C_5$-alkyl or optionally fluorine-, chlorine-, bromine-, $C_1$–$C_4$-alkyl-, $C_1$–$C_4$-alkoxy-, $C_1$–$C_2$-halogenoalkyl-, $C_1$–$C_2$-halogenoalkoxy, cyano- or nitro-substituted phenyl, $R^5$ represents hydrogen, fluorine, chlorine, bromine or optionally fluorine- or chlorine-substituted $C_1$–$C_4$-alkyl, G represents fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, m represents the number 0, 1 or 2.

4. The compound of claim 1, wherein

W represents hydrogen, chlorine, fluorine, methyl, ethyl, methoxy, ethoxy,

X represents fluorine, chlorine, methyl, ethyl, n-propyl, isopropyl, methoxy, ethoxy, n-propoxy, isopropoxy, trifluoromethyl, difluoromethoxy, trifluoromethoxy, nitro or cyano, Y represents one of the radicals

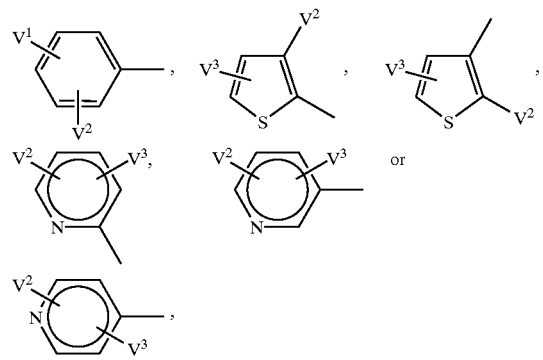

wherein $V^1$ represents hydrogen, fluorine, chlorine, bromine, methyl, ethyl, n-propyl, isopropyl, n-butyl, isobutyl, tert-butyl, methoxy, ethoxy, n-propoxy, isopropoxy, trifluoromethyl, trifluoromethoxy, nitro, cyano or phenyl, $V^2$ and $V^3$ inpendently represent hydrogen, fluorine, chlorine, methyl, ethyl, n-propyl, isopropyl, methoxy, ethoxy, trifluoromethyl or trifluoromethoxy, Z represents hydrogen, fluorine, chlorine, methyl or methoxy, CKE represents one of the groups

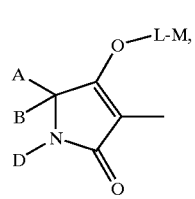

(1)

-continued

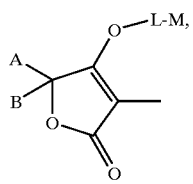
(2)

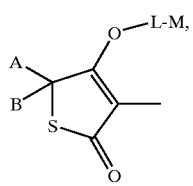
(3)

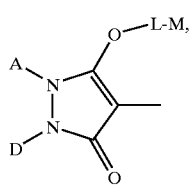
(4)

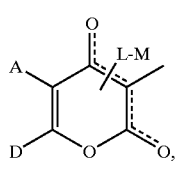
(5)

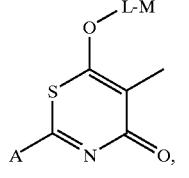
(6)

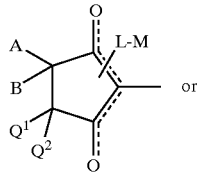
(7)

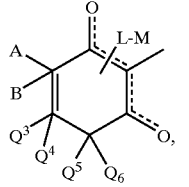
(8)

wherein

A represents hydrogen, optionally fluorine-substituted $C_1$–$C_8$-alkyl or $C_1$–$C_6$-alkoxy-$C_1$–$C_4$-alkyl, optionally fluorine-, methyl-, ethyl- or methoxy-substituted $C_3$–$C_6$-cycloalkyl, in which optionally one ring member is replaced by oxygen or sulphur, or (but not in the case of the compounds of formulae (I-5), (I-7) and (I-8)) represents optionally fluorine-, chlorine-, bromine-, methyl-, ethyl-, n-propyl-, isopropyl-, methoxy-, ethoxy-, trifluoromethyl-, trifluoromethoxy-, cyano- or nitro-substituted phenyl or benzyl, B represents hydrogen or $C_1$–$C_4$-alkyl, or A, B and the carbon atom to which they are attached represent saturated $C_5$–$C_6$-cycloalkyl in which optionally one ring member is replaced by oxygen or sulphur and which is optionally monosubstituted by methyl, ethyl, n-propyl, isopropyl, butyl, isobutyl, sec-butyl, tert-butyl, trifluoromethyl, methoxy, ethoxy, n-propoxy, isopropoxy, n-butoxy, isobutoxy, sec-butoxy, tert-butoxy, fluorine or chlorine, or A, B and the carbon atom to which they are attached represent $C_5$–$C_6$-cycloalkyl in which two substituents together with the carbon atoms to which they are attached represent $C_2$–$C_4$-alkanediyl or $C_2$–$C_4$-alkenediyl, in which optionally one methylene group is replaced by oxygen or sulphur, or butadienediyl, D represents hydrogen, represents optionally fluorine- or chlorine-substituted $C_1$–$C_8$-alkyl, $C_3$–$C_4$-alkenyl, $C_1$–$C_6$-alkoxy-$C_2$–$C_4$-alkyl, $C_1$–$C_4$-alkylthio-$C_2$–$C_4$-alkyl or $C_3$–$C_6$-cycloalkyl, in which optionally one methylene group is replaced by oxygen or sulphur, or (but not in the case of the compounds of formulae (I-1) and (14)) represents in optionally fluorine-, chlorine-, methyl-, ethyl-, n-propyl-, isopropyl-, methoxy-, ethoxy-, trifluoromethyl- or trifluoromethoxy-substituted phenyl, furanyl, pyridyl, thienyl or benzyl, or A and D together represent optionally substituted $C_3$–$C_4$-alkanediyl in which optionally one carbon atom is replaced by sulphur and which is optionally substituted by hydroxyl, methyl, ethyl, methoxy or ethoxy, or A and D (in the case of the compounds of the formula (I-1)) together with the atoms to which they are attached represent one of the groups AD below:

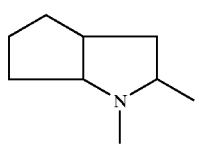
AD-1

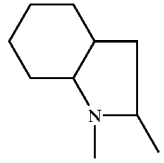
AD-2

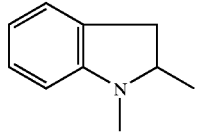
AD-3

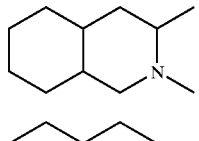
AD-4

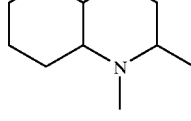
AD-6

-continued

AD-8

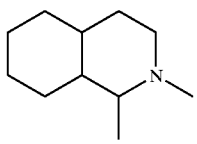

AD-10

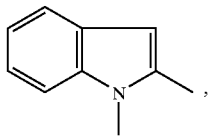,

A and $Q^1$ together represent butenediyl or $C_3$–$C_4$-alkanediyl, optionally mono- or disubstituted by fluorine, hydroxyl, methyl or methoxy, or $Q^1$ represents hydrogen, $Q^2$ represents hydrogen, $Q^4$, $Q^5$ and $Q^6$ independently represent hydrogen, methyl or ethyl, $Q^3$ represents hydrogen, methyl, ethyl or $C_3$–$C_6$-cycloalkyl, in which optionally one methylene group is replaced by oxygen or sulphur, or $Q^3$ and $Q^4$ together with the carbon to which they are attached represent optionally methyl- or methoxy-substituted saturated $C_1$–$C_6$-cycloalkyl in which optionally one ring member is replaced by oxygen or sulphur, L represents one of the groupings below

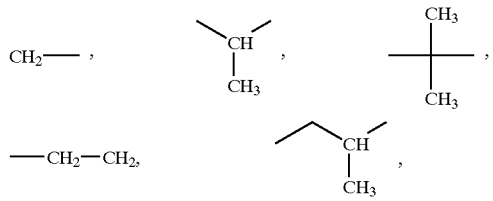

M represents one of the groupings below:
CN;

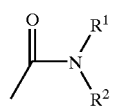

—$CO_2R^2$, —$OR^2$, —$SR^2$, —$COR^3$,

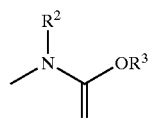 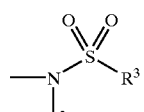

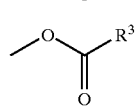 

-continued

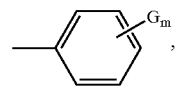 or 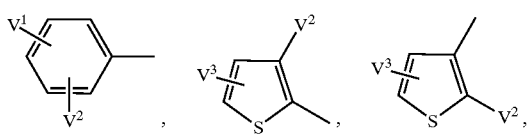, wherein $R^1$ represents hydrogen or $C_1$–$C_8$-alkyl, $R^2$ represents optionally fluorine-, chlorine-, bromine-substituted $C_1$–$C_8$-alkyl, $C_3$–$C_4$-alkenyl, $C_3$–$C_4$-alkynyl, cyclopropyl, cyclopentyl, cyclohexyl, $C_1$–$C_6$-alkoxy-$C_2$–$C_4$-alkyl, $C_1$–$C_6$-alkylthio-$C_2$–$C_4$-alkyl, represents optionally fluorine-, chlorine-, bromine-, nitro-, cyano-, methylthio-, ethylthio-, methoxy-, ethoxy-, trifluoromethylthio-, trifluoromethoxy-, methyl-, ethyl-, trifluoromethyl-substituted phenyl or benzyl, $R^3$ represents optionally fluorine-, chlorine-, bromine-substituted $C_1$–$C_8$-alkyl or optionally fluorine-, chlorine-, $C_1$–$C_2$-alkyl-, trifluoromethyl-, $C_1$–$C_2$-alkoxy- or trifluoromethoxy-substituted phenyl or benzyl, $R^4$ represents hydrogen, fluorine, chlorine, optionally fluorine- or chlorine-substituted $C_1$–$C_4$-alkyl or optionally fluorine-, chlorine-, methyl-, ethyl-, methoxy-, ethoxy-, trifluoromethyl-, difluoromethoxy-, trifluoromethoxy-, cyano- or nitro-substituted phenyl, $R^5$ represents hydrogen, fluorine, chlorine or optionally fluorine- or chlorine-substituted methyl, ethyl, propyl or isopropyl, G represents fluorine, chlorine, methyl, ethyl, propyl, isopropyl, methoxy, ethoxy, propoxy, isopropoxy, trifluoromethyl, difluoromethoxy, trifluoromethoxy, cyano or nitro, m represents a number from 0 to 2.

5. The compound of claim 1, wherein

W represents hydrogen, chlorine, fluorine, methyl, ethyl, methoxy, ethoxy,

X represents fluorine, chlorine, methyl, ethyl, n-propyl, isopropyl, methoxy, ethoxy, n-propoxy, isopropoxy, trifluoromethyl, difluoromethoxy, trifluoromethoxy, nitro or cyano, Y represents one of the radicals wherein $V^1$ represents hydrogen, fluorine, chlorine, methyl, ethyl, n-propyl, isopropyl, n-butyl, isobutyl, tert-butyl, methoxy, ethoxy, n-propoxy, isopropoxy, trifluoromethyl, trifluoromethoxy, nitro, cyano or phenyl, $V^2$ represents hydrogen, fluorine, chlorine, methyl, methoxy, trifluoromethyl or trifluoromethoxy, $V^3$ represents hydrogen, methyl or chlorine, Z represents hydrogen, fluorine, chlorine, methyl or methoxy, CKE represents one of the groups

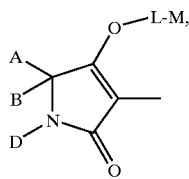 (1)

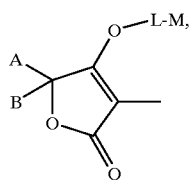 (2)

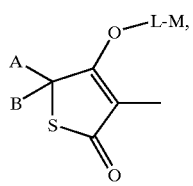 (3)

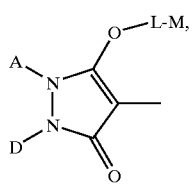 (4)

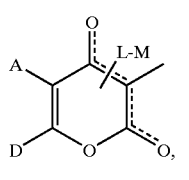 (5)

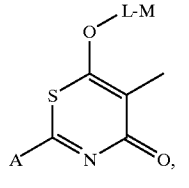 (6)

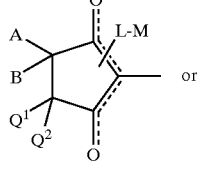 (7)

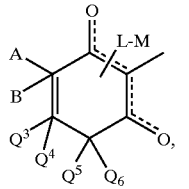 (8)

wherein

A represents hydrogen, optionally fluorine-substituted $C_1$–$C_8$-alkyl or $C_1$–$C_6$-alkoxy-$C_1$–$C_4$-alkyl, optionally fluorine-, methyl- or methoxy-substituted $C_3$–$C_6$-cycloalkyl, in which optionally one ring member is replaced by oxygen or sulphur, or (but not in the case of the compounds of the formulae (I-5), (I-7) and (I-8)) represents optionally fluorine-, chlorine-, bromine-, methyl-, methoxy-, trifluoromethyl- or trifluoromethoxy-substituted phenyl or benzyl, B represents hydrogen or $C_1$–$C_4$-alkyl, or A, B and the carbon atom to which they are attached represent saturated $C_5$–$C_6$-cycloalkyl in which optionally one ring member is replaced by oxygen or sulphur and which is optionally monosubstituted by methyl, ethyl, n-propyl, isopropyl, trifluoromethyl, methoxy, ethoxy, n-propoxy, isopropoxy, n-butoxy or isobutoxy, or A, B and the carbon atom to which they are attached represent $C_5$–$C_6$-cycloalkyl in which two substituents together with the carbon atoms to which they attached represent $C_2$–$C_4$-alkanediyl or $C_2$–$C_4$-alkenediyl in which optionally one methylene group is replaced by oxygen or sulphur, or butadienediyl, D represents hydrogen, represents optionally fluorine- or chlorine-substituted $C_1$–$C_6$-alkyl, $C_3$–$C_4$-alkenyl, $C_1$–$C_4$-alkoxy-$C_2$–$C_4$-alkyl, $C_1$–$C_4$-alkylthio-$C_2$–$C_4$-alkyl or $C_3$–$C_6$-cycloalkyl, in which optionally one methylene group is replaced by oxygen or sulphur, or (but not in the case of the compounds of the formulae (I-1) and (I-4)), represents optionally fluorine-, chlorine-, methyl-, methoxy-, trifluoromethyl- or trifluoromethoxy-substituted phenyl, pyridyl or benzyl, or A and D together represent optionally substituted $C_3$–$C_4$-alkanediyl in which optionally one carbon atom is replaced by sulphur and which is optionally substituted by methyl or methoxy, A and $Q^1$ together represent butenediyl or $C_3$–$C_4$-alkanediyl, optionally mono- or disubstituted by methyl or methoxy, or $Q^1$ represents hydrogen, $Q^2$ represents hydrogen, $Q^4$, $Q^5$ and $Q^6$ independently represent hydrogen, methyl or ethyl, $Q^3$ represents hydrogen, methyl, ethyl or $C_3$–$C_6$-cycloalkyl in which optionally one methylene group is replaced by oxygen or sulphur, $Q^3$ and $Q^4$ together with the carbon to which they are attached represent optionally methyl- or methoxy-substituted saturated $C_5$–$C_6$-cycloalkyl in which optionally one ring member is replaced by oxygen or sulphur, L represents one of the groupings below:

—$CH_2$—,

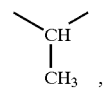

—$CH_2$—$CH_2$,

M represents one of the groupings below:

CN;

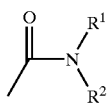

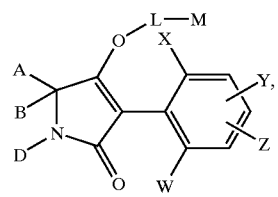 (I-1)

—CO₂R², —OR², —SR², —COR³,

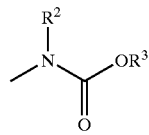     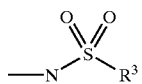

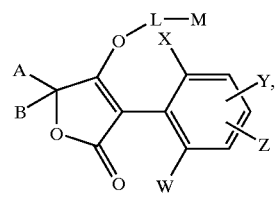 (I-2)

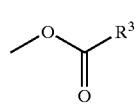     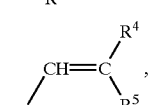

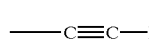     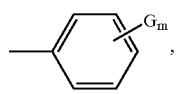

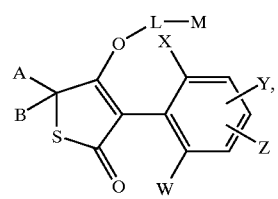 (I-3)

wherein

R¹ represents hydrogen or $C_1$–$C_4$-alkyl,

R² represents optionally fluorine-substituted $C_1$–$C_4$-alkyl, $C_3$–$C_4$-alkenyl, $C_3$–$C_4$-alkynyl, cyclopropyl, cyclopentyl, cyclohexyl, $C_1$–$C_4$-alkoxy-$C_2$–$C_4$-alkyl, represents optionally fluorine-, chlorine-, bromine-, nitro-, cyano-, methylthio-, ethylthio-, methoxy-, ethoxy-, trifluoromethylthio, trifluoromethoxy-, methyl-, ethyl-, trifluoromethyl-substituted phenyl or benzyl,

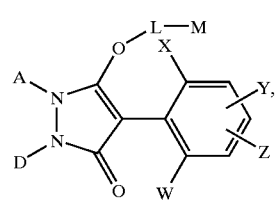 (I-4)

R³ represents optionally fluorine-substituted $C_1$–$C_4$-alkyl or optionally fluorine-, chlorine-, methyl-, trifluoromethyl-, methoxy- or trifluoromethoxy-substituted phenyl, R⁴ represents hydrogen, fluorine, chlorine, optionally fluorine-substituted $C_1$–$C_4$-alkyl or optionally fluorine-, chlorine-, methyl-, ethyl-, methoxy-, ethoxy-, trifluoromethyl-, difluoromethoxy-, trifluoromethoxy-, cyano- or nitro-substituted phenyl,

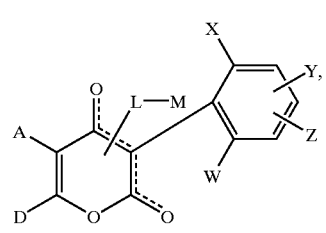 (I-5)

R⁵ represents hydrogen, fluorine, chlorine or optionally fluorine-substituted methyl, G represents fluorine, chlorine, methyl, methoxy, trifluoromethyl, difluoromethoxy, trifluoromethoxy, cyano or nitro, m represents a number from 0 to 1.

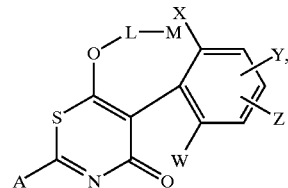 (I-6)

6. A pesticide and/or herbicide comprising at least one compound of claim 1.

7. A method of controlling a pest and/or weed, comprising applying at least one compound of claim 1 to at least one of the pest, weed and/or its habitat.

8. A process for preparing compounds of the formulae (I-1) to (I-8) of claim 1

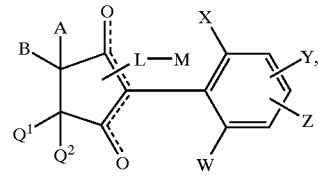 (I-7)

-continued (I-8)

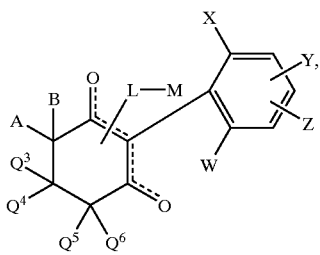

wherein

A, B, D, L, M, $Q^1$, $Q^2$, $Q^3$, $Q^4$, $Q^5$, $Q^6$, W, X, Y and Z are as defined above, comprising reacting a compound of the formulae (II-1) to (II-8)

(II-1)

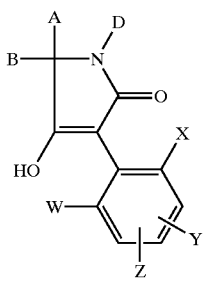

(II-2)

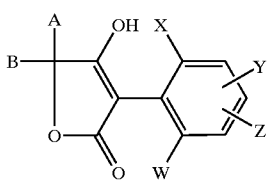

(II-3)

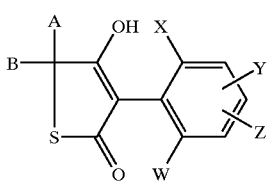

(II-4)

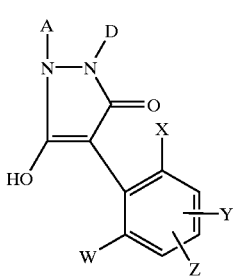

(II-5)

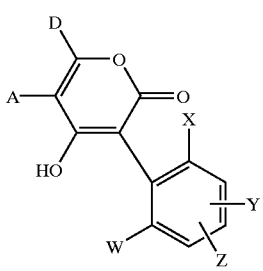

(II-6)

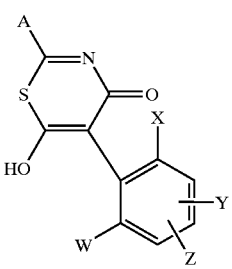

(II-7)

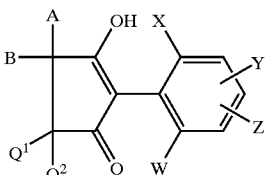

(II-8)

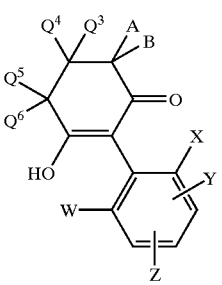

wherein

A, B, D, $Q^1$, $Q^2$, $Q^3$, $Q^4$, $Q^5$, $Q^6$, W, X, Y and Z are as defined above, with a compound of the formula (III)

$$J\text{---}L\text{---}M \qquad (III)$$

wherein

L and M are as defined above and

J represents a leaving group, such as halogen, —O—SO$_2$-halogenoalkyl, —O—SO$_2$-alkyl or —O—SO$_2$-aryl, in the presence of a diluent and in the presence of a base; and collecting the reaction product.

9. A process for preparing a pesticide and/or herbicide, comprising mixing at least one compound of claim 1 with at least one of extenders and surfactants.

* * * * *